United States Patent
Jorden et al.

(10) Patent No.: US 11,498,858 B2
(45) Date of Patent: Nov. 15, 2022

(54) METHODS FOR OPTIMIZING WATER TREATMENT COAGULANT DOSING

(71) Applicant: Clearcorp, Longmont, CO (US)

(72) Inventors: Roger Miles Jorden, Longmont, CO (US); Bert Vermeulen, Cheyenne, WY (US)

(73) Assignee: Clearcorp, Longmont, CO (US)

( * ) Notice: Subject to any disclaimer, the term of this patent is extended or adjusted under 35 U.S.C. 154(b) by 503 days.

(21) Appl. No.: 16/417,388

(22) Filed: May 20, 2019

(65) Prior Publication Data

US 2019/0270655 A1    Sep. 5, 2019

Related U.S. Application Data

(63) Continuation-in-part of application No. 15/584,871, filed on May 2, 2017, now Pat. No. 10,338,631.

(51) Int. Cl.
*C02F 1/52*         (2006.01)
*C02F 1/56*         (2006.01)
(Continued)

(52) U.S. Cl.
CPC .......... *C02F 1/5209* (2013.01); *C02F 1/5236* (2013.01); *C02F 1/56* (2013.01);
(Continued)

(58) Field of Classification Search
CPC .................................................. C02F 1/5209
See application file for complete search history.

(56) References Cited

U.S. PATENT DOCUMENTS

| 2,310,009 A | 2/1943 | Baker et al. |
| 4,170,553 A | 10/1979 | Lang et al. |

(Continued)

OTHER PUBLICATIONS

Mantovanelli et al., "SEDVEL: An underwater balance for measuring in situ settling velocities and suspended cohesive sediment concentrations," "Journal of Sea Research", Retrieved on Sep. 22, 2009_2 pages. Retrieved from: http://www.sciencedirect.com/science/article/pii/S1385110108001093.

(Continued)

*Primary Examiner* — Peter Keyworth
(74) *Attorney, Agent, or Firm* — Kilpatrick Townsend & Stockton LLP

(57) ABSTRACT

Embodiments of the invention comprise methods and systems for optimizing coagulant dosing of raw water in a water treatment process. First, the embodiments determine the optimum dosage of pH adjusting chemicals to be added to the raw water based on a measurement of dissolved organic content, alkalinity, and pH of the raw water. Then, the embodiments perform a flocculation test of a mixture of the optimally-pH-dosed raw water and a hydrolyzing metal salt (HMS) wherein the dosage of the HMS salt in the mixture can be calculated based on a measurement of the charge demand of the optimally-pH-dosed raw water. The results of this flocculation test are compared to the results of at least one previous test of a combination of optimally-pH-dosed raw water and HMS to determine if the hydrolyzing metal salt dose is optimized. Once the HMS is optimized, the optimally-HMS-dosed optimally-pH-dosed water is tested with at least two different dosages of a polymer coagulant to determine the optimal polymer coagulant dosage to be used with the optimally-HMS-dosed optimally-pH-dosed water.

20 Claims, 25 Drawing Sheets

(51) Int. Cl.
*C02F 1/66* (2006.01)
*G01N 33/18* (2006.01)

(52) U.S. Cl.
CPC .............. *C02F 1/66* (2013.01); *G01N 33/18* (2013.01); *C02F 2209/06* (2013.01); *C02F 2209/07* (2013.01); *C02F 2209/105* (2013.01); *C02F 2209/44* (2013.01)

(56) References Cited

U.S. PATENT DOCUMENTS

| | | | |
|---|---|---|---|
| 4,282,093 | A | 9/1981 | Haga et al. |
| 4,654,139 | A | 3/1987 | Baba et al. |
| 4,752,131 | A | 6/1988 | Eisenlauer et al. |
| 4,783,269 | A | 11/1988 | Baba et al. |
| 4,855,061 | A | 8/1989 | Martin |
| 4,867,886 | A | 9/1989 | Botkins, Jr. |
| 4,950,908 | A | 8/1990 | Oblad et al. |
| 5,194,921 | A | 3/1993 | Tambo et al. |
| 5,376,280 | A | 12/1994 | Wilhelm et al. |
| 5,380,440 | A | 1/1995 | Chipps |
| 7,037,433 | B2 | 5/2006 | Abu-Orf et al. |
| 7,303,685 | B2 | 12/2007 | Clark |
| 8,303,893 | B2 | 11/2012 | Yamaguchi et al. |
| 9,618,438 | B2 | 4/2017 | Jorden |
| 2011/0060533 | A1* | 3/2011 | Jorden ............ G01N 33/18 702/23 |
| 2016/0223452 | A1 | 8/2016 | Milosevic et al. |

OTHER PUBLICATIONS

Jin, Yan, "Use of a High Resolution Photographic Technique for Studying Coagulation/Flocculation in Water Treatment," "Department of Civil and Geological Engineering University of Saskatchewan Saskatoon", May 2005_152 pages, Retrieved from: https://ecommons.usask.ca/bitstream/handle/10388/etd-06042005-213443/MScThesis_YanJin.pdf.

Jarvis et al., "Measuring Floc Structural Characteristics,"Reviews in Environmental Science and Biotechnology, vol. 4 (1-2), May 2005_pp. 1-18, Retrieved from: https://core.ac.uk/download/pdf/137927.pdf.

Mantovanelli, "A new approach for measuring situ the concentration and settlign velocity of suspended cohesive sediment, "PhD thesis, James Cook University, Mar. 2005_215 pages, Retrieved from https://researchonline.jcu.edu.au/5326/2/02whole.pdf.

Manning et al., "The use of optics for the in situ determination of flocculated mud characteristics," "Journal of Optics A: Pure and Applied Optics", vol. 4, No. 4, Jul. 8, 2002_pp. 1-2, Retrieved from: http://iopscience.iop.org/article/10.1088/1464-4258/4/4/366/meta;jsessionid=5E930BF7CFAAFE4CFC5BC1077BED3275.c3.iopscience.cld.iop.org.

Van der Lee, "Temporal Variation of Floc Size and Settling Velocity in the Dollard Estuary," "Continental Shelf Research", vol. 20(12-13) 2000_ pp. 77-93. Retrieved from: https://dspace.library.uu.nl/bitstream/handle/1874/524/c5.pdf;jsessionid=287BA9DA4876E8D97BA9D7B4B6721622?sequence=14.

Ingels, Tyson, "Optimizing Granular media Filtration Through Bench-Scale and In-Situ Floc Particle Characterization," "Colorado School of Mines Thesis", 2006_pp. 1-165.

Clearcorp, "Automated Jar Tester with In-Line Coagulation," "RoboJar Data Sheet" Feb. 14, 2006_pp. 1-5.

Clearcorp, "In-Line Floc Particle Imaging Sensor with Size Analysis,"FlocMonitor Data Sheet, Sep. 11, 2006_pp. 1-2.

ClearCorp "On-Line 'Jar Testing' of Full Process Stream: The New Chemical-Dosing/Filtration-Performance Optimizer", Dec. 7, 2005_ pp. 1-5.

Drewes et al., "State-of-the-Art Floc Particle Characterization—Optimizing Granular Media Filtration," "Presentation at AWWA Water Quality Technology Conference", 2006_pp. 1-1.

Ingels et al., "Optimizing Filtration Pre-Treatment Processes Through State of the Art Floc Particle Characterization" "Presentation at AWWA Water Quality Technology Conference", 2005_pp. 1-33.

Hartog et al., "Fluidized-Bed Reactor to Study Physico-Chemical Kinetics in Heterogeneous Soils and Sediments," "Geologica Ultraiectina", vol. 228_pp. 1-12, Retrieved from https://dspace.library.uu.ni/bitstream/handle/1874/582/c2.pdf;jsessionid=C59F052D3EDB5BA13A637B3180769B70?sequence=7.

ClearCorp, "Jar-FlocCam Brochure" Retrieved Feb. 22, 2017_pp. 1-6.

Satterfield, "Tech Brief: Jar Testing," "National Environmental Services Center", Retrieved Feb. 11, 2017_pp. 1-4.

Colloid Charge Capacity—Its Measurement, Problems, and Promise, by Roger M. Jorden. Proceedings of the $7^{th}$ Gothenburg Symposium, Sep. 23-25, 1996, (Abstract of).

Use of Zeta Potential to Optimize Full-Scale Treatment of High TOC Water, by Judith Billica and Kevin Gertig at the 2006 Water Works Association WQTC Conference. (Abstract of).

Enhanced Coagulation: USA Requirements and a Broader View by James Edzwald and John Tobiason. Water Science and Technology vol. 40 (No. 9) 1999. (Abstract of).

* cited by examiner

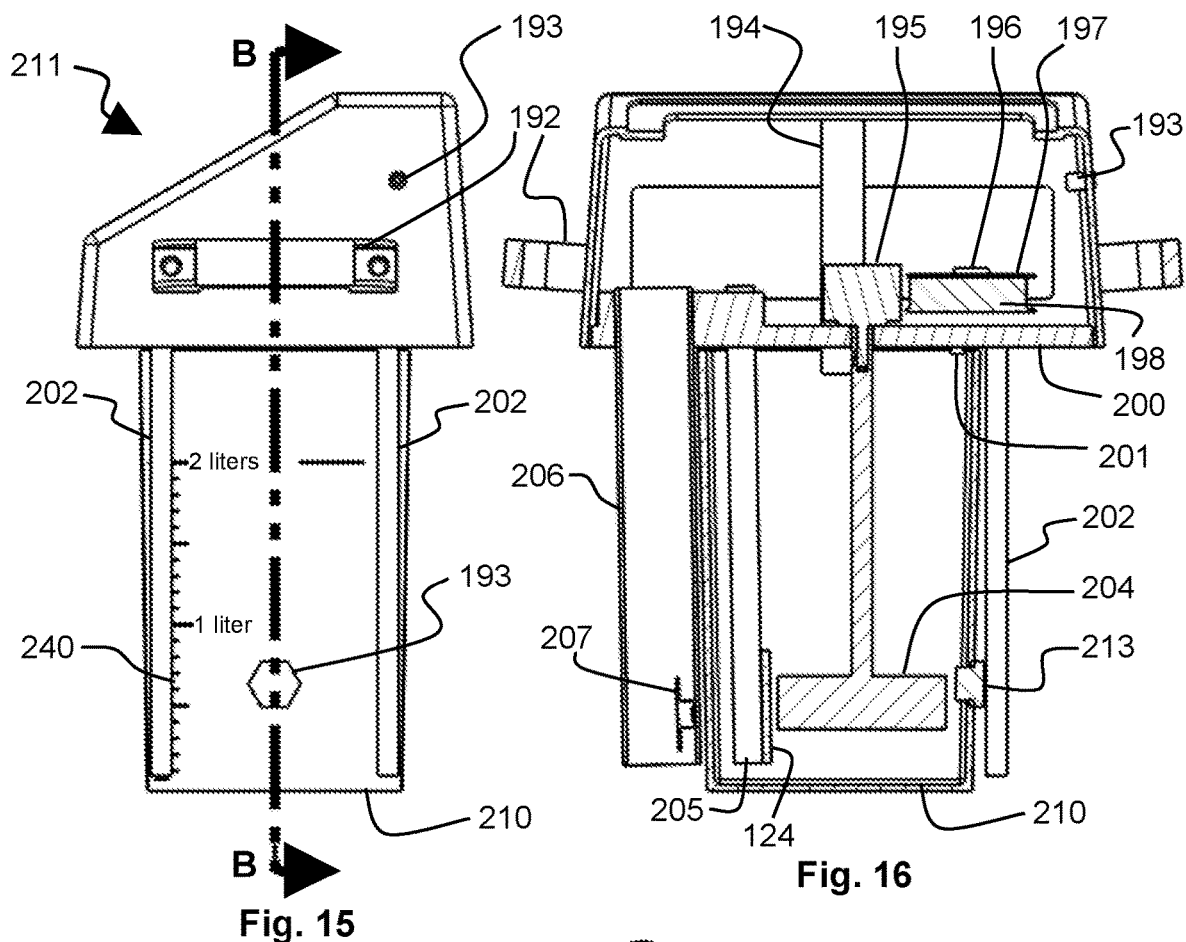
Fig. 15
Fig. 16
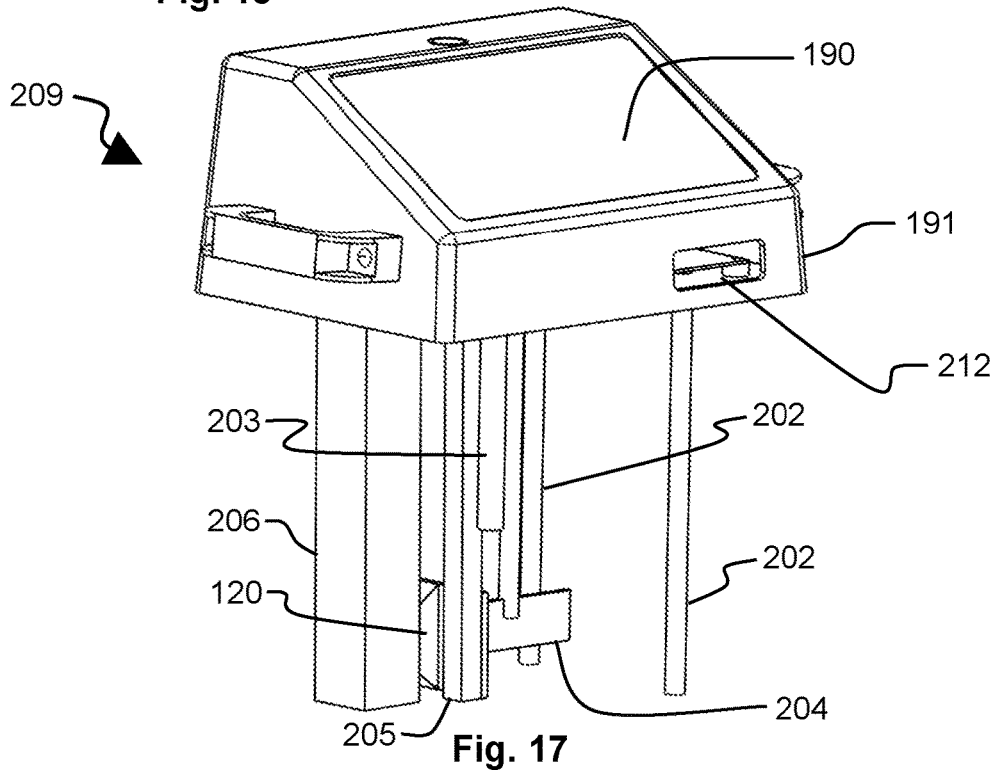
Fig. 17

Fig. 22
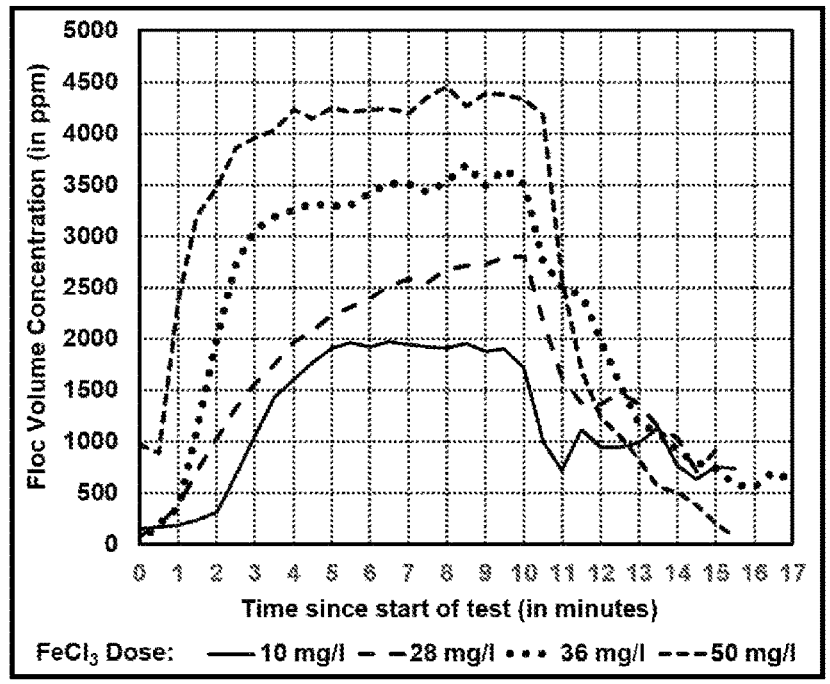
Fig. 23
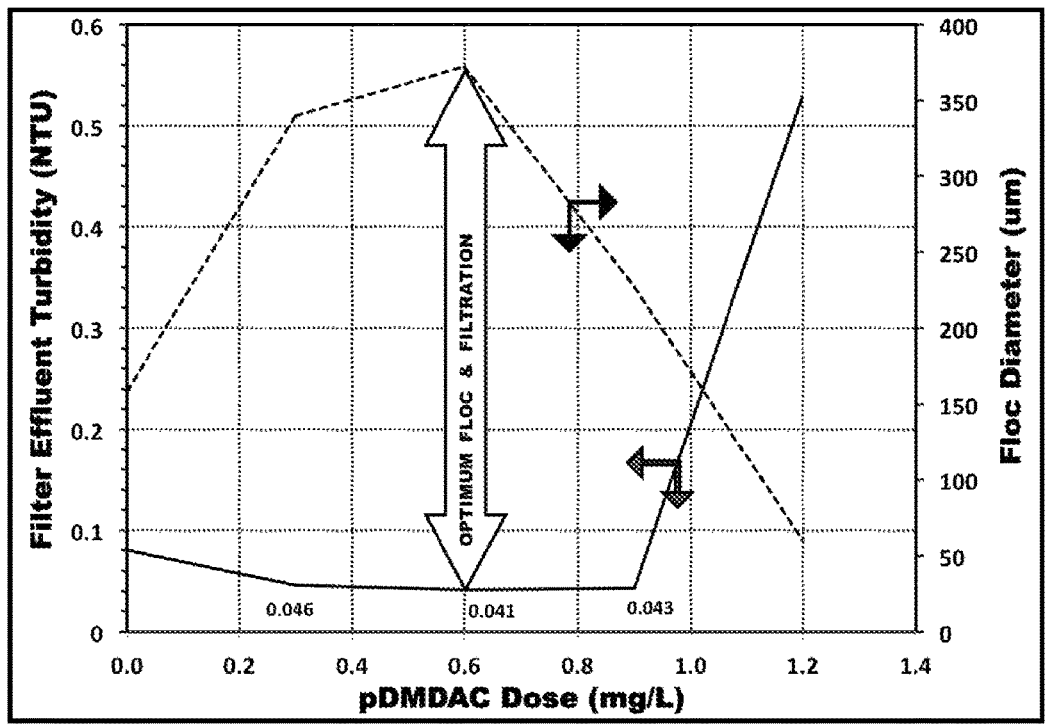
Fig. 24
| Decision table for process polymer dosage changes | | |
|---|---|---|
| If dosage was ... | .... and floc size is ... | ... then ... |
| Decreased | Smaller | Increase dosage |
| Decreased | Larger | Decrease dosage |
| Increased | Smaller | Decrease dosage |
| Increased | Larger | Increase dosage |

```
                    ┌─3022A    ┌─3022B              ┌─3100
                    │          │                    │
                  ┌─┴──────────┴────────────────────┴──────────────┐
                  │          Experimental Run Controls             │
        4309─┐    │ START Run │ STOP/ABORT Run │ CREATE New Protocol │ CLOSE Window │
        4301─┐    │ Current Stage: None        RPM: 0        Seconds: 0          │
                  ├────────────────────────────────────────────────┤
        4303─┐    │ Mixing Protocol: Binney ▼  Edit Protocol  Delete Protocol    │
        4304─┐    │ Run Title:       Mid Train                                   │
        4305─┐    │ Run Chemistry:   Fe                                          │
                  │ Run Dosage:      5.5                                         │
        4308─┐    │                  ┌─────────────┐                             │
                  │ Comments:        │ Sample A    │                             │
                  │                  └─────────────┘                             │
        4306─┐    │ Recording Period: 30 Minutes ▼                               │
        4307─┐    │ Recording Delay:  0   Minutes  0   Seconds                   │
        4302─┐    │ Stage/ID    Comment        Duration (M:S)      RPM           │
                  │   1 - 5     Breakup            0:10           250            │
                  │   2 - 6     Mix                5:0             25            │
                  │   3 - 7     Settle             2:0              0            │
                  └────────────────────────────────────────────────┘
```

Fig. 28

```
                                       ┌─3124
                  ┌────────────────────┴────────────────────────┐
                  │          Experimental Protocol Editor       │
                  │        │ Update/Save Protocol │ Cancel/Close │
        4403─┐    │ Mixing Protocol:  new                        │
        4404─┐    │ Protocol Title:   My Protocol                │
        4405─┐    │ Run Chemistry:    My Sample Chemistry        │
                  │ Run Dosage:       Default Dosage             │
        4408─┐    │ Comments:         Helpful Notes go here      │
        4406─┐    │ Recording Period: 10 Minutes ▼               │
        4407─┐    │ Recording Delay:  0   Minutes  0   Seconds   │
                  │ Protocol Stages   Add Stage                  │
        4410─┐    │ Stage   Comment   Duration (M:S)  RPM  Edit  Delete │
                  │   1     Breakup       0:10        250   ✓      ☐   │
                  └──────────────────────────────────────────────┘
                                     │               │       │
                                   4411           4412     3114
```

Fig. 29

```
                         ┌─4504
                  ┌──────┴──────────────────────────────────┐
                  │    Experimental Protocol Stage Editor    │
                  │       │ Update/Save Stage │ Cancel │     │
        4502─┐    │ Stage Duration:  0   Minutes  10  Seconds │
        4503─┐    │ RPM (equivalent): 250                     │
        4501─┐    │ Label/Comment:   Breakup                  │
                  └──────────────────────────────────────────┘
```

Fig. 30

METHODS FOR OPTIMIZING WATER TREATMENT COAGULANT DOSING

This application is a continuation-in-part of application Ser. No. 15/584,871 filed 2 May 2017, which is incorporated herein by reference.

FIELD OF INVENTION

This invention relates to a methods and systems for optimizing coagulant dosing for water treatment and more specifically for the treatment of raw water in a water treatment process, plant, and/or any other system that produces drinking water.

BACKGROUND

Coagulation is the initial process in water-pollutant separation systems. Flocculation immediately follows coagulation. Combined, coagulation-flocculation represents pretreatment processing for the formation of floc (approximately millimeter-sized aggregates that incorporate pollutants) and their subsequent physical separation. Removal of floc-pollutants from water is accomplished by separation processes such as gravitational settling, drinking water filtration (using granular-media), membranes and/or desalting pretreatment, wastewater treatment, fats-oil-grease removal from industrial wastewater, waste metal and trace element removal, and dewatering including paper making and sludge dewatering. Coagulant dosage control and flocculation mixing control (to a lesser extent) are the two primary inputs for optimizing and controlling the entire coagulation-flocculation-clarification filtration process.

Coagulation involves chemical addition and dispersion to process water. Coagulation is powerful. It can induce >10,000-fold pollutant-particle size increases, and >1,000,000-fold reduction in number concentration of infectious organisms such as the amoeba *Cryptosporidium*. Coagulation is versatile. It can induce removal of a diverse variety of pollutant species including: Ions of arsenic, phosphorus, fluorine, and trace metals;
  (ii) Dissolved organics that may form carcinogens;
  (iii) Algae, dead microorganisms, cellular detritus:
  (iv) Infectious viruses, bacteria, and amoeba; and
  (v) Particulate matter harboring other pollutants.

The successful application of coagulants represents a challenge because coagulation-flocculation effects are manifold (i.e. many and various), slow to manifest, varied, and used in a wide range of applications. Coagulation-flocculation pretreatment represents the 'big lever' for a plant operator to control pollutant-removal performance, both quality and quantity (throughput).

Coagulation is instantaneous whereas flocculation nominally requires from minutes (for dense slurries) to hours (for dilute suspensions in older facilities). Nominally, coagulation converts otherwise stable, negatively charged pollutant species into neutral 'sticky' bodies that gradually grow in size as a result of particle-particle collisions caused by Brownian motion and mild turbulent fluid mixing. A fundamental requirement of coagulant dosing is that the total negative charged demand of water must be met by the positive-charge supplied by the coagulant chemicals, referred to as charge neutral coagulation. Dosing beyond this point can be more costly or counterproductive. Flocculation results in the aggregation of pollutant-coagulant sub-particles into larger and more easily removable entities, or floc particles. Particle size depends upon the nature of the mixing regime and floc strength characteristics for a given raw water quality and coagulation chemistry. Mixing intensity control represents the physical means for manipulating floc particle characteristics, for a given coagulation-chemistry regime.

Because the terms coagulation and flocculation are used interchangeably by some, these and related terms require defining as to their meaning as used herein. Coagulation refers to the addition of chemical species that lead to the instantaneous precipitation, adsorption, and/or destabilization of dissolved and particulate matter. Flocculation refers to the agglomeration or aggregation of the destabilized colloids and precipitates. Coagulation-flocculation refers to the coupled unit processes as a pretreatment system preceding the pollutant-floc separation step(s).

Prior art (manual) jar tests, used since at least the 1920s, measure turbidity (water cloudiness) after the coagulant addition, flocculation mixing, and settling. No quantitative analysis is made of the visible floc particles. No data about the sample is collected until test completion after settling. More, better and faster information about the coagulation effects, flocculation progress, and gravitational settling processes are desired. Improved test devices, in-process instrumentation, and coagulant dosing analysis methods can dramatically reduce the quantity of coagulant chemicals needed, leading to: (a) reduced chemical costs; (b) increased plant throughput; and (c) reduced filter loading, all of which leads to significant cost savings and better water quality.

BRIEF DESCRIPTION OF THE FIGURES

The present disclosure is described in conjunction with the appended figures in which:

FIG. 15 shows a right-side view of the system of FIG. 13;

FIG. 16 shows section B-B of FIG. 15;

FIG. 17 shows a perspective view of an automated water sample jar testing instrument (with the system's chamber removed);

FIG. 22 shows typical data collected by the automated water sample jar testing system of FIGS. 13-21;

FIG. 23 shows a typical relationship between coagulant dose, floc diameter, and filter effluent turbidity;

FIG. 24 shows a decision table for determining how to change coagulant dosing to improve coagulation/flocculation performance;

FIG. 28 shows an example of a user interface screen for performing step 3006, performing step 3022, and initiating step 3100 in FIG. 19;

FIG. 29 shows an example of a user interface screen for performing steps 3106, 3108, 3114, 3116, and 3124 in FIG. 20; and FIG. 30 shows an example of a user interface screen for performing step 3120 in FIG. 20;

In the appended figures, similar components and/or features may have the same reference label. Where the reference label is used in the specification, the description is applicable to any one of the similar components having the same reference label.

DETAILED DESCRIPTION

A. Overview of Water Treatment

Figure 1:
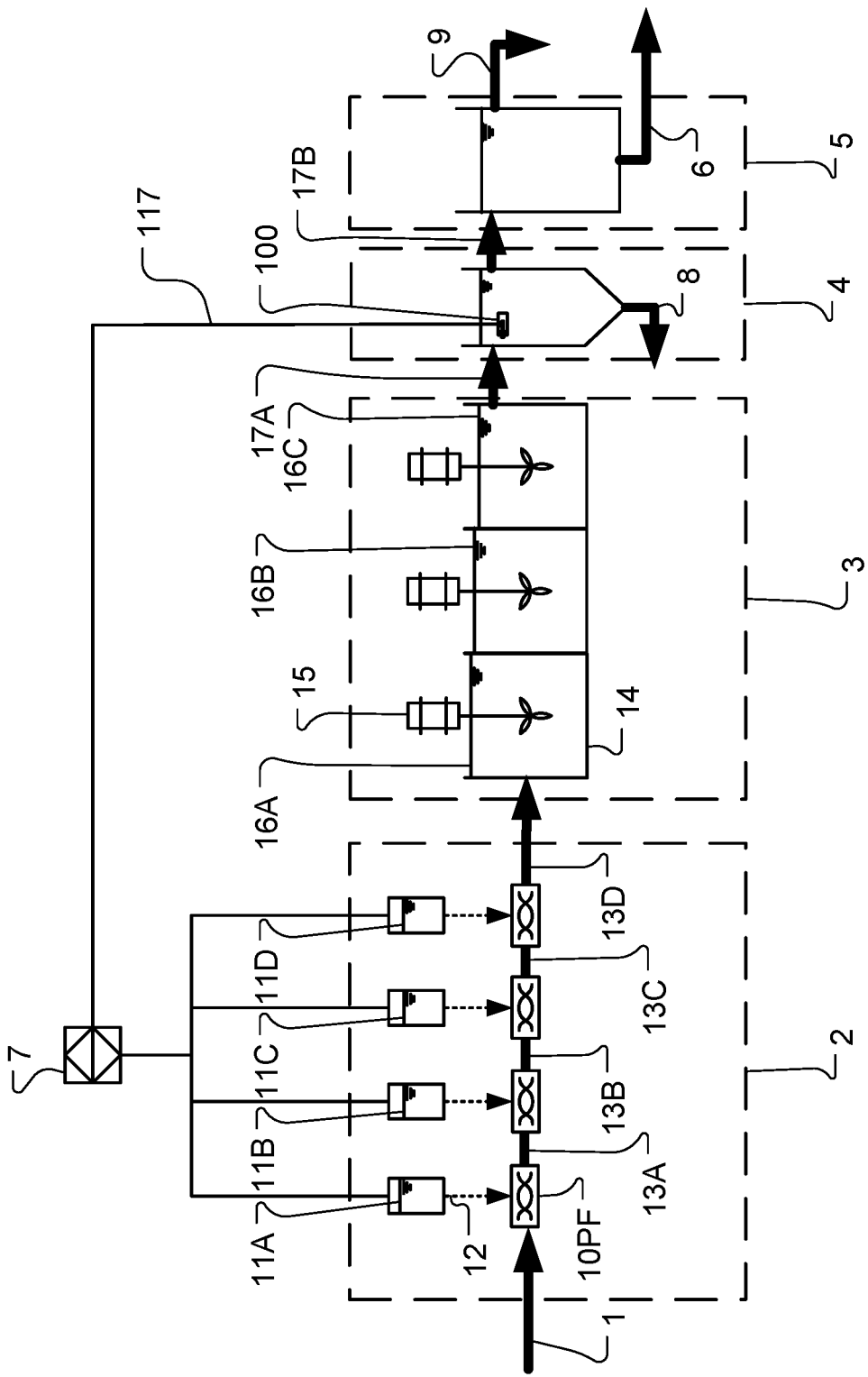
FIG. 1 is a schematic view of a water treatment process with a suspended particle characterization system.

Embodiments of the present invention can be used in a variety of water treatment environments, which typically have some or all the elements shown in FIG. 1. Water treatment is a broad field, and there are many water treatment processes and facilities that can benefit from embodiments of the present invention.

a) In 1990, a prevailing ideology in leadership of the drinking-water industry was that strictly physical processing (membranes, adsorption, oxidation, and biological processing) over chemical-physical processing (coagulation-flocculation, granular-media filtration) was the technology future of the water industry. Coagulation-flocculation was passé. Membranes would obviate the need to waste resources quantifying and automating troublesome process of adjusting coagulation chemistry in response to raw water quality changes.

b) Current prevailing evidence points to an industry future involving a combination of chemical-physical-biological and physical processing. Underlying this transformation of ideology has been the fact that coagulation-flocculation trumps the severe penalties (a three-fold effect arising from the increase of first costs, operating costs, and membrane-replacement costs, combined with reduced throughput i.e., reduced benefit/cost) that colloids inflict upon strictly physical exclusion-adsorption technologies.

c) In some cases, coagulation-filtration plant performance can be increased between 10-fold to 10,000-fold through use of the methods and systems described in the present disclosure, including usage in optimized coagulation-filtration plants capable of near 5.5-log removal of Giardia and *Cryptosporidium* versus a 1.5-log removal of Giardia or *Cryptosporidium* which was the mean value obtained in a nationwide survey of US drinking water plants.

Referring to a water treatment facility shown in FIG. 1, raw water, shown at 1, is mixed with at least one coagulant chemical species, shown at 11a, 11b, 11c, and 11d. Coagulation chemistry refers to effect of adding one or more chemicals, as described below. Coagulant chemical species can include additives variously referred to as coagulants, flocculants, flocculent aids, filter aids, pH adjustment chemicals (acids and/or bases), and oxidants/reductants. A coagulation-chemistry regime for a given water treatment process can involve variations of:

a) One or more classes of chemical species such as oxidants for Mn/Fe removal; pH adjustment chemicals; hydrolyzing metal salts (HMS) such as aluminum sulfate, aluminum chloride, ferric sulfate and/or numerous polymerized derivatives; and/or organic polymer coagulants of which there many species;

b) Sequence and delay times between the addition of the chemical species;

c) Mode and details of additive dispersion; and d) Concentration of each individual coagulant chemical species.

The optimum combination of coagulant species 11a, 11b, 11c, and 11d may vary with location, raw water quality, treatment quality goals, plant separation processing equipment, and with time for a given situation as the input stream of raw water varies in quality. An instrument downstream of these coagulant addition points can be used to help identify whether the correct chemical species and quantities of these species are being added to optimize and control the process. Embodiments of the present invention can comprise such instrumentation as well as methods for monitoring, optimizing, and controlling coagulation-flocculation processing.

There are three distinct optimization domains for water treatment: local, global and universal. Local optimization refers to finding the best input of one coagulate species for floc formation when all other variables are held constant. Global optimization refers to the highest multi-dimensional peak (or valley) in a multi-dimensional domain. An example might be optimizing the dosage of multiple coagulants for a given input water sample (all variables of the water sample held constant). Universal optimization refers to the consideration of all possible combinations of viable coagulant species for a given site (water treatment facility) and the optimal response of all tested coagulant-species combinations on all viable water samples for this site. This would be the same as global optimization, but the variables in the water sample would not be held constant.

B. Overview of Embodiments Described Herein

In one embodiment, the present invention can be used in conjunction with turbidity measurement, a common metric of coagulation-flocculation-filtration performance for drinking water. Turbidity is an optical property involving light scattered from particles. Turbidity is typically measured at the end of the process such as for the treated effluent illustrated at 6 in FIG. 1. Some beneficial features of turbidity measurement can include:

(a) Automatable, reliable, cost effective instruments can be used on every individual filter;
(b) Sensitive for retrospectively judging removal success when diligently calibrated, and maintained but only following effective coagulation-flocculation;
(c) Sensitive to upstream events—but becomes useful for relating cause-effect only following retrospective review to isolate the significant interferences from hydraulic 'noise' and is placed in the context of each filter cycle (following backwash but before breakthrough); and
(d) Turbidity measurement is a suitable regulatory compliance tool.

Embodiments of the present invention can complement turbidity measurement by providing:

(a) Data upstream and earlier than where turbidity can be measured;
(b) Real time data that characterizes the intelligence laden flocculation dynamics of pretreatment progress;
(c) A direct measurement of particles prior to the removal process rather than a measurement of particles not removed; and
(d) A more accurate measure of the health risk of the process water being treated.

The digital-camera-based instrument (suspended particle characterization system) shown at 100 in FIG. 1 can:

a) Measure a surrogate of pollutant-concentration removal success.
b) Work in water treatment facilities that remove pollutants generally representing numerous broad pollutant categories including 100's of genera and species of infectious organisms, carcinogens, potentially formed in processing, other health compromising species such as arsenic, mineral mater, stimulants of microorganism growth ($PO_4^{-2}$), FOG (fats, oils and grease), and fibrous material (e.g. asbestos); a significant challenge indeed.
c) Provide real-time feedback of pollutant-removal progress.
d) Be deployed throughout the entire processing system, including real-time feedback, in situ process analysis, and for use in empirically based reconnaissance testing and mapping of removal in response to operationally controllable variables (coagulation chemistry and mixing).
e) Be calibrated to a known standard.
f) Be correlated to turbidity—the existing de facto surrogate drinking water filtration standard.
g) Be used to measure water quantity (net throughput or production volume) as well as removal quality success.
h) Provide a means to balance among opposing needs and outcomes such as:
 (i) Using empirical based exploratory changes of processing control variables, coagulant dosing, and floc mixing.
 (ii) Using the full process to maintain floc-mixing similitude.

Which can lead to outcomes such as:
(a) Increased risk to effluent quality by exploring change of operation-control variables because of using the full process for 'testing'.
(b) Low similitude level, and increased risk to quality of mapped response by using side-stream simulation exploratory change for flocculation-response mapping.

Embodiments of the present invention can comprise a portable system and/or method for testing a water sample as shown in FIGS. 13-21, which comprises a user-removable chamber for holding the water sample as shown at 210 and an instrument, shown at 209, that can be configured for manual insertion at least partially into the water sample in the chamber 210 through an aperture located in the top portion of the chamber. These embodiments can also incorporate features described with reference to FIG. 1-12.

Embodiments of the present invention can also comprise systems and methods for optimizing water treatment coagulant dosing, such as the systems and methods described with reference to FIG. 24 and FIGS. 31 to 33.

C. Details of the Embodiments

Referring in more detail to FIG. 1 a suspended particle characterization system 100 is deployed in a clarification 4 unit of a water treatment processing system. The water treatment processing system depicted employs coagulation 2 and flocculation 3 processing units of raw water 1 as pretreatment for the formation of floc particles in preparation for the physical separation of a wide variety of pollutant species piggybacked upon suspended floc particles. Said particles are separated from water by downstream removal processes of clarification 4 followed by filtration 5 of the floc/pollutant suspended particles. In this embodiment, the instrument quantifies the physical characteristics of floc particles entering the clarifier. The physical floc characteristics, manipulated by the upstream processing, collectively represent an optimal control variable that reflect and predict the effects and success of pretreatment for downstream physical separation of floc-pollutant particles. The prime objective of such water purification systems is the removal of pollutant species piggybacked upon floc, which is affected by floc physical characteristics. Because the system 100 quantifies floc physical characteristics, it is pivotal to monitoring and control of pollutant removal. Feedback from system 100 can aid facility operators in performing optimization of the two main control variables, coagulant chemical dosing by a coagulant dosage mechanism 12, and flocculation mixing by a mixing means 15, of a pretreatment processing mechanism.

Processing mechanisms other than clarification 4 and filtration 5 as depicted in FIG. 1, may be employed following coagulation 2 flocculation 3 pretreatment processing. Options may include flotation, various processes based upon gravity, centrifugation, magnetism, or may not employ any intermediate process preceding the final pollutant-water separation process. The separation process may include adsorptive and/or exclusion principles for floc collection including screens, membranes, fabrics, fibers, composites, and granular-media filters. Examples of water processing facilities include municipal drinking water treatment, industrial process water treatment, industrial process wastewater treatment, municipal wastewater treatment, membrane pretreatment (including desalination), recycled water treatment, and advanced wastewater treatment, as well as sludge dewatering, and papermaking or anything similar that can be understood by someone skilled in the art. These processing facilities typically treat thousands if not millions of gallons of water per day for a useful purpose.

The instrument 100 in FIG. 1 can operate in either of two modes: continuous-flow sampling and batch sampling. Continuous-flow sampling is where an upstream fluid is continuously refreshing the fluid sample. Analysis in continuous-flow mode allows the system 100 to repeatedly measure samples at the same point in the treatment process and therefore at the same point in floc-particle maturation or growth. By comparing the results of one sample to a later one collected after a change to the upstream process has occurred, the system 100 can show the change's effect on floc-particle maturation.

Batch sampling is where the fluid sample collected and isolated from the process and therefore has no further mass exchange. The isolated fluid sample should have a volume of less than $\frac{1}{100}$, less than $\frac{1}{1,000}$, less than $\frac{1}{10,000}$, less than $\frac{1}{1,000,000}$ times the volume of it source. Its lower limit is equal to the sample volume 121. Its upper limit is equal to the volume of the vessel the system 100 is monitoring. The fluid sample remains isolated until all desired measurements are completed or an operator releases the fluid. This can occur over an elapsed time of a few seconds to multiple hours depending on what information is desired. The fluid sample is then discarded either to waste or back into the process. Batch sampling provides the ability to capture floc-particle maturation and aggregation of the discrete sample over time and/or floc gravitational settling.

In one embodiment, the system 100 can sense floc particle characteristics. Below, in Table 1, is a list of 13 of these characteristics:

(b) Computed floc particle volume, $V_i$ is defined as the volume of a floc particle. It may be reported in the units of microliters or another suitable unit of volume.

(c) Volume concentration, $V_c$ is defined as the total volume of all particles in a fluid sample divided by the fluid sample volume. It may have the units of milliliters (of particle volume) per liter (of fluid sample volume), or another suitable unit of volume per unit volume (such as parts per million).

(d) Equivalent average spherical diameter, $D_e$ is defined as the diameter of a spherical particle that has the equivalent volume of the average volume per particle of all particles in a fluid sample. It may be reported in millimeters, or in another suitable unit of length.

(e) Gravitational settling velocity, $W_O$ is defined as the vertical component of the velocity of a particle or the average velocity of all particles in a fluid sample, when the particle(s) are being acted upon predominantly by the force of gravity. It may be reported in the units of millimeters per second or another suitable unit of vertical velocity.

(f) Mass density ($\rho_i$), is defined as the mass per unit volume of a floc particle. It may be reported in grams of floc per cubic centimeter of floc, or another suitable unit of mass per unit volume. Note that the units of grams per cubic centimeter are equivalent to specific gravity.

(g) Mass concentration, $M_c$ is defined as the total mass of all particles in a fluid sample per unit volume of liquid. It may be reported in milligrams of floc per liter of water, or another suitable unit of mass per unit volume.

TABLE 1

Metrics for Coagulation-Flocculation-Settling

| Symbol | Units | Name |
|---|---|---|
| | | Foundational Metrics |
| $n_c$ | #/ml | Floc particle count in number of floc particles per milliliter |
| $v_i$ | μl | Computed floc particle volume in microliters |
| $V_c$ | ml/l | Floc volume concentration in milliliters per liter |
| $D_e$ | mm | Equivalent average spherical floc particle diameter in millimeters |
| | | Special Metrics |
| $W_o$ | mm/second | Gravitational settling velocity in millimeters per second |
| $\rho_i$ | g/cc | Mass density in grams of floc mass per cubic centimeter of floc |
| $M_c$ | mg/liter | Mass concentration in milligrams of floc per liter of water |
| | Operational Metrics | for a test of a specific water and coagulant sample or correlation with established standard measurements |
| $F_r$ | ml/l per second | Initial (orthokinetic-perikinetic) increase in floc volume concentration measured in milliliters/liter per second |
| $V_{c,mx}$ | ml/l | Maximum floc volume concentration during test |
| $D_{e,mx}$ | mm | Maximum average spherical floc particle diameter during test |
| $V_{c,s}$ | ml/l per second | Floc volume concentration settling rate after mixer turned off, measured in milliliters/liter per second |
| $V_{c,mn}$ | ml/l | Minimum settled floc volume concentration at end of settling |
| $V_\%$ | % | Ratio of $V_{c,mn}$ divided by $V_{c,mx}$ measured in percent |
| $1/T_e$ | NTU | Reciprocal filter effluent effectiveness measured in Nephelometric Turbidity Units (NTU) |

Here is a definition of the foundational metrics and special metrics in the table above:

(a) Number concentration (or floc particle count), $n_c$ is defined as the total number of particles in the fluid sample divided by the fluid sample volume in milliliters. It may be reported in the units of particles/milliliter or another suitable unit of number per unit volume.

Mass concentration is the average of the mass densities for all floc particles in the sample.

The operational metrics in Table 1 above refer to additional quantitative information that can be derived from an analysis of the data generated from a programmed mixing-settling text protocol by an instrument such as the system and method described with reference to FIGS. 13-25. The information derived from these operational metrics can be of high value for use in plant in managing chemical feed and floc mixing for a water or wastewater treatment plant. Here is a further description of these operational metrics:

(h) The initial (orthokinetic-perikinetic) floc growth rate $F_r$ refers to either the initial linear increase in floc volume concentration $V_c$ or to the maximum slope or rate of increase in $V_c$ values. Since it is a rate of increase in floc volume concentration, it has units of milliliters per liter per second (ml/l per second) or similar. $F_r$ values are a primary indicator of the goodness of coagulant dosing and are extremely helpful in dose control decision making because they are available the earliest in the processing sequence.

(i) Maximum floc volume concentration $V_{c,mx}$ is defined as the maximum value of the suspended floc particle volume concentration during the flocculation phase of a coagulation-flocculation test. It can have the units of milliliters per liter, or another suitable unit of volume per unit volume. $V_{c,mx}$ is the primary indicator of the ultimate rate of waste sludge, an added but long delayed cost, of processing.

(j) Maximum average diameter $D_{e,mx}$ (of a sphere having an equivalent volume to the irregularly shaped floc particle) is defined as the maximum value for $D_e$ during a test, and can be measured in millimeters. $D_{e,mx}$ is a useful early indicator of the subsequent solid settling success.

(k) Floc volume settling rate $V_{c,s}$ is defined as the speed of the rate of floc settling. It is measured by the rate of decrease of $V_c$ per second. It is the slope of $V_c$ during gravitational settling. Since it is a rate of decrease in floc volume concentration, it has units of milliliters per liter per second (ml/l per second) or similar.

(l) Minimum settled floc volume concentration $V_{c,mn}$ is defined as the suspended floc particle concentration after gravitational settling has been completed. It can have the units of milliliters per liter, or another suitable unit of volume per unit volume. $V_{c,mn}$ is a primary indicator or predictor of filter solids loading rate, which in turn is an indirect indicator of process throughput efficiency.

(m) Percent of floc that settled during test $V_{\%}$ is defined as the ratio of $V_{c,mn}$ (minimum settled floc volume concentration) divided by $V_{c,mx}$ is defined as the maximum floc volume concentration). It can be measured as a percentage. $V_{\%}$ is an additional metric that effectively serves to capsulize the overall effectiveness of the coagulant dosing, flocculation, and settling-clarification processing train.

(n) Reciprocal filter effluent $1/T_e$ (also called filtration effectiveness) represents the overall effectiveness (or "integrated goodness") of all of the foregoing processes including coagulation, flocculation, clarification, as well as filtration. It can be measured in Nephelometric Turbidity Units. The reciprocal filter effluent ($1/T_e$) is the de facto regulated standard metric that is used as the surrogate for pathogen removal. Experience and research have shown reciprocal filter effluent ($1/T_e$) to be a reliable metric of pathogen removal effectiveness. To be doubly sure, filtration is then followed by disinfection. The other operational metrics presented here ($F_r$, $V_{c,mx}$, $D_{e,mx}$, $V_{c,s}$, $V_{\%}$, and $V_{c,mn}$) all influence filtration effectiveness ($1/T_e$).

Other potentially measurable or derived floc particle characteristics may include shape factor, reflectivity, porosity, shear resistance, strength, ductility, buoyancy, stickiness, and uniformity.

The reported variable(s) may be for individual particles or they may be expressed as average value(s) for all particles in a fluid sample or distributions. The variable set measured depends upon the environmental conditions where the system is located or upon user requirements. The three possible environments and respective variable sets are:

(i) Mixed—$V_c$, $n_c$, $D_e$
(ii) Settling—$V_c$, $n_c$, $D_e$, $W_O$, $\rho_i$, and $M_c$
(iii) Transitional—$V_c$, $n_c$, $D_e$ Mixed environments prevail in situations where fluid is flowing, such as in a conduit, where air bubbles exist, or when mechanical mixing is imposed, such as a flocculation reactor 14 configured as a full-flow continuous process (FIG. 1). A mixed environment also occurs in a batch reaction mechanism where a discrete volume of a coagulated liquid 13 is continuously mixed over a finite period. Transitional environments occur in situations where the mixing inducing forces have stopped but where non-gravitational forces are still exerted on the floc particle movement. Settling environments result after these, additional forces have dissipated leaving the force of gravity as the predominant force exerted on the floc particles. These various environments exist at different points in the process, in isolated samples, and in coagulate liquids contained in the alternative embodiment discussed in connection with FIG. 6 and other systems described herein.

The system 100 can be mounted at or in any of the environments (see FIG. 1) to sense a set of desired variables. If an operator wished to know only $V_c$, $n_c$, or $D_e$ the particle characterization system could be placed in any mixed or transitional environment location such as at a coagulation influent to flocculation 16A or downstream of a coagulant plug-flow dispersion unit 10PF site 13A-13D. If the operator wished to know $W_O$, $\rho_i$, or $M_c$, the system 100 would have to be placed in a settling environment such as in the clarifier 4 as it is shown in FIG. 1, or in a flocculation mixing vessel 14 or conduit 128 after the mixing means 15 or flow in a conduit 128 has stopped and the fluid has completed the transitional environment stage to a settling environment stage.

Multiple systems 100 may be used simultaneously to provide additional user benefits. For example, systems 100 can be located at any or all the multiple points along the pollutant separation processing train (see FIG. 1). These locations include, but are not limited to:

(a) sampling the raw water 1A, coagulation 2 processing following mixing with the raw water 1 in a coagulant dispersion plug-flow unit 10PG, or other type dispersion unit, and subsequently sampled at any one or all locations including but not limited to:
full-process coagulated effluent stream species A sampling point 13A,
full-process coagulated effluent stream species B sampling point 13B,
full-process coagulated effluent stream species C sampling point 13C, and
full-process coagulated effluent stream species D sampling point 13D respectively, (b) within or following flocculation 3 processing at any or all location including, but not limited to;
near an entrance to floc processing 16A,
near an exit of the initial floc reactor 16B,
near an exit of an intermediate floc reactor 16C,
near an exit of the terminal floc reactor 16D or
in an effluent stream of floc reactor 17A (c) within in or surrounding clarification 4 processing including but not limited to;
    near an influent stream to clarifier 17A,
    within the clarifier (see FIG. 1)
    in an effluent stream from the clarifier 17B, and
    in a clarifier underflow 8
(d) within or surrounding filtration processing including but not limited to;
    in an influent stream to the filter 17B,
    in an effluent stream from the filter 6 and
    in a flow stream from filter backwash 9,
(e) as well as other locations along side-stream flows diverted from any or all location including but not limited to;
    full-process coagulated effluent stream species A sampling point 13A,
    full-process coagulated effluent stream species B sampling point 13B,
    full-process coagulated effluent stream species C sampling point 13C,
    full-process coagulated effluent stream species D sampling point 13D or
    any or all full-flow continuous process observation points 16A-16C or
    any or all sensor observation points 17A-17E, 6, 8, or 9.

Sampling and analysis of these and other location sets produce critical new information for facility operation and control including the pretreatment for floc-pollutant formation success because of the level of addition of each individual coagulant-chemical species; new benefits deriving from this include the ability to:

(i) Systematically monitor the floc formation effectiveness of each individual coagulant species in an additive fashion thereby achieving the elusive goal of full-processing similitude of coagulation chemical manipulation;
(ii) Divert sample streams of each coagulant additive for reconnaissance floc-response mapping off-line of variation of coagulation chemistry and floc mixing at no risk to full-process effluent quality;
(iii) Mass balances reflecting floc-pollutant formation and removal effectiveness;
(iv) Ability to oversee and orchestrate the floc mixing mechanism to tailor individual mixers to contribute to improved removal processing performance;
(v) A range of side-stream empirical testing for mapping floc response to control variable manipulation, for example.

The system 100 can have preprogrammed limits and provide alarm signals if particle characteristics exceed a threshold. Such a warning can be triggered when a particle characteristic rate of change exceeds a predefined rate. Thresholds can be defined by a user or established by the computing engine 111 based on historical data and pattern recognition algorithms. Threshold values could be established based on values of various particle concentration variables, size, apparent particle speed, particle density, or any other measured or derived particle property.

Figure 2:
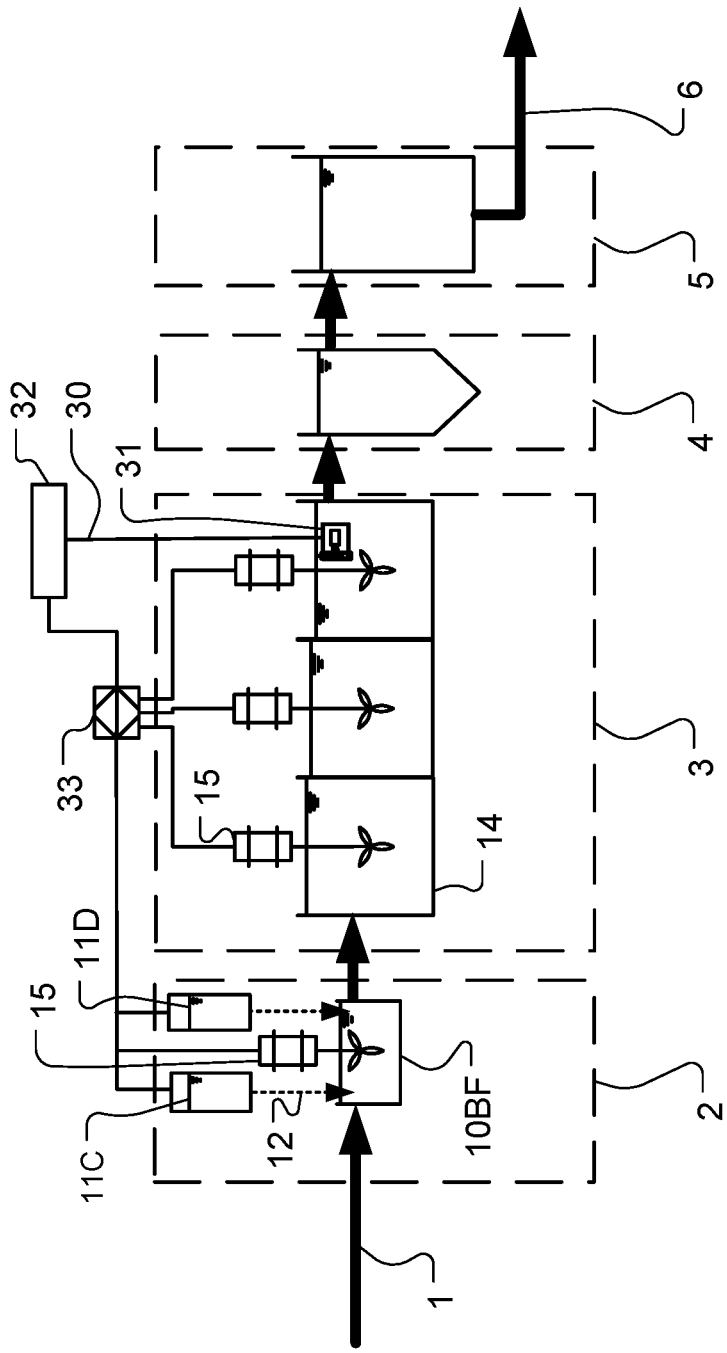
FIG. 2 is a schematic view of a water treatment process with a prior art suspended particle characterization system.

FIG. 2 depicts water treatment system representing the prior art to the system represented in FIG. 1. The related prior art—U.S. Pat. Nos. 4,654,139 and 4,783,269—describes, a floc image pickup means 31, (depicted in a vertical cross section) for an in-situ monitor of floc particles located near the flocculation process exit in water treatment process where it was employed for operational process control. The floc image pickup means 31 was connected by communications and power cable 30 to an image process system 32 that in turn communicated with a controller 33. In U.S. Pat. No. 4,654,139 the floc image pickup means 31 was used for control of the rotational speed of one or more mixer-motors 15 that induce turbulent fluid motion and floc-floc-particle collisions that result in aggregation or suspended floc particle size increase. In U.S. Pat. No. 4,783,269 the floc image pickup means 31 was, instead, employed for control of one or more coagulant chemical species 11C and 11D with the coagulant dosage mechanism 12 with the floc image pickup means 31 also located near the flocculation process exit. Coagulant dispersion was accomplished by employing a back-mix dispersion unit 10BF involving a motor driven variant of the mixing means 15.

Figure 6:
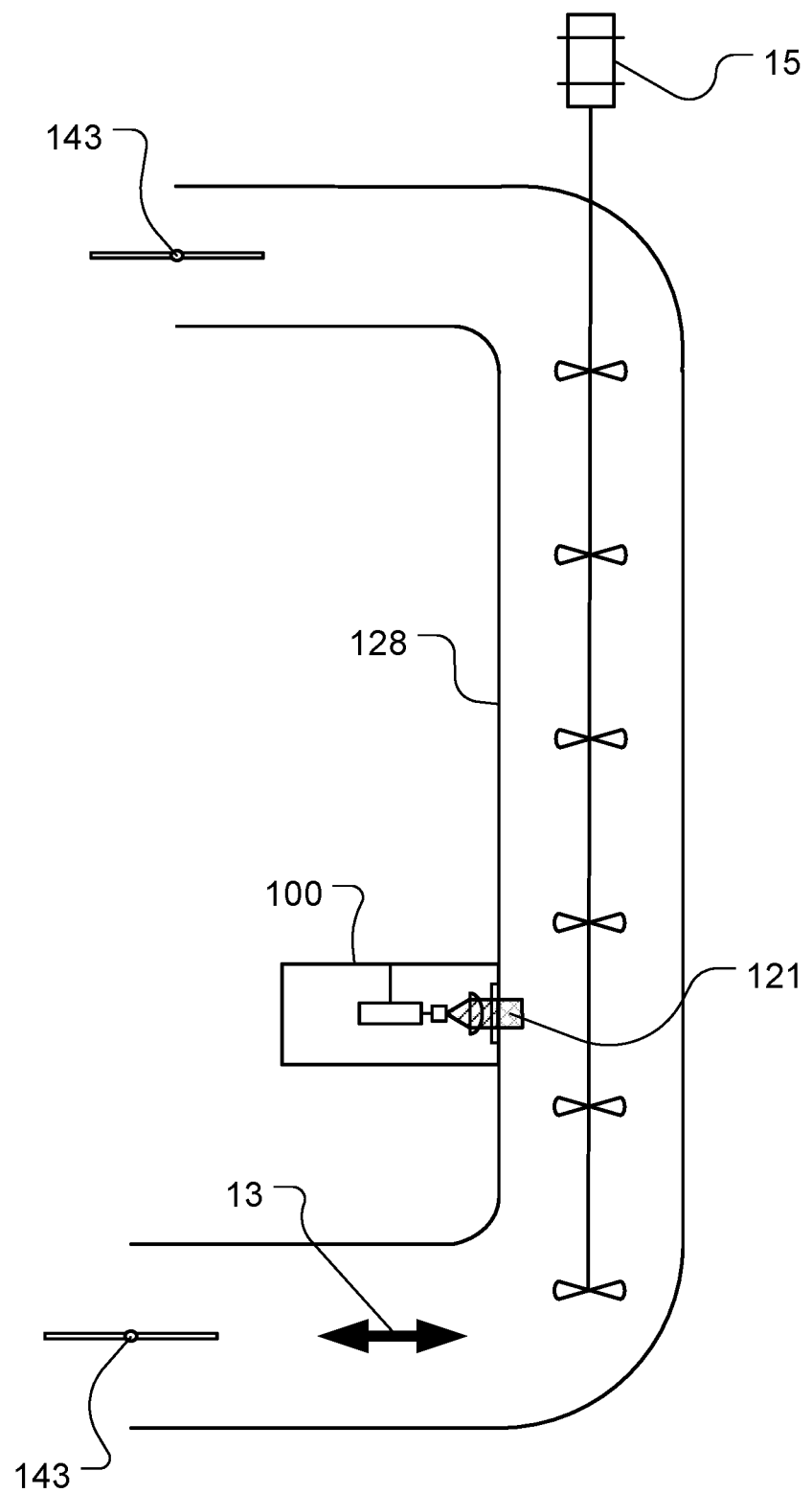
FIG. 6 is a schematic view of a suspended particle characterization system in a side stream of a water treatment facility, the side stream system comprising digital-camera-based instrument for viewing and tracking floc particles in water.

The differences in FIG. 1 and FIG. 2 systems operation further highlight the distinguishing features and limitations of the prior art. The operation of system 100 as depicted in FIGS. 1, 4, and 6 is similar to that of the prior art (FIG. 3) in some respects but differs significantly in others. Both systems remain in place at a fixed location in a constantly flowing environment. Both systems continually analyze floc particle characteristics formed during upstream processing, yet numerous differences exist. First, system 100 utilizes an adaptive volume calculation method selection means to ensure that the most accurate volume approximation calculation is always used for each particle. Second, system 100 can be mounted in multiple environments and virtually any location along the process treatment train whereas the prior systems were limited in placements and therefore limited in their capabilities. Third, the prior art systems had no means of determining mass density ($\rho_i$) or mass concentration. Finally, the system 100 logs and communicates its results to a variety of network types, either new or preexisting in a water-purification-plant environment. In contrast, the prior art devices communicated their results directly to its own slave controller 33 for process manipulation.

Figure 3:
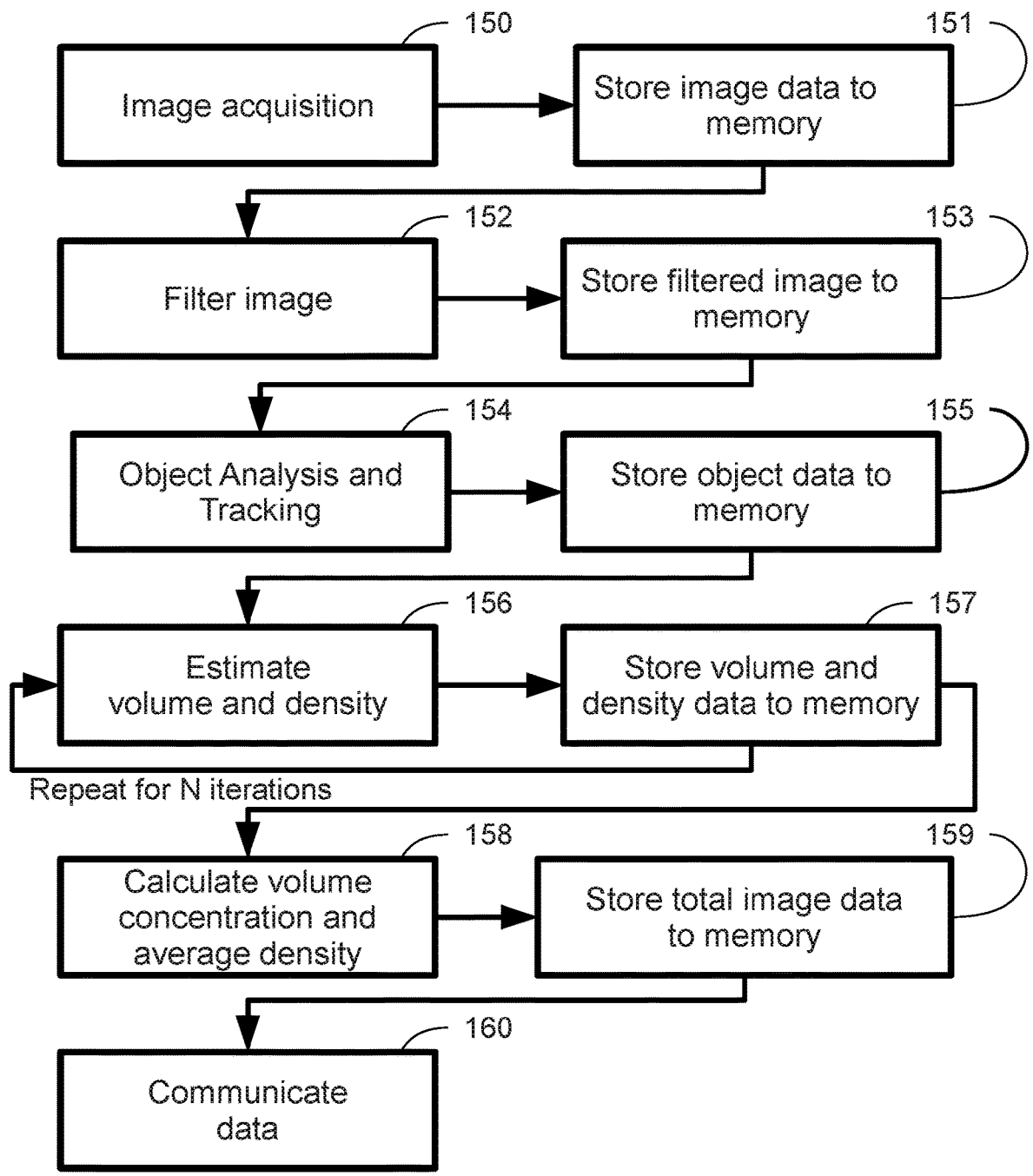
FIG. 3 is a process flow charts for the suspended particle characterization system of FIG. 1.
Figure 4:
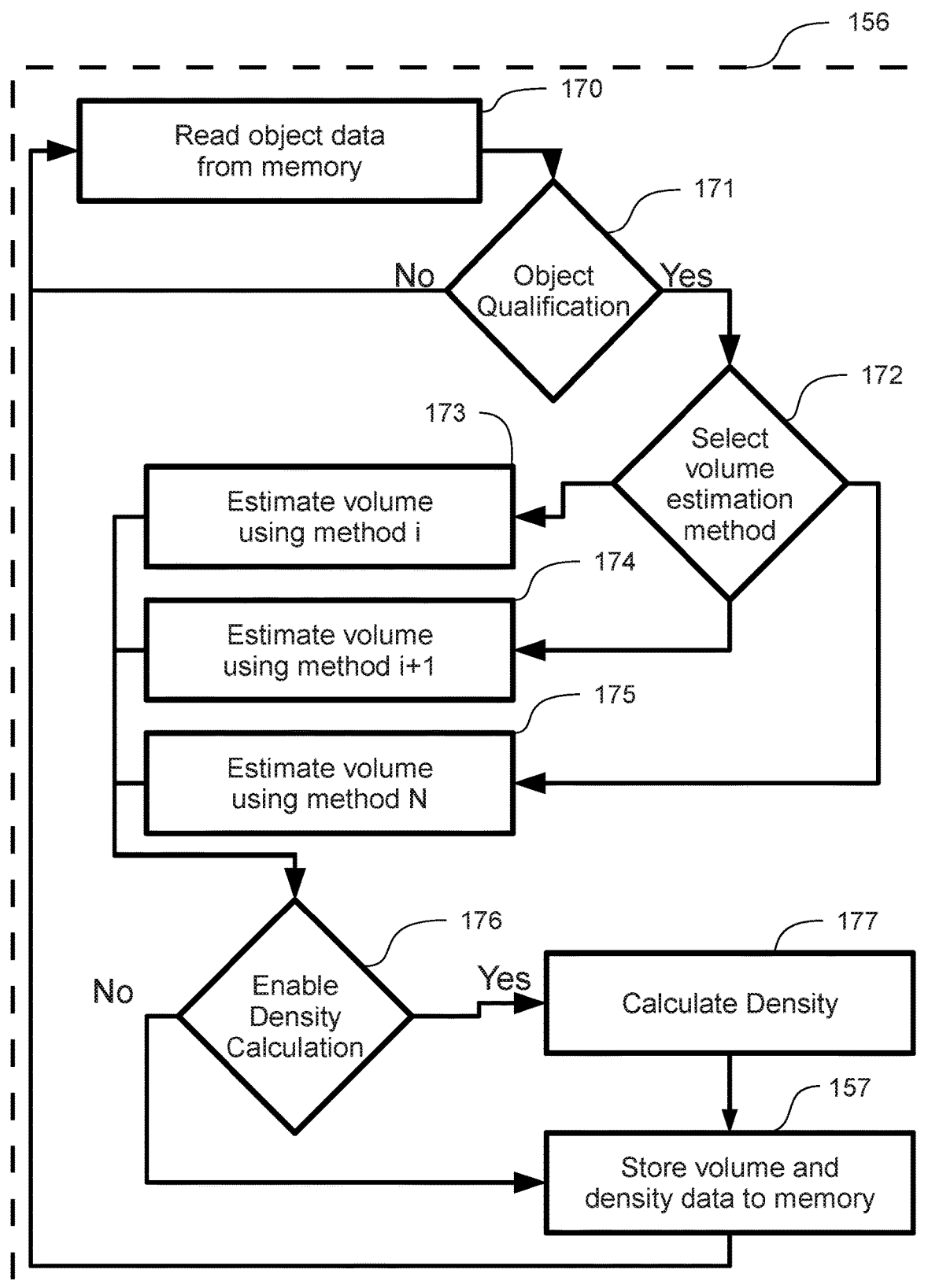
FIG. 4 is a process flow chart for a method for estimating particle volume and density.

FIG. 3 depicts an example of a logic flow used in the system 100 and is described in detail below. The processing reflected in FIG. 3 follows the logic flow through the detailed steps by which the system 100 performs transformation of acquired floc image information from the image sensor 110 into floc particle physical characteristic values— $V_c$, $n_c$, $D_e$, $W_O$, $\rho_i$, and $M_c$, by the computing engine 111 for communication to the process network, communications, and control system 7 (see FIG. 1).

Each image-digitized data set is acquired 150, and stored in memory 151. The image acquisition process may sample a visible area equal to or less than the area visible within the optical view volume 120 by observing only the region of interest 121A. The region of interest 121A can be specified by a human operator or an automatic image control means for neglecting image data that does not contribute or introduces error into otherwise useful measurement of floc characteristics. Examples include a view of a portion of the housing 116, or optical aberrations such as solid matter adhering to the optical window 113. A reduced region of interest may also be useful for the measurement of very small objects, when the object count of the sample volume 121 is sufficiently large to induce slow system performance. The stored image data from 151 is filtered 152 through numerical transformations to enhance image quality by procedures focused around object edge data in the image. The transformations include, but are not limited to, level threshold and adjustments of contrast or brightness. Additional transformations such as a Sobel filter, for edge enhancement, may be used to highlight the apparent edges of particles in the image. The post-filtered image data is stored to memory 153.

The filtered image data is read from memory and object analysis and tracking procedures 154 are performed on the filtered image data. The system performs operations based upon identifying closed object areas to determine if an object qualifies for further processing. If an object violates predefined threshold value of shape factor or size, or is bisected by the border of the region of interest 121A, it is rejected and not considered for subsequent analysis. Qualifying objects are assigned a number based on position, and a total object count is performed for the entire image. For each object the apparent frontal area (A), perimeter (P), and circularity (O) are calculated. Starting with a second image, a comparison is made with previous images that are held in memory to track individual object movement and compute a velocity vector ($W_O$). The data, (object count (N), apparent frontal area (A), perimeter (P), circularity (O), shape factor, object location, ID number, and velocity vector ($W_O$) is subsequently stored in memory 155.

The system estimates the volume and density 156 of each individual detected object. Object data is read from memory 155. Based upon each object's data, such as area, perimeter, circularity, or shape factor, the step 156 identifies an optimal volume estimation method for each individual object and subsequently estimates volume and density (Note, FIG. 4, discussed below, and the related text expounds upon the individual detailed steps involved in executing action 156). Individual object volume ($V_i$) is calculated utilizing the selected method. Additionally, mass density ($\rho_i$) is calculated for all objects with a velocity vector ($W_O$) that is predominantly in the direction of gravitational settling. The estimation of volume and density 156 is repeated for each identified object in each individual frame and the calculated data (individual object volume ($V_i$), gravitational settling velocity ($W_O$), and individual mass density ($\rho_i$) is stored in memory 157 at the end of each processing cycle. This cycle continues until all individual detected objects are processed.

Volume concentration and average density are calculated 158 based on the data previously stored to memory 155, 157. All the individual object volume ($V_i$) values are summed together to create a total objects volume value ($\Sigma V_i$). Dividing the total objects volume value by the sample volume 121 ($V_0$), establishes a ratio of floc object volume to sample area volume, or floc volume concentration ($V_c$). A region of interest correction factor ($ROI_c$) can be used to correct for the usage of a reduced region of interest 121A from the sample volume 121. Average mass density ($\rho_A$) is calculated by dividing the summation of all individual mass density ($\rho_i$) values by the total object count (N). The total image data is stored in memory 159 for long-term storage and is communicated 160 via the cable 117 (see FIG. 1) to the plant process network, communications, and control system 7.

$$V_c = \frac{\sum V_i}{V_o} * ROI_c$$

$$\rho_A = \frac{\sum \rho_i}{N}$$

FIG. 4 depicts a logic flow for the specific sequence of actions that comprise the estimation of volume and density 156 and is described below. The estimation of volume and density 156 computes the individual object volume ($V_i$) and individual mass density ($\rho_i$) values for all objects comprising each image processed. As illustrated, this method involves two conditional decision-making steps, combined with a repeating loop for processing all qualifying objects from each individual 2-D image. Such a process is needed for two reasons. Firstly, the method of volume concentration used in the prior art exceed deviation from known true volume for all other known methods (as documented below in connection with FIG. 5). Alternative methods of volume analysis must be used to minimize deviation or errors in the analysis of irregularly shaped particles such as floc from 2-D images. Secondly, floc particle density is a highly variable characteristic that must be measured to effectively analyze and fully characterize floc for use in coagulation-flocculation control (see FIG. 3).

As depicted in FIG. 4, objects are qualified or rejected for volume estimation by qualifier 171 based on predetermined metrics or adaptive analysis to determine fitness for volume estimation. Numerical criteria for qualification may be based on, but not limited to, circularity (O), apparent frontal area (A), perimeter (P), and shape factor. The object qualification 171 reads the object data from memory 170 to retrieve the data corresponding to the next object in the frame, and then the object data for the qualified object is passed on to be used for the selection of an optimal volume estimation method 172 for processing (continued below). If an object fails to qualify 171, it is not included in any further analysis. Once all objects for a given frame have been analyzed, the volume and density estimation process 156 is complete for a given frame. The image processing then continues with the volume concentration and average density calculation 158 as depicted in FIG. 3.

In reference to FIG. 4, the object data qualified for volume estimation is used to select an optimal volume estimation method 172. The optimal method of volume estimation varies with object shape, necessitating the use of one of a variety of methods to accurately estimate individual object volume ($V_i$). The volume estimation method selection 172 may be based on predefined numerical threshold values, including but not limited to shape, or measures of circularity (O), where (O) is defined as the apparent frontal area to perimeter ratio (A:P), or other parameters based on statistical analysis and pattern recognition algorithms. A variety of volume estimation methods may be considered for the volume estimation method selection 172, as depicted in FIG. 4 by blocks 173, 174 and 175. These methods use data stored in memory to estimate individual object volume ($V_i$). The volume data calculated by one of the volume estimation methods 173, 174 or 175 is stored to memory 157.

Object tracking data previously stored to memory 155 is read by the central processing unit 180 for use in determining if density calculation can be enabled for a given object. The logic for enabling density calculation 176 uses the retrieved object tracking data to determine if an object's movement satisfies predetermined or adaptive, criteria for fitness for density estimation. In a transitional or settling environment the density estimation fitness criteria is based on object motion. Observed motion should demonstrate slow, sinking movement driven dominantly by gravitational forces in to qualify for density estimation. The system can also identify and ignore objects that are attached to the optical window 113 and are impeding or partially fouling the camera view. The system can identify such problematic objects by tracking their position or persistent offsets in pixel brightness or color over a sequence of images. If historical data indicates that an object is not moving, it can be discounted for analysis and characterization. The computing engine can analyze the discounted object image data to determine if they are translucent or opaque. If the discounted objects are opaque, the pixels comprising the object can be fully discounted from image analysis. If pixels are fully discounted from image analysis the computing engine can apply a correction factor to compensate for the change in sample volume due to reduce image pixel count. If the discounted objects are translucent, the computing engine can apply a compensation factor to the affected pixels to offset the apparent fouling. Objects that are partially within the image frame or region of interest can also be identified and ignored. If the system density calculation enable means 176 detects an image captured in a mixing environment, it rejects the object because settling due to gravitational forces does not occur. If an object is rejected for density calculation, all density related processes are skipped and the volume and density estimation calculation 156 will begin for the next object in the frame. If an object is accepted 176 for density calculation, the object data is passed for density calculation 177.

The density calculation 177 step uses each individual objects' volume ($V_i$) and velocity vector ($W_O$) to solve for the force that a settling object exerts on the fluid medium using the Navier-Stokes equation. Fluid medium density ($\rho_f$) and viscosity ($\mu_f$) are assumed as known values unless otherwise determined. The force of the settling object is assumed approximately equal to the weight of the object at the terminal velocity. Individual mass density ($\rho_i$) is then solved for using the object's weight ($F_{weight}$), individual object volume ($V_i$) and known force of gravity (g), by the following the equations:

$$F_{weight} = V_i \rho_f g + 3\sqrt[3]{6}\, \pi^{2/3} \mu_f W_o \sqrt[3]{V}$$

$$\rho_i = \frac{F_{weight}}{V_i g}$$

The individual mass density ($\rho_i$) calculated by the density calculation 177 is stored to memory 157. Following completion of the density calculation 177, data are stored to memory 157, and then the entire cycle of volume and density estimation 156 is repeated for the next object until the last identified object in the frame has been processed and stored to memory 157. Next, image processing continues (refer to FIG. 3) to the volume concentration and average density calculation 158.

Figure 5:
FIG. 5 is a table of 3-dimensional volume estimation methods based on 2-dimensional images.

FIG. 5 lists different methods for volume calculation and their accuracy. This volume estimation methods table 200 summarizes the average results of calculated volume divided by actual volume. That average, expressed as a percentage, for the five different methods of volume estimation (columns) performed across nine differently shaped sample objects (rows) is calculated such that a value of 100 represents a perfect approximation of each objects known volume. The nine different sample objects were created by a 3-D modeling application allowing the actual object volume to be explicitly known. Images of the sample objects were acquired and analyzed by a process similar to FIG. 3. The numerical results tabulated in FIG. 5 were computed utilizing the five volume estimation methods (heading each column and enumerated below) where each object was rotated along multiple random axes. The volume approximation methods investigated, can be separated into two groups based on the number of geometric properties employed; the groups being methods that use only one property, and methods that use more than one property. Geometric properties are directly observable and include centroid, area, circularity, position, and perimeter. Centroid is the intersection of all strait lines that divide an object into two parts of equal moment and is known as a geometric center, or barycenter. Area is the apparent frontal area of an object as observed by the image sensor 110. It may also represent the apparent area of the object as witnessed by a different point of reference. Circularity is a numerical quantity representing the degree to which an object is compact. Measures of circularity used may include shape factor, circularity ratio, fractal dimension, or sphericity. Position is the location of an object in relation to a point of reference. Perimeter is the length that surrounds an area of an object. The numerical values in FIG. 5 are the average of a sample set comprised of all witnessed object orientations for each particle shape (rows) and each method (columns).

FIG. 5 (Column A) Circumscribed: The circumscribing circle method approximates the apparent frontal area of an object by finding the smallest circle that can entirely enclose the object. The diameter of the circle is used to calculate the individual object volume ($V_i$) of an equivalently sized sphere, as defined by:

$$V_i = \frac{4}{3}\pi r^3$$

where r is the radius. Similar to this method is the inscribed circle method that approximates an object area by finding the smallest circle that can be enclosed by the object. An inherent flaw of both methods is they do not account for porosity or other measures of object irregularity. Either method uses only a single geometric property in its calculation. Because of the assumption of a near spherical object geometry, the circumscribed method will always be erroneously large while inscribed will always report too small.

FIG. 5 (Column B) Heywood: The Heywood, or equivalent area circle, volume estimation method is based solely upon the apparent frontal area from a particle. The volume of a sphere with equal apparent frontal area to the object is calculated and assumed equivalent to the volume of the observed particle. The output of this method is independent of changes in particle porosity and uses only a single geometric property in its calculation. In this method, the individual object volume ($V_i$) is defined by:

$$V_i = \frac{4}{3}\pi\left(\frac{2A}{\pi}\right)^{\frac{3}{2}}$$

FIG. 5 (Column C) Pappus: A method for estimating the volume of observed particles based on two geometric properties in its calculation is employed based on Pappus's theorem. In this case, the volume is found by bisecting the observed object through its centroid such that the bisection results in two halves of equal area (A/2). One half is selected and its geometric centroid (X) is calculated. The individual object volume ($V_i$) is defined by:

$$V_i = \pi A X$$

FIG. 5 (Column D) Hydraulic: The hydraulic volume estimation method is dependent on two geometric properties in its calculation, the observed particle's apparent frontal area (A) and perimeter (P), and is consequently sensitive to particle porosity. The hydraulic volume is derived from the manning formula, which commonly is used in flow-based calculations. Particles with higher porosity will result in a lower volume estimation output from this method. Conversely, lower porosity will result in a higher volume estimation output for a given area. The individual object volume ($V_i$) is defined by:

$$V_i = \frac{4}{3}\pi\left(\frac{A}{P}\right)^3$$

FIG. 5 (Column E) Heywood-Hydraulic: The Heywood-Hydraulic volume estimation method calculates the average of the output of the two individual methods. This method was developed here because it was reasoned that the hydraulic method is sensitive to porosity and the Heywood method is not, the combination of the two methods often outputs a value that is significantly closer to the true volume of the observed particle. This method also requires two geometric properties in its calculation and demonstrates consistent accuracy.

Floc particles are often highly irregular three-dimensional shapes and thus, the apparent frontal area of a particle can vary significantly depending on the orientation of the particle from one observation to the next. This was evident throughout the simulation across all shapes (rows) and methods (columns) tributary to the values (averages) tabulated in FIG. 5. To more accurately estimate particle volume based upon 2-D imaging, embodiments of the present invention can take particle image data from multiple observations as a given particle moves and changes orientation within the suspending fluid medium. Embodiments of the present invention can use at least 3 samples, at least 5 samples, at least 10 samples, at least 25 samples, at least 50 samples, at least 100 samples, and at least 200 samples.

The analysis reflected in FIG. 5 lead to important conclusions regarding computing particle volume based upon 2-D imaging:

First, though the Heywood-hydraulic method generally results in the closest approximation of true volume (8 of 9) this is not the case for all shapes examined. FIG. 5 (row VI) shows the results of an object where the Pappus method provides a closer approximation than the other methods. This demonstrates the need for a volume estimation methodology to be adaptive and capable of selecting the most appropriate method for consistently achieving the most valid volume estimating method.

Second, the results also demonstrate that methods using only a single geometric property are insufficient for producing accurate approximations. Therefore, methods using fewer than two geometric properties in their calculation, such as the circumscribed and Heywood methods, can be explicitly excluded from the system.

Third, to achieve improved particle volume estimation results, multiple images need to be analyzed.

FIG. 6 depicts an embodiment for deployment of system 100 attached to a conduit 128, combined with valves 143, and with a mixing means 15. If the coagulated liquid 13 is turbulently mixed while in batch sample mode, floc-particle characteristics can be analyzed against variables such as mixing time, and mixing intensity. Settling conditions can occur if the mixing is stopped allowing for measurements related to gravitational settling to be taken and analyzed.

Figure 7:
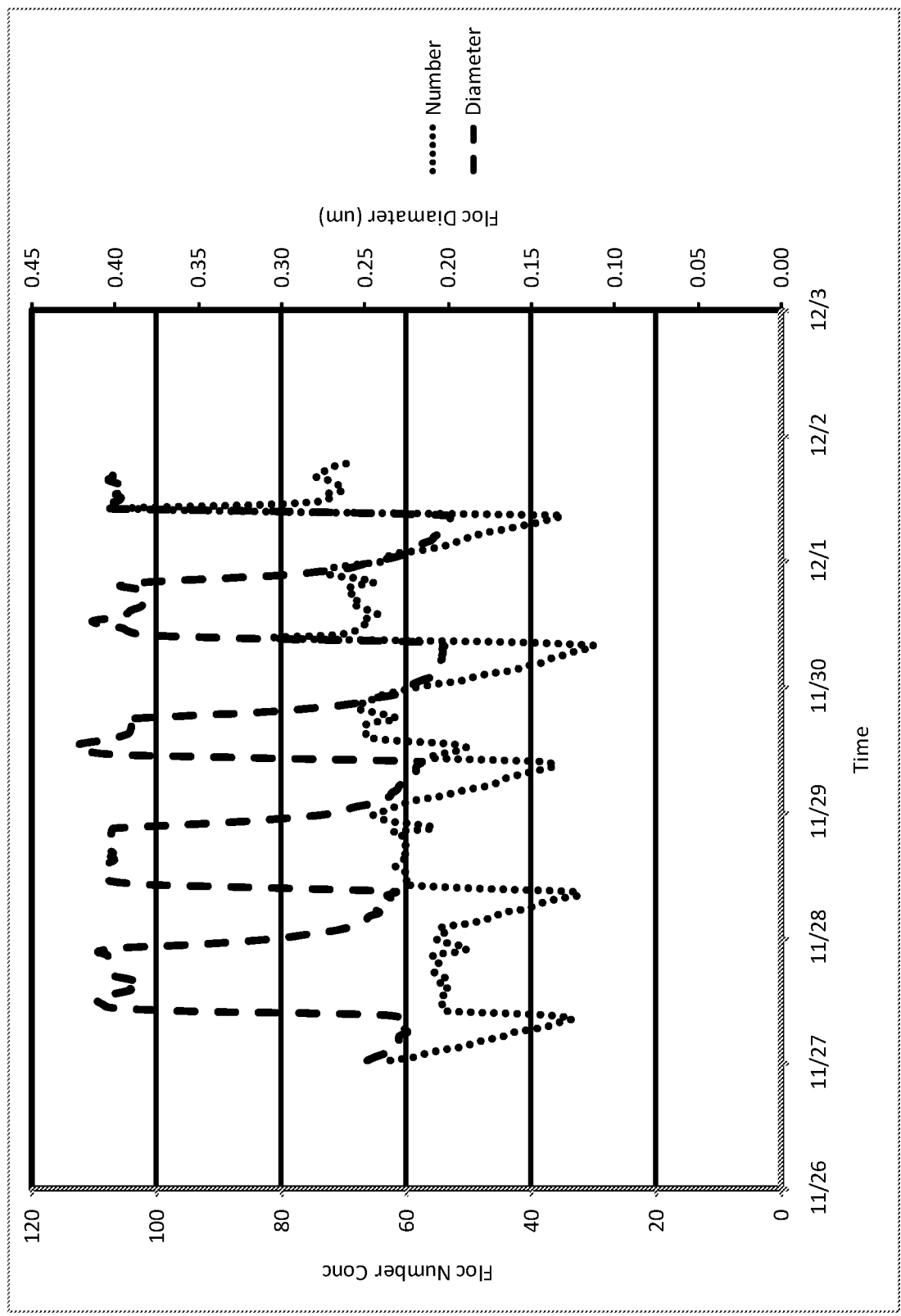
FIG. 7 is a graph showing a diurnal cycle of floc number concentration and floc diameter in a typical water treatment facility.

FIG. 7 is a graphic representation of floc-particle analysis results from an operating water treatment plant demonstrating the significance of floc-particle mass density. FIG. 7 is constructed from floc particle analysis at a conventional coagulation-flocculation-plate-settler-filtration plant using a development system similar to system 100 located near the floc tank exit. The graph reflects a repeated diurnal pattern over 4.5-day period showing that floc particle diameter and particle count both decrease by ~½ from daytime to nighttime operation.

During testing, the plant operated as a normal facility during the daytime, during which raw water is coagulated-flocculated-settled and filtered at a constant continuous flow rate through the floc chamber and the entire treatment process. The daytime operation is continuous flow through three mechanically mixed floc reactor basins separated by baffle plates. At nighttime, only the flocculation-stir motors ran; no newly coagulated water inflows into the floc chambers, and no product flows from the floc reactor to the plate settlers. Effectively, the nighttime operation is batch floc processing being performed on a large sample of water formed by continuous-flow coagulation-flocculation processing. The total floc-particle mass remained constant during this period.

A reduction in floc diameter at night, presumably by breakup, should lead to an increase in particle count if mass density were assumed constant. FIG. 7 demonstrates an opposite trend meaning mass density of the particle must be changing to preserve total system mass in addition to or instead of breakup.

Floc mass density change is the most logical alternative to the prospect of floc breakup. If one combines reactor theory with the assumption that the floc reactor design details and actual operation performance of this facility may be less than ideal, it can lead to the following scenario. This batch-mode reaction approaches an ideal processing scenario where all floc experience similar mixing induced fluid-shear history. Consequently, a more uniform tightly packed particle distribution develops over time. To the contrary, the daytime continuous flow-mode processing, combined with the necessity that mixing is mild (far short of the ideal situation of a completely mixed tank reactor) introduces opportunities for fluid short-circuiting (read, increased number concentration of small floc resulting from shorter residence time and fewer floc-floc collision opportunities). This mild mixing, which is necessary to avoid floc shear, also provides ample opportunities for dead zones, especially in rectangular reactors, that can lead to the formation of very large loosely-packed floc. The net result of such non-ideal continuous-flow processing as described above lends qualitative support for the trends showing high number concentrations and with both smaller and larger size floc and reduced mass density.

The implications of FIG. 7 are:

(a) Two variables of floc particle characteristics, diameter and count, are inadequate to account for physical characteristic variation of floc particles, e.g., by >100%; and (b) Knowing floc-particle mass density is essential to fully characterize floc formation in water-separation processing.

Figure 8:
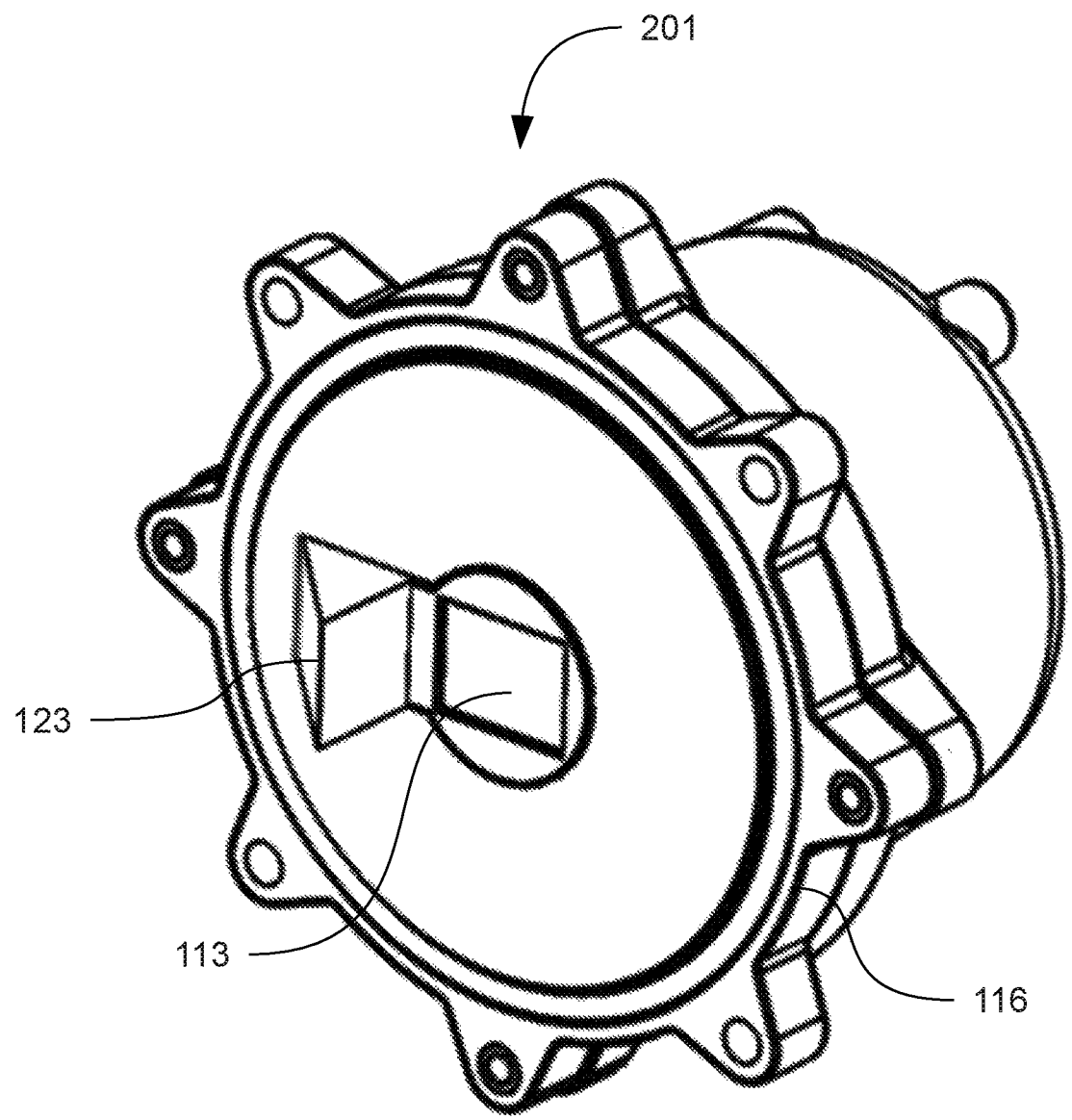
FIG. 8 is an isometric view of one embodiment of a digital-camera-based instrument for viewing and tracking floc particles in water (also known as a suspended particle characterization system), that could be used in systems such as the one illustrated in FIG. 6.

FIG. 8 is a three-dimensional rendering of the system 100 that was referred to in previous figures. The rendering 201 is an isometric view of the system 100. External elements can be seen here. Such elements include the prism 123, window 113 installed in housing 116. This view is provided to aid in further understanding the construction of the system 100. This illustrates the minimal obstructions surrounding the sensing face and the convenience for alternative placement in-situ or for mounting to a vessel 127 or conduit 128 wall.

Figure 9:
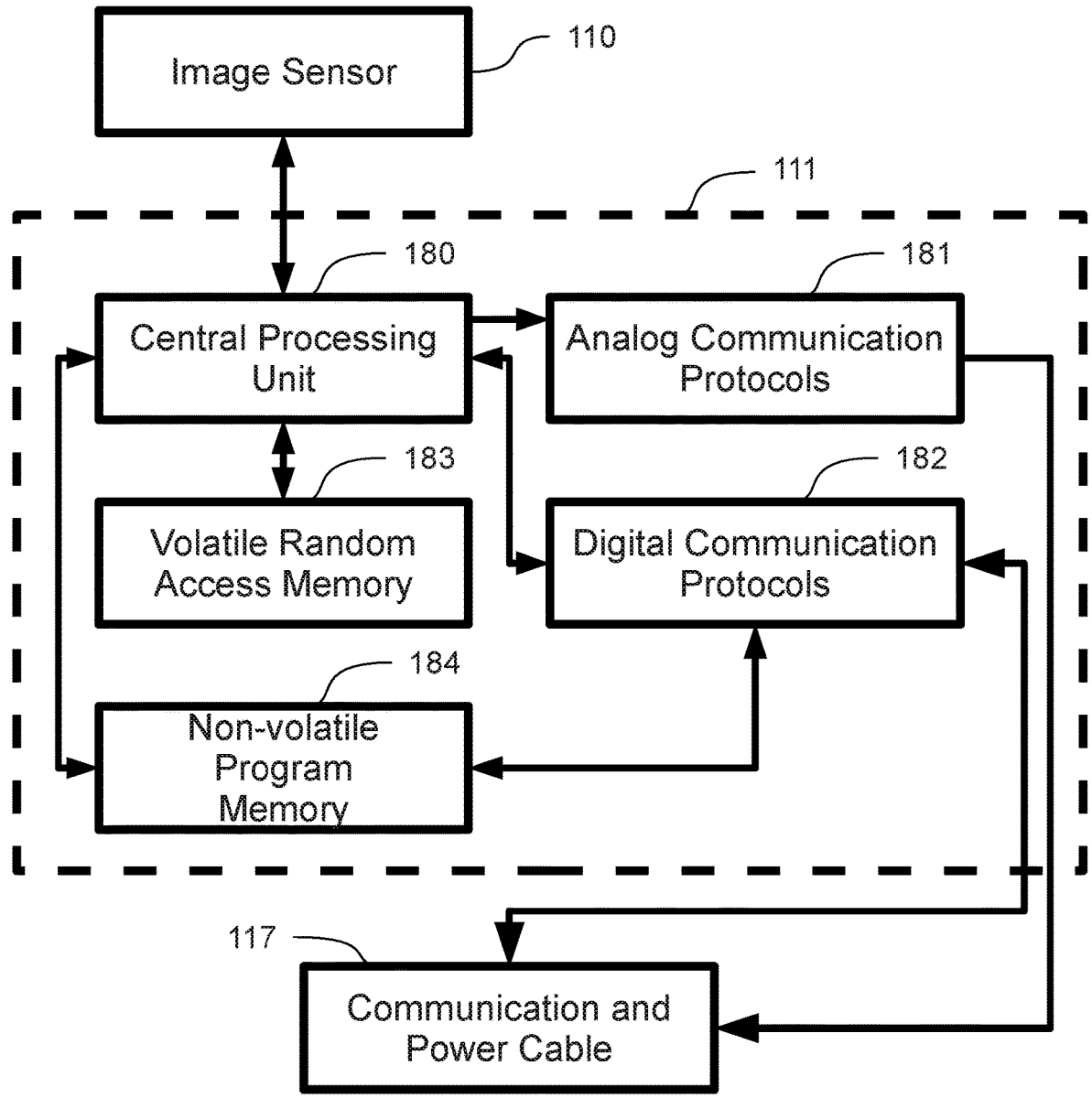
FIG. 9 is a block diagram of a computing engine for a particle characterization system.

FIG. 9 depicts a system diagram of the computing engine of system 100. The central processing unit 180 is comprised of an electronic circuit that can execute computer programs. The central processing unit 180 can be any application specific integrated circuit, microcontroller, general-purpose microprocessor, field programmable gate array, or similar device understood by someone skilled in the art. The central processing unit 180 reads and executes computer programs stored in non-volatile program memory 184. The non-volatile program memory 184 can consist of, but is not limited to electrically erasable programmable read-only memory, magneto resistive random-access memory, or flash memory. The non-volatile program memory 184 stores the computer program data that is used by system 100 to perform all major logic and communication functions, and can be used to archive measurement data and system configuration data. The non-volatile program memory 184 can retain the stored data when the system is not powered. The data stored on the non-volatile program memory 184 can be remotely accessed and modified via digital communication protocols 182 to upgrade system software or otherwise alter system behavior. Digital communication protocols 182 can include but are not limited to TCP/IP, RS-232, USB, or wireless protocols such as IEEE 802.11 and Bluetooth. The non-volatile program memory 184 can be remotely accessed through digital communication protocols 182 directly, or through the central processing unit 180 as an intermediate device in a data-link layer.

During normal system operation, the central processing unit 180 receives image data from the image sensor 110, as discussed in the description of FIG. 3. The central processing unit 180 uses the volatile random-access memory 183 for short term of data such as images, programs, and particle measurements. The data stored on volatile random-access memory 183 is only retained when the system is powered on. The volatile random-access memory 183 can consist of: but is not limited to dynamic random-access memory or static random-access memory. The volatile random-access memory 183 may be physically integrated with the central processing unit 180 hardware.

The central processing unit 180 can output data to analog communication protocols 181 though digital to analog conversion hardware. Analog communication protocols 181 can be used to communicate with external devices, such as SCADA networks, programmable logic controllers, data loggers, and alarms. Analog communication protocols 181 can include but are not limited to current loop signals, voltage signals, and frequency or amplitude modulation signals.

Figure 10:
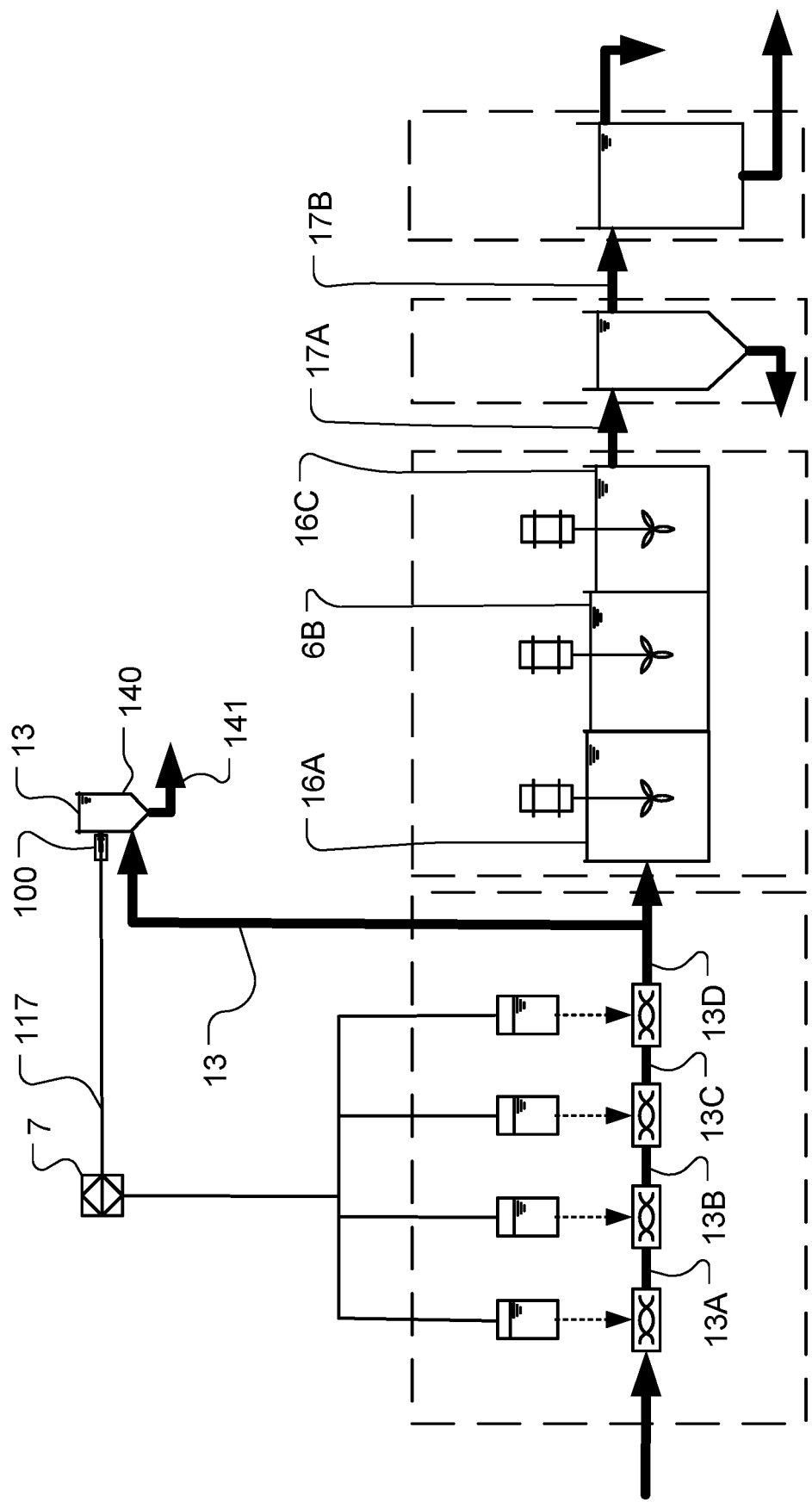
FIG. 10 is a schematic view of a suspended particle characterization system deployed in a side-stream location.

FIG. 10 depicts a water treatment processing system similar to FIG. 1. The two water treatment systems differ in the deployment of system 100. The differences give rise to major changes in the information collected for characterizing, optimizing, and control of each specific water treatment processing system. More significantly, it changes information tendered to plant operators thereby enabling proactive process optimization and control at a manageable level of risk to full-process performance.

In the case of FIG. 1 all the information collected by the system 100 is tied to the time, chemical, and physical domains of the full-processing system because changes in coagulant dosage must first propagate through the full-processing system before they can be detected and measured to aid in control decisions.

In the case of FIG. 10 however, all the information collected by the system 100 is effectively independent of the time, chemical, and physical domains of the full-processing system, if the system is operated as described below. This means that all three domains can be explored, reconnoitered, and mapped without risk to the quality of the full process product water. This empirical information can provide a broader range of information for plant operators to make decisions in the operation of the full process. Since this system is side-stream and independent of the time domain of the full process, it can be exploited as a pilot system, with the inherent low risk to full-process quality, while simultaneously achieving:

(i) Near real-time, ad hoc feedback for process optimization and control.
(ii) Freedom to reconnoiter operationally-controllable-variable-floc response empirically, ad hoc with exacting coagulation-chemical similitude.
(iii) Employing a near ideal surrogate variable reflecting pollutant removal success.

The embodiment depicted in FIG. 10 collects coagulated liquid 13 downstream of coagulant addition points and uses the system 100 to analyze the samples. This configuration reduces the risk of compromising full-process-effluent quality. The combined system consists of a batch sample mode side-stream reactor 140, similar to FIG. 6 system, with an attached system 100, an input control mechanism that receives freshly coagulated full-process stream samples 13, a sample discharge control valve, and a fresh water spray system for reactor cleaning and preparation. The attached system 100 measures particle characteristics as discussed in the description of FIG. 3 and FIG. 4. This includes either floc formation data set $V_c$, $n_c$, and $D_e$ during mixing, or intermittent data sets of $V_c$, $n_c$, $D_e$, $W_O$, $\rho_i$, and $M_c$ available follow cessation of mixing. The data output of the system 100 can be used by external hardware to drive a control system for the optimization and control of full process coagulation dosage and mixing motor behavior. Such a control system can be used for all routine testing including the initial operation performed at startup for a new site for local optimization. The samples can be taken from any point downstream of coagulant addition, such as but not limited to 13A, 13B, 13C, 13D or 16A-16C. The side-stream coagulation-flocculation optimization system can be used to measure the coagulation-flocculation process feedback response on a shorter time scale than the mainstream of the treatment facility, allowing for more effective optimization and control of the treatment process.

The operation of the side-stream coagulation-flocculation optimization system is a serial process involving multiple steps. First, the sample of coagulated liquid 13 is collected in reactor 140, manually or using valves, sprays, or other fluid control means 13. The sample is then processed through mixing-flocculation by application of a mixing means. Floc growth is monitored by the system 100, as discussed in the description of FIG. 3 and FIG. 4. The mixing can be temporarily stopped on demand to allow for particle gravitational settling for the measurement of particle density, as discussed in the description of FIG. 4. Finally, when a sample processing cycle is complete the sample is purged by sample to waste 141 means and the reactor is cleaned and prepared for next sample cycle. Subsequently, full-process coagulation 2 mechanism can be used for a brief interval, sufficient to prepare, to divert, and to fill reactor 140 with another exploratory sample, and thence return full-process chemical coagulation to 'normal' settings. An exploratory sample is prepared by either raising or lowering the full-process dosage of one coagulant chemical species, one at a time, say +/−<10% of the current set point dosage value, for only a brief time period but sufficiently long as defined above. Said reconnaissance sample is then analyzed off-stream of the full process for floc response mapping. This methodology can be repeated as necessary to define the local optimum, or charge neutral, coagulation chemistry set point value. This same methodology can also be used to explicitly quantify if the raw water coagulant demand has changed.

One characteristic of the system depicted in FIG. 10 that must be noted concerns the inability of this or virtually any side-stream system to simulate the physical domain of the full-process system. This approximation cannot be accomplished especially in a practical fashion. However, this limitation is of no significant consequence with respect to facility operation and control. This obtains because of two realities; the chemical and physical domains of coagulation-flocculation-removal processing are nominally independent of each other, and the leverage ratio—for an operator to control pollutant-removal success—is of the order of $10^5:1$ [chemical:physical]. This is to say, if the coagulation chemistry is significantly off optimum, pollutant removal will likely be mediocre at best. Off-optimum operation normally poses limited human health risk because drinking water is also typically disinfected with chlorine following filtration. Chlorination effectively kills virtually all infections organisms, except for *Cryptosporidium parvum*. *Cryptosporidium*, though found to be virtually omnipresent in surface water, is rarely present in significant concentrations, in which cases off-optimum coagulation is nominally sufficient to remove most *Cryptosporidium* at 1.5-log removal. However, in the case of high raw water levels such as the drinking water disaster in Milwaukee, Wis. in 1993, off optimum coagulation, as was apparently the case, results in catastrophic failure. To the contrary, optimum coagulation chemistry, as has been demonstrated, yields near-quantitative removal of *cryptosporidium* and Giardia, and therefore may be required in cases such as Milwaukee. Recently, drinking water facilities have begun adding expensive processes, such as UV disinfection, which effectively kills *cryptosporidium*, or replacing granular-media filters with membrane filters. A much less expensive alternative for the worlds' infrastructure of coagulation-granular filtration systems is to employ effective metric based control systems in order to reliably optimize coagulation chemistry—thereby achieving the removal performance potential (e.g., ~5-log removal vs. 1.5-log removal) of such systems, as may be the case for the Partnership Level IV class of facility operation.

Alternative embodiments of the side-stream system (FIG. 10) include but are not limited to the following or anything similar that can be understood by someone skilled in the art including:
a) A multi-train full processing system with a dedicated coagulation 2 mechanism. Such a system may be employed for wide ranging chemical and physical response testing in cases where the product water can be diverted from blending with the full-process product stream.
b) Side-stream system receiving raw water 1 with a dedicated coagulation 2 mechanism, and batch process as depicted in FIG. 10. Alternatively, a continuous-flow mechanism can be deployed involving flocculation 3 with or without separation process units involving any of the known separation processing units including membranes. Such systems have the added advantage that either global or universe optimization can be exercised with zero risk to the full-process effluent quality performance.

Figure 11:
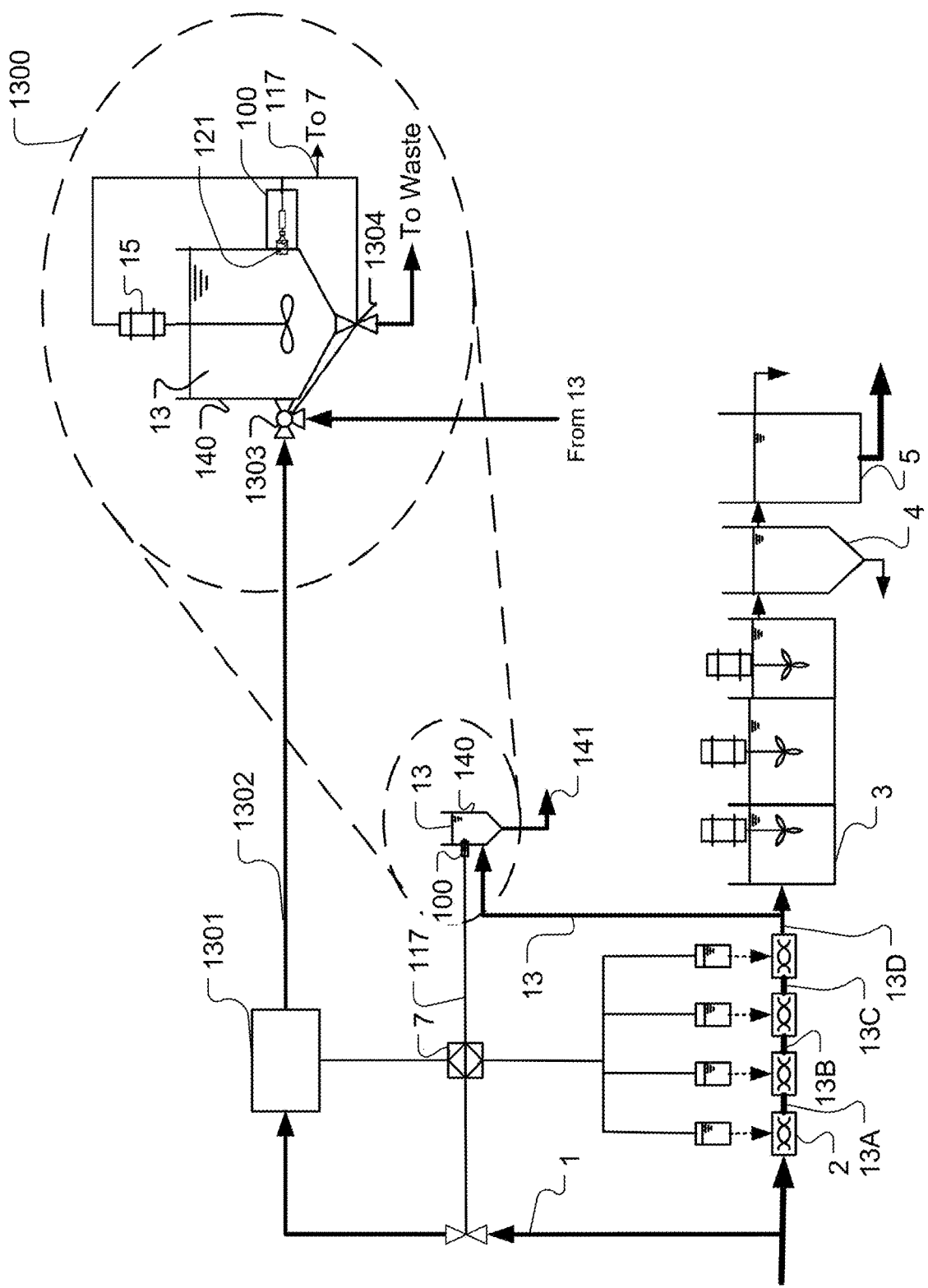
FIG. 11 is a schematic view of a coagulant chemical test simulation system in an alternate deployment in a water treatment process.
Figure 12:
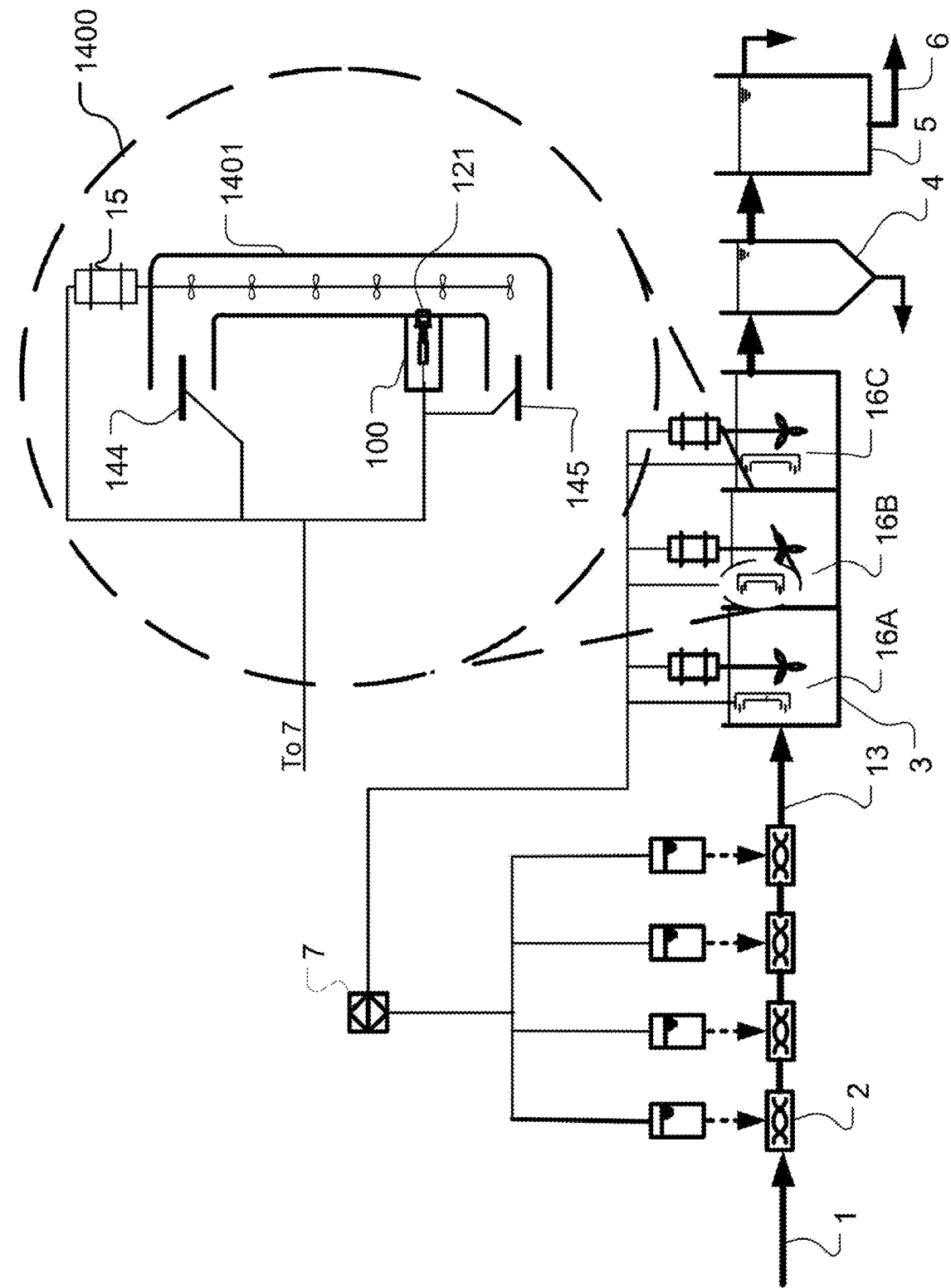
FIG. 12 is a schematic view of a flocculation performance analysis system of FIG. 6 in an alternate deployment in a water treatment process.

Coagulation and flocculation are sequential and distinct process steps in water purification and are independently controllable and inseparably coupled in that coagulation triggers flocculation (also known as aggregation). For process control and management purposes it is necessary to empirically test the coagulation effect at a small scale and cost. It is extremely difficult to simulate full-process conditions of both coagulation and flocculation at a scale factor of 1/500 or smaller. These three features (independence/interdependence, empirical testing, and the difficulty of small-scale process simulation) create challenges in dissecting, understanding, quantifying, and effectively managing the coagulation-flocculation process in water purification systems. FIG. 11 and FIG. 12 depict two variants of a water sample isolation analysis system, shown at 1300 and 1400, to address these challenges. These variants of the isolation system 1300 and 1400 can isolate a water sample from full-process turbulent mixing.

Referring to FIG. 11 and FIG. 12, the two embodiments of the isolation system 1300 and 1400 include an outlet valve, shown at 145, at the bottom of a chamber, shown at 1301 in FIG. 11, and 1401 in FIG. 12, that holds the water sample. The chamber 1301 or 1401 is typically comprised of a vertical tube section with an inlet near its top and an outlet near its bottom, but can be any functionally equivalent shape or size capable of holding the water sample and capable of being understood by anyone skilled in the art. When the inlet and outlet valves 144 and 145 are closed, the isolation system 1300 or 1400 isolates the water sample from the full-process turbulent mixing. The isolation system 1300 or 1400 can be equipped with a controlled mixing means, shown at 15. The isolation system 1300 or 1400 includes an optical sensor, shown at 100, that analyzes the water sample. The sensor 100 views a sample volume 121 that protrudes into the chamber 1301 or 1401, creating an obstruction-free vertical settling pathway for analyzing floc particle settling and density. The sensor 100 is attached to a substantially vertical wall of the chamber 1301 or 1401 and is positioned so that the lower boundary of the sample volume 121 is at least 10% above the bottom of the chamber and the upper boundary of the sample volume 121 is no higher than 50% above the bottom of the chamber, the 10% and 50% being measured vertically based on the outlet valve 145 being the bottom of the chamber and the higher of the inlet valve 144 or the level (water/gas interface) to which the chamber is normally filled being the top of the chamber. Floc particle characteristics analyzed by the sensor system 100 may include: volume concentration, number concentration, gravitational settling velocity, mass density, mass concentration, computed particle volume, and synthetic diameter (equivalent diameter of a spherical particle of the same volume) or any other characteristic or characteristics described in this disclosure or capable of being understood by anyone skilled in the art By having valves 144 and 145 and a mixer 15, the isolation analysis system 1300 can operate in multiple modes for characterizing floc particles including:
a) Valves open and mixer turned off, allowing samples to be analyzed "as is".
b) Valves closed and mixer turned on, allowing batch-mode flocculation analysis of floc characteristics changes over time.
c) Valves closed and mixer turned off, providing quiescent conditions for measuring floc-particle gravitational settling and computation of density.

Further referring to FIG. 11 and FIG. 12, embodiments of the present invention can include a controller, shown at 7. The controller 7 may include a processor and software. The controller may be coupled to the optical sensor 100, the mixer 15, and/or the valves 144 and 145. Power and communication may be supplied by cabling connected to and coordinated with the overall plant operation through a plant process network. Control signals may be communicated wirelessly. It should be noted that the mixer 15 could be controlled by the controller 7 in response to a signal from the optical sensor 100. This control of the mixer 15 can include turning the mixer on or off, changing the mixing speed (or power input to the mixer), changing the duty cycle of the mixer (% of time the mixer is on or off). For example, the optical sensor 100 may be used to determine a characteristic of the floc particles in the chamber and this characteristic may be used to determine that there has been sufficient progress in the mixing process that the mixer 15 should be turned off to establish the quiescent conditions needed to determine particle settling velocity. For laminar flow, particle density can be determined from particle settling velocity, particle size, the density of water, and the viscosity of water using Stokes Law.

FIG. 11 depicts a flocculation analysis system 1300 located in a side stream. This side-stream system 1300 of FIG. 11 possesses features enumerated previously as well as additional features and capabilities for measuring, quantifying, and monitoring floc characteristic changes as a function of coagulant dosing, mixing time, or mixing intensity, independent of the full-process system. The flocculation analysis system 1300 can be used for empirical reconnaissance testing and mapping of coagulation effect and goodness. One advantage of such a side-stream system is that it can perform the task of empirical testing of coagulation and flocculation independently of the full process. A second advantage is that empirical testing can be done at low risk because processed samples are discharged "To Waste" 141 instead of back to the process. If empirical coagulant-dose testing was done using the full process directly, there is an unacceptably high risk that the quality of the full-process effluent 6 will be compromised. A third advantage of this system is that the water sample in chamber 1301 can precisely simulate the coagulation effect that would occur in the full process. A fourth advantage of the flocculation analysis system 1300 is that it responds much faster to changes in coagulant dosing than the full process.

Referring to FIG. 11, the water sample isolation analysis system 1300 is equipped with means of selectively receiving a water sample either from a point downstream of a chemical addition point, shown at 13, or from a point downstream of simulation coagulation system, shown at 1302, through an inlet valve or valves, shown at 144. System 1300 as shown in FIG. 11 can empirically test goodness of prepared water samples in a water treatment plant for the effects of coagulant dosing. The samples may be prepared, acquired, and delivered in one of the following ways:

a) Samples can be prepared in the full process, acquired from a point downstream of a chemical addition point, shown at 13, and delivered through a pipe and a valve 144 into the chamber 1301.
b) Samples can be prepared in the full process, manually acquired from a point downstream of a chemical addition point 13, and manually delivered to the chamber 1301, accomplishing the identical result as (i) above.
c) Samples can be prepared by adding coagulant in a simulation coagulation system, shown at 1302, and either manually delivered or delivered through a pipe and valve 144 to the chamber 1301. This alternative can be employed to evaluate coagulant species different from those used in the full process without imposing risk to the full process operation. Using this approach leaves some uncertainty that there are differences in coagulant dispersion from the full-scale system.
d) Samples can be prepared, acquired and delivered using other similar processes capable of being understood by anyone skilled in the art, either manually or using a controller, such as that shown at 7.

The optimal coagulant dosage for the system 1300 as shown in FIG. 11 can be determined using the following protocol:

1. Transfer sample of full-process coagulant effluent downstream from a coagulant addition point 13 to the chamber 1301, activate controlled mixing means 15, use optical sensor 100 to analyze floc characteristics versus mixing time, for a user defined duration, such as 4 minutes.
2. Discard sample, rinse, and drain system.
3. Change the selected full-process coagulant dose 11A, 11B, 11C, or 11D. A typical change might be up or down 10%. Following a suitable delay, transfer the new sample of coagulant effluent downstream from a chemical addition point 13 to the chamber 1301. Activate the mixing means 15. Use the optical sensor 100 to analyze floc characteristics for the user-defined time.
4. Compare the results of analysis of the first dosage (1) to the results of the analysis of the second dosage (3) to determine the impact of a change in coagulant dosage on floc characteristics over time
5. Select next dosage based upon the change direction from the previous step—either dose increase or decrease— which produces appropriate floc characteristic increase over time.
6. Repeat steps 2, 3, 4, and 5 above until either the maximum floc characteristic value is found or, alternately, an appropriate value of diminishing return has been reached, or yet other criteria are achieved.

Note, all the above steps 1-6 need to be repeated regularly because a change in raw water, and therefore coagulant-dose demand, can only be determined by repeating this empirical testing protocol action steps 1-6. For optimizing coagulant dosing of other alternative water sources or combinations and/or coagulant species or combinations, samples can be prepared by adding coagulant in a simulation coagulation system 1302 as described previously using the 6-step protocol provided in the previous paragraph by appropriately revising the source and preparation protocol of test samples.

FIG. 12 depicts a flocculation analysis system 1400 that possesses many features common to the flocculation analysis system 1300 of FIG. 11, as enumerated earlier. One difference between 1300 and 1400 is that 1400 is designed to be deployed as a fully submerged unit enclosed by closable valves 144 and 145 that surround a vertical tube section to create a chamber 1401. The flocculation analysis system 1400 may be positioned at one or more locations 16A, 16B, or 16C directly within a full-process flocculation system 3. The flocculation analysis system 1400 can characterize floc particles using multiple modes:

a) With both valves 144 and 145 open, the flocculation analysis system 1400 performs continuous full-process in-situ analysis of floc characteristics as they pass through the sample volume 121. In this case, continuous sample flow occurs through volume 121 due to the combined turbulence resulting from the full-process flow stream and the ambient fluid mixing within the full-process chamber 3. Following the closing of both valves 144 and 145, the isolated batch sample transitions into gravitational settling at which time floc particle gravitational settling and floc density computations begins. Note, that by closing both valves 144 and 145, a full-stream process coagulated-flocculated sample is taken in-place thereby isolating the sample from the full-process turbulent mixing, and thereby favoring minimizing floc particle disruption during sample acquisition. Further, during isolating of a water sample it helps to minimize floc particle disruption, which is also a function of shear (or velocity gradients) in the water. Other ways to minimize floc particle disruption include minimizing any protrusions in the chamber 1301 or 1401. The shear of the water is also a function of the power input per unit volume in the chamber 1301 or 1401. By controlling the power input per unit volume of the mixer, one can control the shear in the chamber 1301 or 1401 and resulting floc particle disruption.

b) On-demand analysis of process in situ floc particle mass density by initiating particle gravitational settling analysis and density computation immediately upon the closing of both valves 144 and 145, at the location of the flocculation analysis system 1400 in a flocculation reactor 16A, 16B, or 16C.

c) Batch-mode flocculation analysis of floc characteristics over time by closing the valves 144 and 145 and activating the mixer 15. Batch-mode flocculation analysis allows comparative testing of flocculation goodness in continuous-flow mixing in the full process 3 versus in the 'ideal' mixing environment obtained in an isolated batch-sample mode of flocculation.

d) Sequentially repeating steps ii and iii to periodically start and cease controlled mixing to perform both continuous analysis of floc formation characteristics interrupted and, combined with periodic floc density measurement over flocculation mixing time.

By employing the flocculation analysis system 1400 and the modes of operation discussed in this disclosure, one can compare flocculation-processing goodness. This is necessary as there is no currently known method for calibrating floc-particle characteristics, or for determining a base line for flocculation. By reference to FIG. 7 and related text, it is strongly indicated that full-scale flocculation systems may not operate as effectively as is theoretically possible. Because of the near "ideal" flocculation obtainable in the small batch analysis system represented in FIG. 12 with operating modes (iii) or (iv), a comparison of floc-particle characteristics between an extant full-process flocculation system (less that "ideal) and an "ideal" flocculation system 1400, can be accomplished utilizing the two sets of numerical results. Moreover, the numerical results produced by the flocculation analysis system 1400 may also be used to improve the design and operational control of full-process flocculation mixing.

Figure 13:
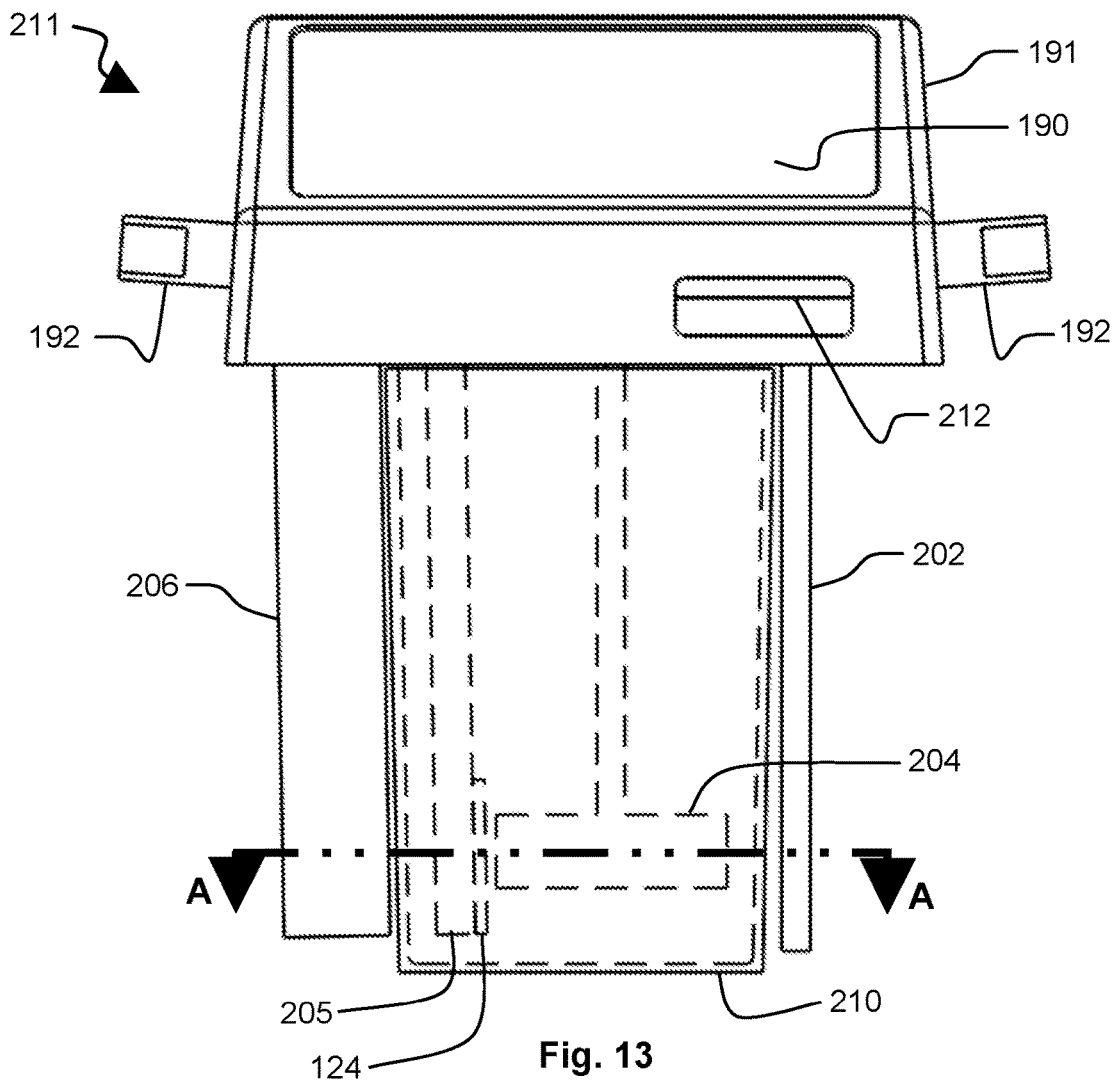
FIG. 13 shows a front view of an automated water sample jar testing system.

FIG. 13 shows a front view of an automated water sample jar testing system at 211. The system 211 comprises a reactor tank (or chamber), shown at 210, into which an instrument is placed. The instrument in FIG. 13 comprises: a camera housing 206; a leg 202; a mixer paddle 204; an illuminator 205; a contrast plate 124; a top case 191; a touch screen display 190; two handles 192; and removable non-volatile solid-state memory 212. The memory 212 can be removed by a user through an access hole in the top case 191.

Figure 14:
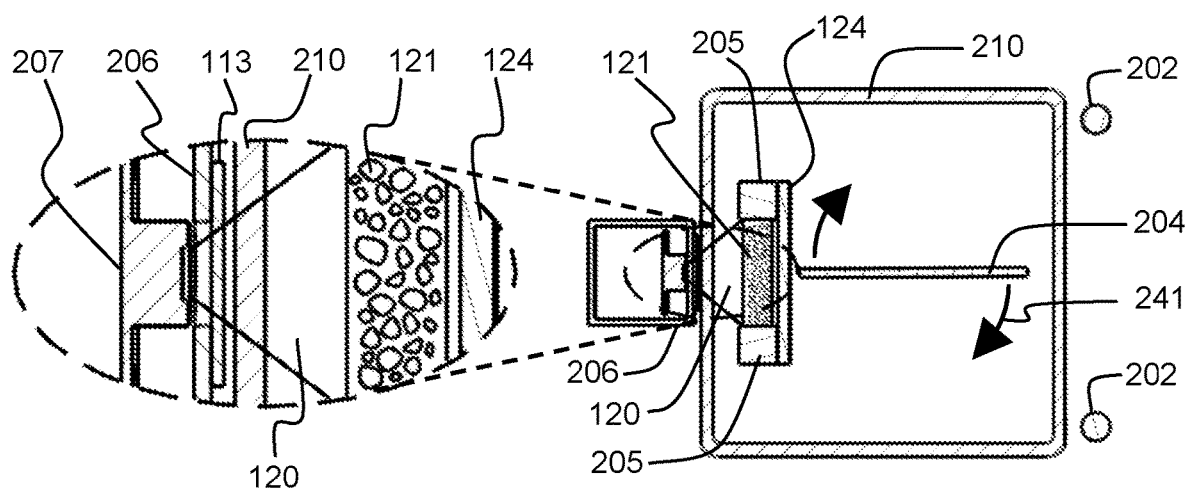
FIG. 14 shows section A-A of FIG. 13.

FIG. 14 shows section A-A of FIG. 13. This gives another view of the tank 210, the location of the two legs 202, the mixer paddle 204, the camera housing 206, the location of the two illuminators 205, and the contrast plate, that were also shown with reference to FIG. 13. FIG. 29 shows a digital optical camera at 207. The digital optical camera 207 and optical element 112 look through an optical window 113 of the camera housing 206 and the clear wall of the tank 210 to view a water sample within the tank 210 where the optical view volume 120 intersects the illumination volume 119, thereby creating the sample volume 121 where in floc particles are illuminated and imaged by the camera 207. The contrast plate 124 located behind the sample view volume 121 enhances floc particle imaging.

Further referring to FIG. 14, the tank 210 has a substantially square horizontal cross-sectional shape. This cross-sectional shape with substantially square corners has functional significance because the corners of the tank can act as baffles, allowing for the mixing paddle 204 to create a more complex mixing pattern than a tank with a round cross section having a mixer paddle in its center. The mixer paddle 204 rotates about a center that is offset from the midpoint of the square horizontal cross section of the tank 210, which further complicates the fluid path, aiding in the mixing process. This path of mixer impeller rotation is shown at 241. The illuminators 205 and contrast plate 124 located at approximately the same elevation as the mixer paddle act as baffles as well. The mixer paddle shown at 204 in FIG. 13 and FIG. 14 comprises a two-blade flat impeller. Other types and sizes of impellers can also be used based on impeller design guidelines understood by those skilled in the art. The impeller blade in the mixer paddle is located a distance above the floor of the tank that is approximately one half of the horizontal length of the impeller blade. The mixer impeller blades have a horizontal length that is between one third and one half of the diagonal distance between the corners of the horizontal cross-sectional shape.

Figure 18:
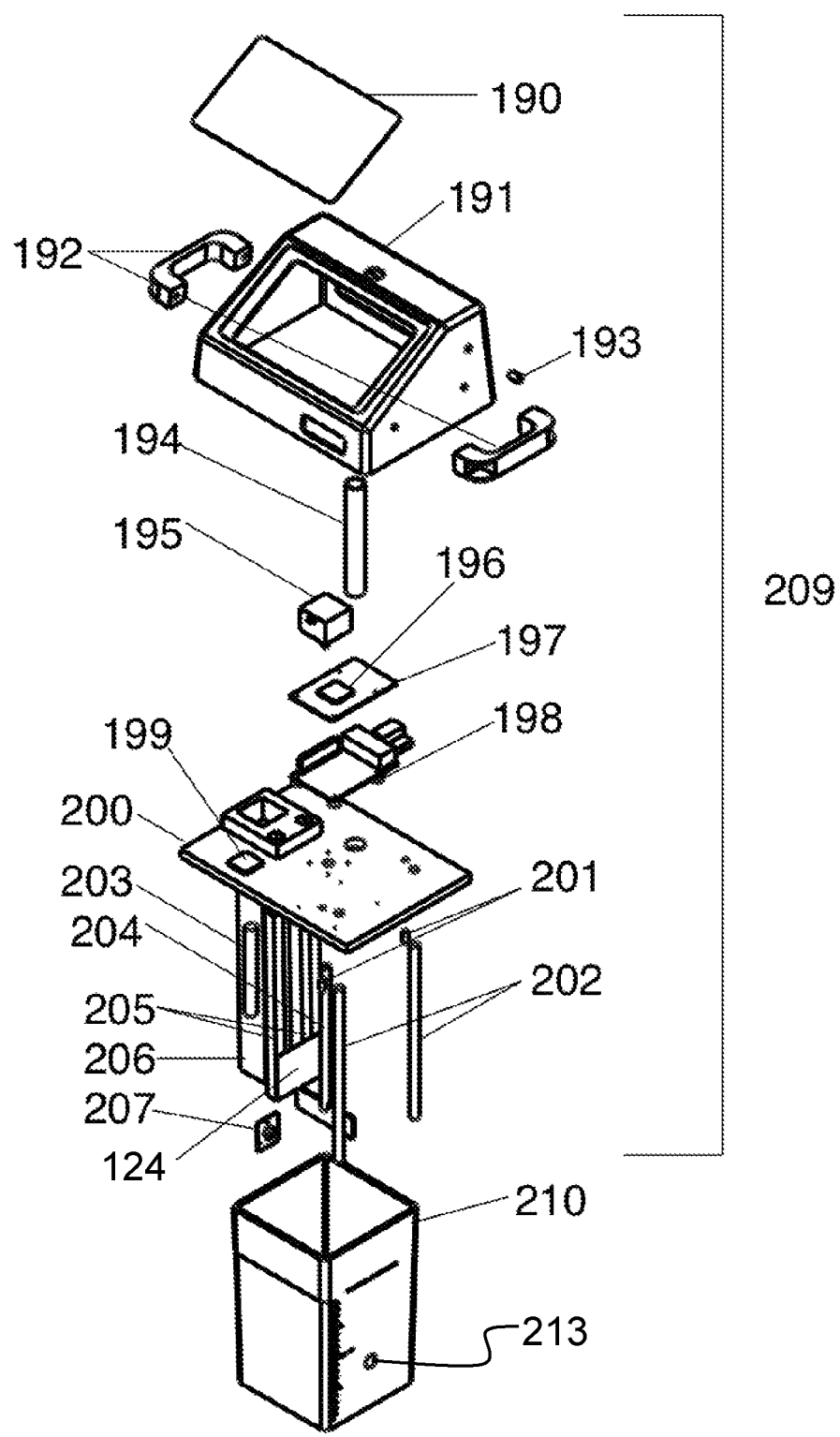
FIG. 18 shows an exploded view of the system of FIG. 13.

FIG. 15 shows a right-side view of the system 211 of FIG. 13. FIG. 16 shows section B-B of FIG. 15. FIG. 17 shows a perspective view of the instrument portion 209 of the automated water sample jar testing instrument 211 (without the chamber 210). FIG. 18 shows an exploded view of the system of FIG. 13. The automated system shown in FIGS. 13-18 can be a laboratory bench system 211 used for off-process semi-automated testing of batch coagulation-flocculation and settling.

In the system 211 shown in FIGS. 13-18, a user-removable chamber, which can also be called a reactor tank, is shown at 210. The reactor tank 210 and mixer paddle 204 are similar to the jar 210 and paddle 204 used in an industry standard jar test. In the embodiment shown in FIGS. 13-18, the reactor tank 210 has at least one region that is sufficiently clear to allow a user to visualize the floc in the water sample. This clear region of the reactor tank can also comprise calibration markings 240 that assist a user in visualizing the volumetric level to which the tank (or chamber) has been filled. For example, the tank can be filled to a standard volume, typically 2 liters, or the tank could be filled to any other level capable of being understood by anyone skilled in the art. There is significance to a tank configured for holding approximately 1-2 liters of a water sample because the standards for traditional jar tests are based on this size of a tank.

Further referring to FIGS. 13-18 an intelligent programmable instrument is shown at 209. The instrument can record time series data of the floc particle dynamics that occur following coagulant addition to a water sample. The two separable subsystems, 210 and 209, are configured to provide a convenient means for a user to conduct a water sample test that comprises:

(a) water and coagulant sample acquisition;
(b) automated, recallable, reproducible, precision water sample mixing control processing;
(c) automated floc particle formation data acquisition, data storage, and data presentation;
(d) water sample disposal; and
(e) system preparation for conducting the next water sample test.

As shown in FIGS. 13-21, the instrument 209 can be separated into units, which can further be divided into individual elements as follows:
  (i) A user interface unit, comprising a touch screen 190, a top case 191, handles 192, and a fill tube 194;
  (ii) An electronics unit, comprising a 12-volt direct current power jack 193, a stepper motor controller integrated circuit chip 196, an interface module 197, a processor-controller circuit board (or single board computer) 198, a pH and/or temperature circuit board 199, and a pH and temperature sensor 203, and a temperature probe 233;
  (iii) A floc sensor unit, comprising two light sources 205, a digital optical camera 207, an optical window 113, an optically clear tank wall 210, an optical view volume 120, an illumination volume, an sample volume, and a contrast plate 124;
  (iv) A mixing unit, comprising a stepper motor 195 and a mixer paddle 204 in which the stepper motor drives the mixer paddle; and
  (v) An instrument support unit comprising a base plate 200, alignment pins 201, legs 202, and a camera housing 206. This instrument support unit can function as a freestanding tripod that supports the entire instrument when the reactor tank 210 is removed to change water samples.

The contrast plate 124 in FIG. 13, FIG. 14, and FIG. 18 serves to absorb unwanted radiation such as scattered light and thereby improve noise reduction and at the same time tends to enhance image contrast of black versus white pixel detection. In turn, this enhances edge detection and image resolution, which in turn results in more accurate particle area and perimeter measurements. Therefore, particle volume and equivalent spherical diameter calculation accuracies improve. In one embodiment, the contrast plate 124 comprises a sheet of a matte black aluminum such as Cinefoil (TRADE). The contrast plate can be made of anything of equivalent properties capable of being understood by anyone skilled in the art. The contrast plate 124 can be attached to the two illumination columns 205 placed on their sides facing directly opposite of the digital camera 207 and centered on the camera optical view axis (not illustrated). Consequently, the contrast plate 124 is located directly beyond, but separated from, the sample volume 121, specifically illuminated by the opposing illuminators 205. Effectively, the contrast plate 124 acts as a light absorbing "black body" just beyond the illuminated floc particles imaged by the camera significantly enhances floc-particle analysis by eliminating unwanted radiation.

A notable design challenge relates to how to physically configure the mixer paddle 204 and the sensor system (comprising the light source 205, camera housing 206, digital optical camera 207, and contrast plate 124) into an instrument 209 that can be placed into an industry standard test reactor, such as the chamber shown at 210, and yet comply with the following conflicting challenges:
  (a) use an existing digital optical camera 207 which has a focal length of 1.05 inches as measured from the camera-lens-front-surface to illumination zone centerline horizontal axis that is orthogonal to the camera-view horizontal axis;
  (b) the instrument 209 should straddle the wall of the chamber 210 so the base plate 200 can rest upon this wall;
  (c) ensure that the camera housing 206 and light source 205 (in the form of two illumination columns) can maintain the appropriate horizontal separation from the base plate 200 to their terminus relative to the reactor sloping wall, nominally 1 degree inward from vertical;
  (d) make the complete instrument unit 209 readily replaceable and removable, as a complete device, onto and from the chamber 210;
  (e) replicate the mixing system of the industry de facto standard test system to the maximum degree possible by using a precisely calibrated, controllable mixing system configured to provide rotary mixing speeds ranging from 0 to 250 revolutions per minute (RPM); and
  (f) place the illuminated-sample volume 121 (shown in FIG. 6 and FIG. 14) in proximity of and within the mixing zone of mixer paddle 204 inside of the chamber 210 and in proximity to the bottom of the chamber 210, and more generally in the bottom half of the water and coagulant mixture in the chamber.

Regarding the mixing system, in one embodiment, the stepper motor 195, which is responsive to the stepper motor controller integrated circuit chip 196, is configured to allow the stepper motor to be controlled in 1.8-degree increments, or into 200 positions per revolution. The system could be configured to allow at least 40 increments per revolution, at least 80 increments per revolution, at least 120 increments per revolution, at least 160 increments per revolution, or at least 200 increments per revolution.

Due to the requirement for fast processing of image data to generate outputs needed in embodiments of the present invention, it is desired to have a fast low-cost processor. In one embodiment, the microprocessor 215 on the processor controller circuit board 198 (also known as a single board computer), is a multi-core RISC (reduced instruction set computer) processor, such as those designed by Advanced RISC Machines (ARM). The microprocessor 215 can be a system on a chip (SOC) that further comprises both a central processing unit (CPU) and a graphic processing unit (GPU) on the same chip.

Referring to FIG. 13, FIG. 17, FIG. 18 and FIG. 21, a touch screen display 190 is connected to and communicates with the processor-controller circuit board (i.e. single board computer) 198. In one embodiment, this connection is made using a serial interface that further incorporates differential signaling in which each data lane is carried by two wires, such as the display serial interface (DSI) that has been developed by the Mobile Industry Processor Industry (MIPI) alliance. The touch screen 190 displays a custom user interface that informs the user of status information such as (a) numerical and graphical results, (b) test progress, and (c) the recall of prior results for comparison. As will be described later in this disclosure, the custom user interface presented on the touch screen 190 can be configured to accept user input such as:
  (a) initial system set up and configuration information;
  (b) user graphical display preferences such as which variables to display, whether real-time results or test results overlay should be displayed, and user selection of which specific test results should be displayed; and (c) for creating real-time user-written annotations to be added as notes to a real-time graphical presentation of the empirically-collected data.

Figure 19:
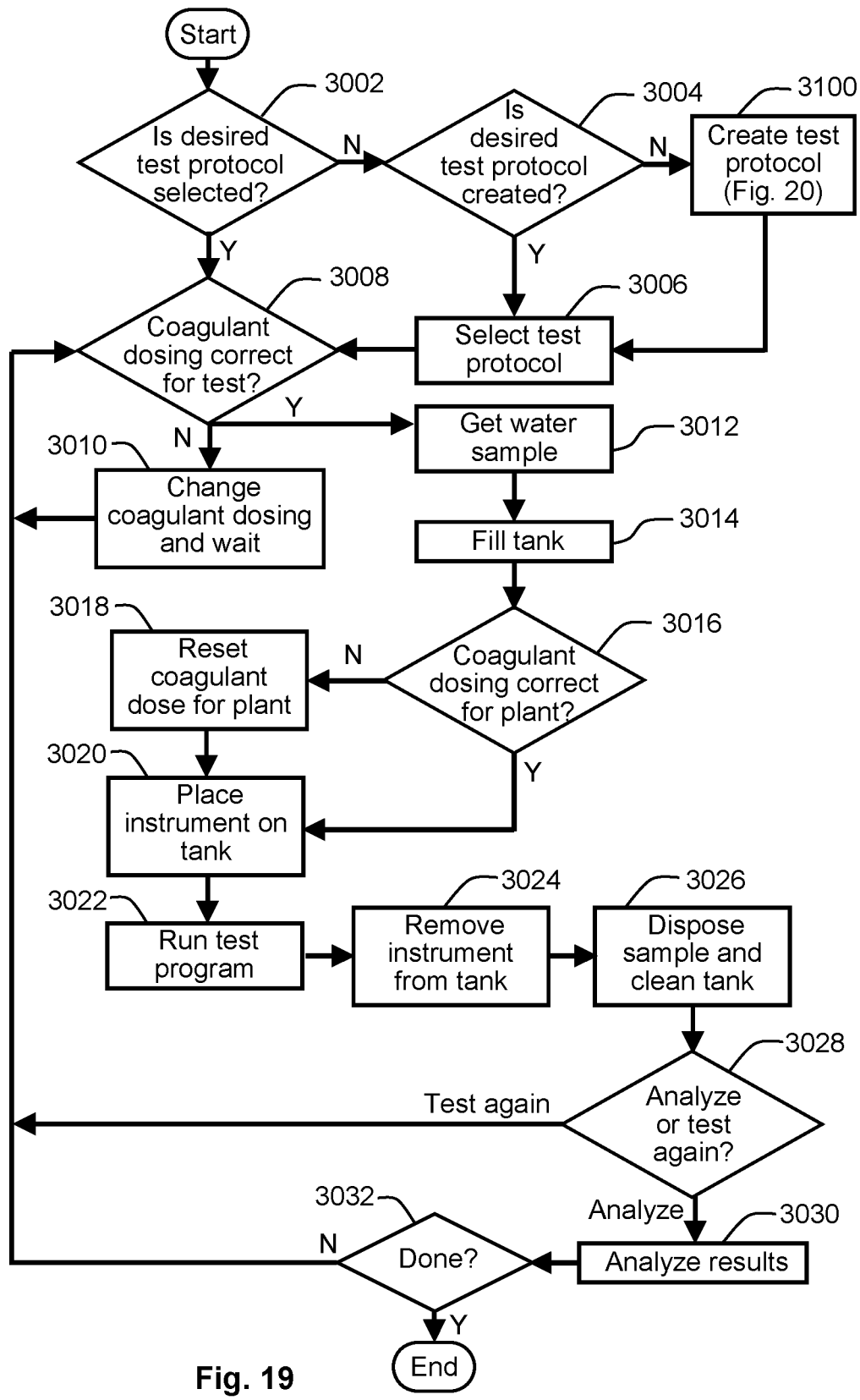
FIG. 19 shows a process for automated water sample jar testing.
Figure 20:
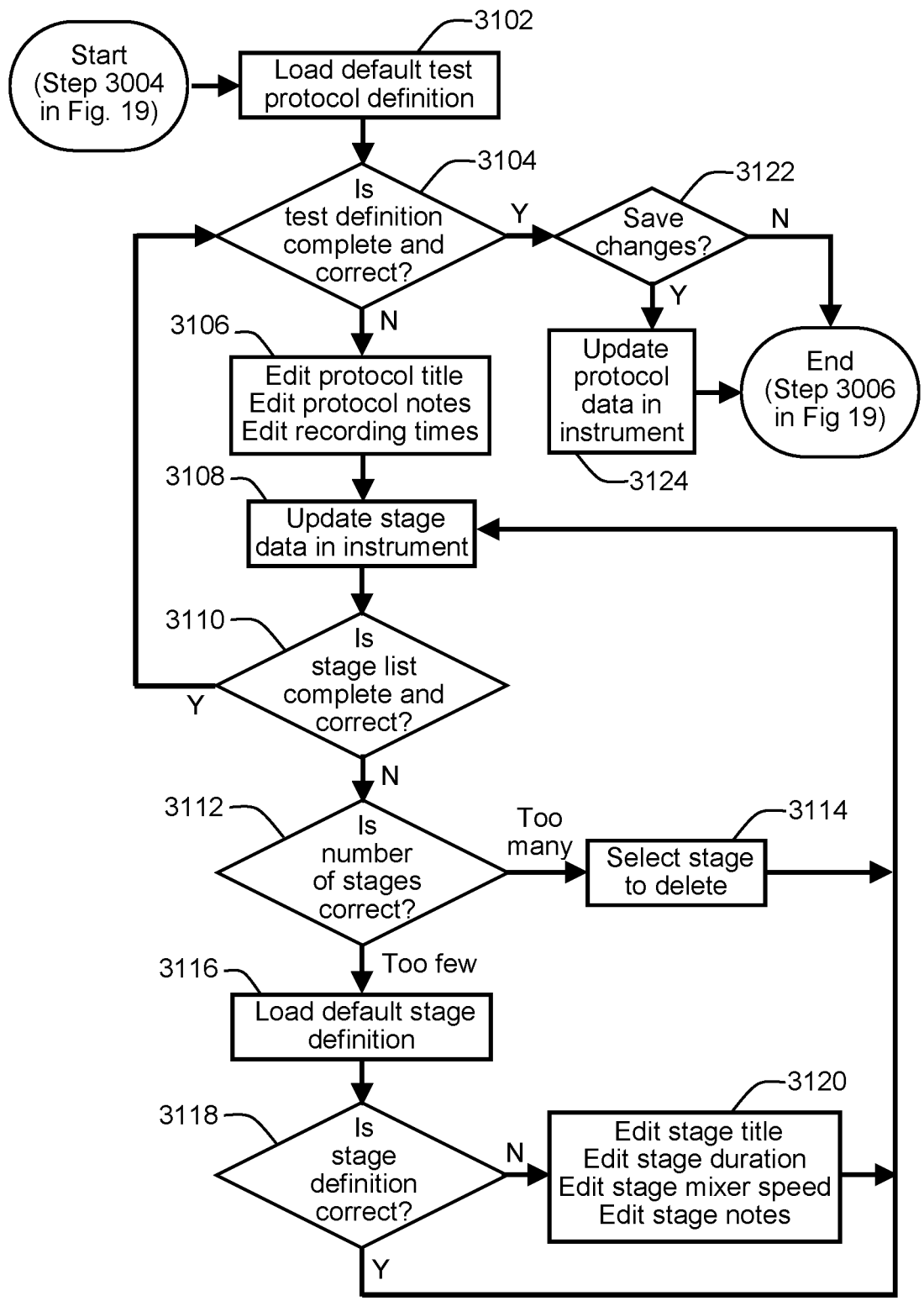
FIG. 20 shows step 3100 (Create Test Protocol) of the process shown in FIG. 19.

FIG. 19 illustrates the steps involved in sample processing management by the semi-automated water sample jar testing system that was illustrated in FIGS. 13-18. FIG. 20 shows step 3100 (Create test protocol) of the process shown in FIG. 19. The method shown in FIG. 19 and FIG. 20 can be performed in the instrument that was shown at 209 in FIGS. 13-18. The method shown in FIG. 19 and FIG. 20 can be used to perform experimental analysis for changes in coagulant dosing in an off-line fashion. The empirical results of this off-line testing can then be applied to optimize coagulant dosing of the full-flow process stream, which was shown in FIG. 1, by obtaining full-process water and coagulant samples at points 13A, 13B, 13C, or 13D in FIG. 1. Referring to FIG. 19, the semi-automated water sample jar testing method begins at 3002 with a determination of whether the user (typically a plant operator) has selected the desired test protocol on the control panel of the instrument that was described with reference to FIGS. 13-14. If the result of the determination in step 3002 is no, the user, at step 3004, determines if a desired test protocol has been created on the instrument (209 in FIGS. 13-18). If the desired test protocol has not been created, the user can create a desired test protocol, a step that is shown at 3100 and that is detailed in FIG. 20.

Continuing with the process shown in FIG. 19, the user can select an existing test protocol (the step shown at 3006) and then determine whether the coagulant dosing for the full process is correct for the test to be conducted by the instrument, a step shown at 3008. It should be noted that the instrument (209 in FIGS. 13-18) is typically used for running tests on samples of water and coagulant mixtures that come from the full process plant, such as the one illustrated in FIG. 1 and the samples are typically manually obtained downstream of a coagulant addition point, such as at 13D or 14 in FIG. 1. Because the sample is obtained from an operating plant, a plant operator can obtain samples of different mixes by changing the coagulant dose for the plant and wait for a new mixture to arrive at the sampling point and thereby remain constant and representative of the desired dosage as indicted at step 3010. When the coagulant dosing is correct for the test, the user gets a water sample 3012 and fills the tank 3014. Note that the tank being referred to in FIG. 19 is the same as the chamber that was shown at 210 in FIGS. 13-18. If the user had temporarily changed the coagulant dosing in order to obtain the water sample (a decision step shown at 3016), the user must reset the coagulant dose for the plant (as step shown at 3018) in order for the water plant to continue as it had prior to the dosage change that was made to collect the test sample. Then the instrument (209 in FIGS. 13-18) can be placed on the tank (210 in FIGS. 13-18), a step shown at 3020, and the test program that had previously been selected (for example at step 3006) can be run, as shown at step 3022. When the test has been run, the instrument can be removed from the tank 3024, and the water sample discarded and tank cleaned, a step shown at 3026.

Further continuing with the process shown in FIG. 19, the user can then decide to analyze the data from the test that has been run or perform another test before analyzing, a decision shown at 3028. If the decision is to test again, the user loops back to the determination of coagulant dosing step shown at 3008. If the decision is to analyze, the user analyzes the test results as shown in step 3030. After analyzing the test results, the process can end if the user is done or loop back to step 3008 if further testing is desired, as shown by the decision box at 3032.

FIG. 20 details the steps that can be taken by a user to devise and program a new unique test protocol in the instrument that was shown at 209 in FIGS. 13-18. These steps fit into step 3100 that was shown in FIG. 19. This unique test protocol can comprise definitions of the sequence of mixing speeds and mixing durations. For example, the user could specify 8 different mixing speeds that will run for 8 different lengths of time or a sequence representative of the processing in the full plant. These different mixing speeds and durations could be selected to try to simulate (or mimic) the actual mixing speeds and times that a water sample might go through in the full-scale water treatment or wastewater treatment facility.

The process shown in FIG. 20 can begin with the loading a default test protocol definition and displaying this on the touch screen display 190 of the instrument 209 that was shown in FIGS. 13-18. The user then makes a series of edits until the desired test definition is complete and correct as determined in the decision box shown at 3104. The instrument 209 is configured 3110 to allow a user to specify the following parameters as part of a test protocol definition:

(a) Test protocol title, notes and recording times, as shown at 3106;
(b) The number of stages in the test, as can be modified in steps 3112, 3114, and 3116; and
(c) The details of each stage as shown at 3110, 3118, and 3120.

Once the user is satisfied that the test definition is complete and correct in step 3110, the user can choose to save the changes (step 3122) which will cause the protocol data in the instrument to be updated. The process of defining and saving a new test protocol in the instrument, 209 in FIGS. 13-19, is then completed.

Referring in greater detail to the functionality configured into the instrument (209 in FIGS. 13-18) that can perform the processes shown in FIG. 19 and FIG. 20:

(a) The instrument can store a plurality of user programmed test protocol definitions. For example, on one embodiment, the instrument can store at least 10, at least 20, at least 50, at least 100, or at least 200 test definitions.
(b) The instrument can store a plurality of stages in a test definition. For example, in one embodiment, the instrument can store at least 10, at least 20, at least 50, at least 100, or at least 200 stages in a test definition.
(c) The protocol notes can be a free text field that allows a user to store at least 256 bytes, 1024 bytes, 2048 bytes, 4096 bytes, or 8192 bytes of text per note.
(d) The stage notes can be recorded as data is being captured during a test. For example, a user could click on the time axis of the touchscreen display (190 in FIG. 13, FIG. 17, and FIG. 18) and record (by typing on the touch screen or through the use of any other input device) any notes, remarks, or real time comments relevant to the test being run.
(e) The order of the stages can be changed in response to user input.
(f) The instrument can record test data at a frequency of at least once every second, every 2 seconds, every 5 seconds, every 10 seconds, every 15 seconds, every 20 seconds, every 30 seconds, every minute, every 2 minutes, or every 5 minutes.

(g) The recording times described previously, with reference to step 3106 in FIG. 21 can be the total time of all the individual test stages necessary to complete a test.

Figure 21:
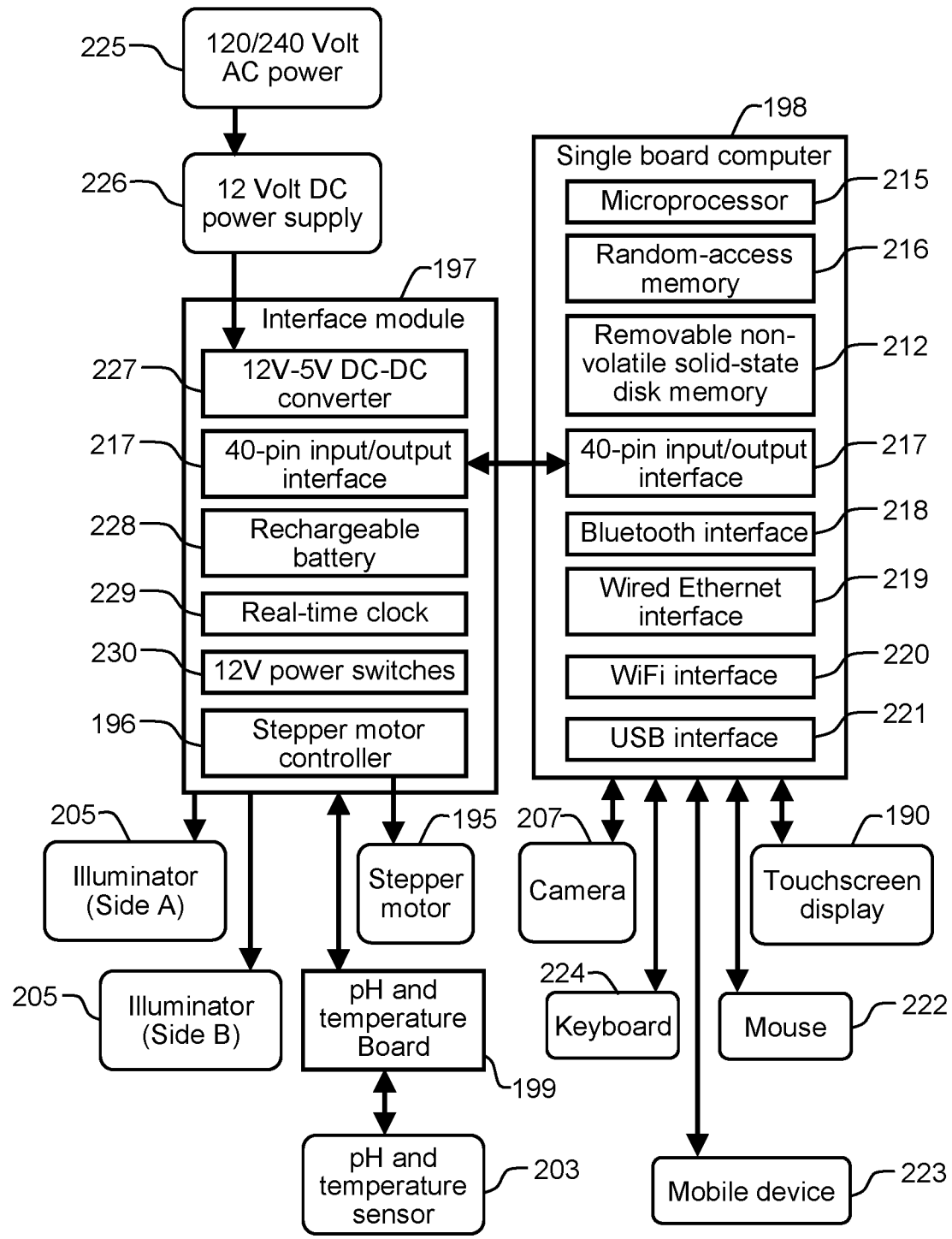
FIG. 21 shows a block diagram of the main electronic modules of the automated water sample jar testing system and method shown in FIGS. 13-20.

FIG. 21 shows a block diagram of the main electronic modules of the automated water sample jar testing system and methods shown in FIGS. 13-20. The main electronics are housed on a single board computer 198 (or processor-controller circuit board) that is connected to an interface module 197 through a 40-pin input-output interface, shown at 217. As shown at 225, 120/240 Volt alternating current powers the interface module 197 through a 12 Volt direct current power supply 226. The power supply 226 delivers power to a 12V to 5V DC-DC converter 227 on the interface module 197 through the power jack 193 that was shown in FIG. 15 and FIG. 18. The single board computer gets its power from this interface module 197 through the 40-pin input-output interface. The single board computer 198 also comprises a microprocessor 215, random access memory 216, a removable non-volatile solid-state memory disk 212, a Bluetooth interface 218, a wired internet interface 219, a WiFi (802.11) interface 220, and a USB interface 221. The removable non-volatile solid-state memory 212 can comprise flash memory and this flash memory can be in the form of an SD card. Externally the single board computer 198 supports the camera 207 that was described with reference to FIGS. 13-18, a keyboard 224, the touchscreen display 190 that was described with reference to FIGS. 13-18, a mouse 222, and mobile device(s) 223.

Further referring to FIG. 21, the interface module 197 also comprises a rechargeable battery 228, a real-time clock 229, 12 Volt power switches 230, and a stepper motor controller 196. The stepper motor controller 196 is connected to the stepper motor 195 that drives the mixer paddle 204 that was also shown in FIG. 16 and FIG. 18. The illuminators 205 (on sides A and B) that were previously shown in FIGS. 13-18 are controlled and powered by the interface module 197. The interface module 197 also powers the pH and temperature board 199, which receives information from the pH and temperature sensor 203.

The real-time clock 229 is a vital component that serves multiple needs:
(a) It ensures that the data stored to the database in non-volatile solid-state memory 212 are in chronological order;
(b) It provides correct time stamp associated with each floc particle image provided by the camera 207, and
(c) It is programmed to routinely insure that it maintains updated with UTC (coordinated universal time) information using the "atomic clocks" as the reference for maintaining accuracy. Thus, the "official time reference" maintains the local reference clock, such that time stamps are accurate atomic clock time.

The real-time clock 229 involves both a hardware and software component. In one embodiment, the hardware component uses a commercial RTC (real time clock) integrated circuit as a local time reference. This RTC contains a temperature compensated, calibrated oscillator, counting circuitry and a battery mechanism to maintain operation independent of system power. While this RTC clock has a high degree of precision, software can be used to achieve a high degree of accuracy (<100 ms from UTC, also known as Coordinated Universal Time) within the system. NTP (network time protocol) software within the operating system is used to compare known, highly accurate clocks against the internal reference clock. On initial startup or whenever the clock has great errors (>30 seconds) the clock is set to the best estimate of the reference time. This is an estimate because of the transmission delays that occur in the communication of clock values between systems. Over time, many comparisons can be made for the transmission delays between reference times and the local times, and those statistics can be used to compute the systematic error in the local clocks. Software can then apply correction factors and offsets to maintain optimal accuracy relative to established UTC (Coordinated Universal Time). In case the unit is powered down and later powered up a rechargeable battery 228 can be used to ensure reliability The electronics shown in FIG. 21 can be configured to comprise both close and mid-range wireless communications functionality (using protocols such as Bluetooth, Zigbee, and WiFi), a keyboard and mouse (not shown) could be used for user input, as an alternative or in addition to the touch screen 190. These electronics can be configured to communicate with a plant data system such as SCADA (supervisory control and data acquisition) and this communication can be via a local area network.

The embodiment shown in FIGS. 13-21 can continuously monitor and produce the following real time metrics for coagulation-flocculation-settling effectiveness:
(1) Floc particle count ($n_c$), which can be measured in floc particles per milliliter (#/ml);
(2) Floc volume concentration ($V_c$), which can be measured in milliliters per liter (ml/l);
(3) Equivalent average spherical floc particle diameter ($D_e$), which can be measured in millimeters (mm);
(4) Computed floc particle volume ($V_t$), typically the average volume for all particles in the sample, which can be measured in microliters (µl);
(5) Initial (perikinetic-orthokinetic) floc growth rate ($F_r$), which can be measured in milliliters per liter per second (ml/l per second);
(6) Maximum floc volume concentration ($V_{c,mx}$), which can be measured in milliliters per liter (ml/l);
(7) Maximum average spherical floc particle diameter ($D_{e,mx}$), which can be measured in millimeters (mm);
(8) Floc volume settling rate after mixer is turned off ($V_{c,s}$), which can be measured in milliliters per liter per second (ml/l per second);
(9) Minimum floc volume concentration at the end of settling ($V_{c,mx}$), which can be measured in milliliters per liter (ml/l); and
(10) Percent of floc that settled during the test ($V_{\%}$), which can be measured as a ratio or percentage (%).

The preceding coagulation-flocculation-settling effectiveness metrics offer facility operators and design engineers information that has not been available in the prior art. Moreover, these data provide insight for diagnosing problems in the downstream flocculation, clarification, and filtration steps. Of the real-time metrics for coagulation-flocculation effectiveness identified above, the more informative are usually found to be floc volume concentration $V_c$, as illustrated in the graph in FIG. 22, and floc diameter $D_e$, as illustrated in FIG. 23. Experience at operating facilities has shown that for flocculation characterization $V_c$ and $D_e$ are more or less equivalent for characterizing the flocculation growth stage. However, for the bulk of plants that involve clarification, $V_c$ is generally preferred as it also it the superior metric for floc-pollutant settling; a primary aim in operations for minimizing filter solids loading. When comparing the results shown in FIG. 22 and FIG. 23, regarding judging coagulation-flocculation effectiveness, it is important to recall that these two different parameters are nominally equivalent, proportional and interchangeable.

FIG. 22 shows one example of typical data collected by an automated water sample jar testing system. FIG. 22 displays a series of four different dosages of $FeCl_3$, ranging from 10 to 50 mg/l, collected over seasonal change of raw-water quality at an operating facility; utilizing a development system similar to the system and method shown in FIGS. 13-18. The graph in FIG. 22 displays time in minutes on the X-axis and floc volume concentration ($V_c$) in parts per million on the Y-axis. In the four test runs illustrated by the graph in FIG. 22, the initial 10 minutes involved gentle agitation of 25 rpm referred to a flocculation period, utilizing an apparatus similar to FIG. 13-21. At 10 minutes, the mixer was turned off, which allowed a period of quiescent settling; thereby simulating the sequence of operating treatment plant processing steps (flocculation and clarification) preceding filtration.

Referring more generally to a typical water processing jar test that might produce the data shown in FIG. 22, there is a sequence of three different test-protocol-induced processing phases. These are (1) the sample preparation phase, (2) the flocculation phase, and (3) the settling phase. The flocculation phase can be further divided into multiple user-selected time periods of different mixing speeds and duration. These user-selected durations and mixing speeds during the flocculation phase can be chosen to simulate the flocculation process of a full-scale water treatment or wastewater treatment facility. FIG. 22 illustrates the flocculation phase, when floc volume concentration is generally increasing or steady and high, and the settling phase, when floc volume concentration is rapidly decreasing or steady and low.

The graph in FIG. 22 illustrates and example of the response of a test sample to variations in coagulant dosing. Referring to the flocculation phase in this graph, various physical phenomena are occurring. The initial rapid increase in floc volume concentration is the result of perikinetic flocculation and orthokinetic flocculation, which cause floc particle growth involving different mechanism related to floc particle size and fluid differential movement scale, as will be described in more detail later. The slopes of these curves flatten after a while, as the rate of floc growth decreases and approaches a steady-state condition. Large floc particles may also break up as a result of fluid shear in the mixing that occurs during the flocculation phase. All of these factors affect the shapes of the floc volume concentration curves shown in FIG. 22. This type of time-series volume concentration data (not available in the prior art), improves scientific understanding of the flocculation process and improves operational control of the main method (flocculation and sedimentation) used in the vast majority of water treatment facilities around the world.

To most effectively exploit the type of time-series data illustrated in FIG. 22 that are provided by embodiments of the present invention, it is important to have an analysis methodology that (a) minimizes random variation from test to test and (b) most closely simulates the full process of a water treatment facility. To this end, a programmed processor controlled device, such as the embodiment shown in FIGS. 13-20, can be used to simulate actual processing conditions. Accordingly, embodiments of the present invention have been designed to mimic the following conditions:

1) A sample preparation phase (typically 5-10 seconds) of intense mixing (typically 100-200 revolutions per minute) to stabilize the sample to a common initial particle condition. This first (or sample preparation) phase can be referred to as a rapid-mix and is not shown in FIG. 22 because it occurs so quickly, precedes the flocculation phase, and yields little useful information.

2) Next comes the flocculation phase, which may last from 5 to 15 minutes and can further be divided into the following sequence of time segments:

a. A time segment (typically 2-4 minutes) of combined perikinetic and orthokinetic flocculation occurs immediately after the sample preparation phase. This time segment is characterized by the rapid increase of total measured floc particle volume concentration as shown by the first approximately 2-4 minutes of the graph in FIG. 22. During this time segment, the slope of the floc particle volume concentration line is highest and Floc Volume Concentration Change Rate ($F_r$) is a valuable metric for judging the relative effectiveness of coagulant dosing. In cases where it is suspected that the coagulant dosing is significantly off-optimum and rapid changes in coagulant dosing are called for, quickly measuring Floc Volume Concentration Change Rate ($F_r$) for several different water and coagulant dosage samples may be sufficient for identifying the direction in which coagulant dosage needs to be changed to get to an optimum dosage, using the theory and strategy that will be further explained with reference to FIG. 23 and FIG. 24.

b. A time segment (typically 6-8 minutes) of combined orthokinetic flocculation and floc breakup characterized by an asymptotic, more-or-less declining rate of floc growth that can ultimately approach a steady state condition, at which point ($V_{c,mx}$) and ($D_{e,mx}$) can be determined. In some cases of polymer overdosing, the end of this time segment can exhibit declining floc volume concentration due to excessive floc breakup. Floc breakup is caused by fluid shear and occurs as floc particles statistically pass though localized zones of high fluid shear near the tips of mixing blades. The steady state mean floc diameter and floc volume concentration provide further potential metrics for judging relative coagulant dosing effectiveness.

3) The settling phase occurs after the mixer is turned off. This phase is characterized by a decrease in floc volume concentration due to the settling of floc below the sensor view sample volume location (see 121 in FIG. 6 and FIG. 14). The rate ($V_{c,s}$) and extent ($V_{c,mx}$) of reduction in floc volume concentration are metrics are important in conventional filtration plants that have a settling stage—i.e., clarifier, plate settler, or DAF (dissolved air flotation)—process preceding filtration. A fast decrease in floc volume concentration portends decreased floc solids filter loading and in turn generally longer filter runs, which translates to increased process effluent volume throughput, and consequently more efficient plant operation.

Embodiments of the system illustrated in FIGS. 13-18 and the process illustrated in FIG. 19 and FIG. 20 can be used for high-precision mixing studies of water and coagulant samples. Intuitively, practitioners have hypothesized that sequential stages of different mixing intensities (i.e. mixer speeds) could improve subsequent settling and/or filtration performance. However, prior art instrumentation has not been sufficient for determining whether it is better to (a) increase mixer speed from stage to stage or (b) decrease mixer speed from stage to stage, as floc particles form. The instrument shown at 209 can be configured for precisely controlling mixing speeds as a function of time, or in response to changes in volume concentration $V_c$, number concentration $N_c$, computed particle volume $V_i$, and/or synthetic or equivalent particle diameter $D_e$. The use of a stepper motor 195 and control circuitry, 196 and 197, facilitates the precise control of mixing rotational speed (as measured in revolutions per minute) and direction (clockwise or counterclockwise) in response to elapsed time and empirical data from the floc particles in the water sample in the chamber 210. The device shown in FIGS. 13-18 can be programmed to simulate multiple stages of flocculation, for example in four stages of ascending mixing intensity, and alternately in four descending intensity over the identical but reverse order, all involving identical coagulant dosing conditions; thereby producing test result that should produce qualitative result useful for guiding full-scale testing planning.

In the foregoing, floc breakup can be defined as the size reduction of floc particles that can occur as the result of the non-uniform distribution of localized fluid shear across the entire 2-liter reactor volume. Areas of high shear may erode portions of newly formed floc that statistically eventually are exposed to elevated shear. Such shear spatial variations may result from large volume of tankage relative to mixing blade speed-surface area distribution and stationary baffle plates that further promote shear generation. Embodiments of the present invention can finally provide facility designers and operators with quantitative tools to empirically improve systems to achieve improved uniformity of shear and therefore floc formation, which improves pollutant removal and throughput performance.

In the foregoing, perikinetic flocculation can be defined as a particle-particle relative transport mechanism, also known as Brownian motion, operating in the sub-micrometer particle size range. Perikinetic flocculation occurs independently of fluid mixing. It is driven by the random thermal motion of individual water molecules striking suspended particles. So, this flocculation mechanism is not directly observable or measurable by embodiments of the present invention. However, perikinetic flocculation serves a vital function of ushering virtually all pollutant species—virus, bacteria, dissolved organic carbon, trace elements—into the size range of orthokinetic flocculation. Moreover, perikinesis can induce sub-micrometer (diameter less than or equal to $10^{-6}$ meter) pollutants to collide directly with significantly larger sub-millimeter (diameter less than or equal to $10^{-3}$ meter) particles thereby becoming part of floc volume that is measurable by embodiments of the present invention.

In the foregoing, orthokinetic flocculation can be defined as particle-particle collisions resulting from relative particle-particle movement and collision caused by the difference in velocity of adjacent fluid layers containing the particles, thereby causing particle-particle collisions that induce flocculation (floc size growth) at a rate proportional to the coagulant dosing controlled stickiness. Coagulant dosing is the sole control measure that plant operators have for influencing the stickiness of particles. The system 211 shown in FIGS. 13-18 is designed to specifically serve as a rapid-response measuring device of relative stickiness. This relative stickiness can be quantified by any one or a combination of $F_r$, $V_{c,mx}$, $D_{e,mx}$, $V_{c,s}$, $V_{\%}$, and $V_{c,mn}$, and $1/T_e$.

Mild fluid mixing simply promotes orthokinetic flocculation. Particle diameters of approximately 50 microns are a typical lower range of detection by embodiments using typical optical cameras and optics system commercially available at a reasonable cost today. This means that a portion of the lower end of flocculation ≤50 microns is not detected, processed, nor recorded. However, these under-sized (<50 micron) particles can rapidly grow into the ≥50-micron detectable size range as a result of particle collisions. This feeds the increasing magnitude of floc Volume Concentration, but at a rate that gradually diminishes as a steady-state flocculation-breakup balance develops.

In the foregoing, gravitational settling can be defined as the phase following the stopping of fluid mixing. Gravitational settling gradually increases as turbulence decays and the water sample becomes more quiescent, and the force of gravity acting vertically on suspended floc particles and overcomes the opposing random fluid motion forces. Satisfactory gravitational settling results are typically reflected in the rate and extent of the reduction in floc volume concentration in the coagulant and water mixture, as measured by $V_{c,s}$, $V_{\%}$, and $V_{c,mn}$.

Any of the operational metrics listed in Table 1 can be graphically presented in a manner similar to FIG. 22 to provide information that is useful for managing coagulant dosage for a water treatment or a wastewater treatment facility. First, because the coagulant in this case is one of the metal coagulants FeCl3 that largely (~93%-98%) forms an insoluble hydroxide precipitate, means that it would logically exhibit stoichiometry (or direct proportionality) with dosage. First, a linear correlation analysis of Vc,mx (maximum floc volume concentration) versus FeCl3 dosage for the data of FIG. 22 yielded a linear analysis expression of:

$$V_{c,mx} = 62 * DFeCl3 + 1279;$$

Where $R^2 = 0.98$ (where R is the correlation coefficient)

This high quality of an expression ($R^2 = 0.98$) infers that $V_c$ is a valid and reasonable surrogate variable of floc-particle concentration. This is evidence of the utility of this invention for use in optimizing coagulation-filtration water treatment. Second, an analysis of $F_r$ (initial perikinetic-orthokinetic floc rate) measured for each of the four dosages also yielded a high-quality linear correlation for each of the individual analysis. On the other hand, an analysis of the linearity of those individual floc rates versus FeCl3 dose yielded a moderate quality of correlation namely $R^2 = 0.72$. Third, qualitatively an inspection of the floc particle settling rates displayed in FIG. 22 likewise show a trend of improved settling quality that is proportional to the coagulant dosage. Thus, the case that quantitative floc particle growth and settling characteristics deriving from this invention offer significantly greater insight into the beneficial downstream processing effect and benefits of coagulation and are useful in its control. In conclusion, the six operational metrics listed in Table 1 above ($F_r$, $V_{c,mx}$, $D_{e,mx}$, $V_{c,s}$, $V_{\%}$, and $V_{c,mn}$) are shown to be valid, scientifically logical, measures of the relative goodness of the individual, distinct, and sequential processes of coagulation, flocculation, and settling-clarification for the purification of water. Moreover, as will be shown below in discussing FIG. 23, these metrics also server to forecast the relative effectiveness of the following process of filtration.

One significant benefit of the embodiment shown in FIGS. 13-21 is its ability to rapidly provide a user with the results of multiple comparative quantitative measurements that correlate with actual water (or wastewater) treatment plant full-flow flocculation-filtration system response to small changes in coagulant dosing (the plant operators "big lever" influencing filtration quality). The system 211 comprising the instrument 209 and chamber 210 described herein can provide numerous benefits to a water or wastewater treatment plant operator. Benefits can include orders of magnitude faster feedback, greater sensitivity, and an elevated degree of user confidence. Simultaneously and additionally, the embodiment shown in FIGS. 13-21 can reduce the risk of process quality upsets when compared to prior art water treatment and wastewater treatment process monitoring that relied on measuring filter-effluent turbidity. This far faster feedback results from the time difference between collection and rapid test of a small sample in the chamber 210 collected at the front end of the process (shown at 13D in FIG. 1, for example) versus the time it takes for process water in a treatment plant to pass from the coagulant addition stage (13D in FIG. 1) to the effluent stream from the filter (shown at 6 in FIG. 1, for example), the extreme downstream point in the process. The system comprising the instrument 209 and chamber 210 can perform the test in as little as 5 minutes whereas it may require up to some six hours for water to move from 13D to 6 in a typical water treatment plant. This is 72× fold faster feedback, which can significantly reduce off-optimum operating time.

FIG. 23 shows the relationship between coagulant dose, floc diameter, and filter effluent turbidity, as measured in Nephelometric Turbidity Units (NTU). The data in FIG. 23 were collected during a US drinking water industry sponsored test using an early prototype of the instrument described with reference to FIGS. 13-18. The test was run at a major university pilot facility located at an operating drinking water processing plant. Prior to the availability of embodiments of the present invention, instruments that measured filter effluent turbidity (and filter effluent particle counters) were the only on-line quantitative particulate metrics available for decisions regarding coagulant dose control. In the case of FIG. 23, the varying coagulant dosage is a polymeric coagulant species, variously referred to as pDMDAC or poly DADMAC, which stands for poly dimethyl diallyl ammonium chloride (along with a constant dosage of 9 mg/l of ferric chloride). Other examples of polymeric coagulant species that exhibit similar behavior can include cationic, nonionic, and anionic type polymers. These polymeric materials all produce a similar response of under dosing, optimum dosing, or over dosing as was shown in FIG. 23. By using the instrument and method described in FIGS. 13-18, the optimum polymer dosage can further include other polymer formulations such as:

(a) other polyamines;
(b) cationic polyacrylamides (DPAM);
(c) polyethylene-amines
(d) polyethylene-oxide; and
(e) sulfonated compounds.

The empirical relationship shown in FIG. 23 illustrates the linkage between coagulant dosage (the input variable of the X axis) and its related effect upon both filter effluent turbidity (solid line as measured in NTU) and average floc diameter (dotted line). This data supports a theory by Professor Charles O'Melia, who in 1971 proposed that both flocculation and floc-particle filtration effectiveness similarly respond to "stickiness" of floc particles, which, in turn, is controlled by coagulant chemical dosing.

The graph in FIG. 23, combined with the above stickiness theory, highlights an important observation made in an Einstein biography, namely "that science teaches us, very significantly, the correlation between factual evidence and general theories." This proof of concept verifies the practical value of the application of an instrument as illustrated in FIGS. 13-21 use for operational control of coagulation granular-media filtration systems. Secondly, this concordance of experiment and theory can teach decision makers, i.e., plant operators, that they can rely upon applying relative comparison measurement results of flocculation effectiveness to predict and control filtration performance. In turn, this can provide filtration drinking water plants with much needed capability to proactively optimize their filter performance for physically removing pathogenic organisms, especially *Cryptosporidium parvum*.

It is notable that an important strategy of drinking water industry is to provide multiple barriers to user exposure to pathogens involving the at least four distinct barriers; source water protection, physical removal by treatment, disinfection, and a secure distribution network protection. The present invention has the highest practical potential of any technology known today for individual granular-media-filtration facilities for optimizing the pathogen separation barrier, thereby bolstering drinking water safety independently of the subsequent barrier treatment process of disinfection.

Effectively, floc volume concentration, floc diameter, and filter effluent turbidity ($F_r$, $V_{c,mx}$, $D_{e,mx}$, $V_{c,s}$, $V_{\%}$, and $V_{c,mn}$, and $1/T_e$) serve as separate relative measures of coagulant dose relative stickiness. Embodiments of the present invention can be used to quickly and effectively find the dose of a coagulant that minimizes filter effluent turbidity and maximizes floc particle removal for a given input water chemistry in a water treatment plant or a wastewater treatment plant. It is worth mentioning that each turbidity point on the NTU scale displayed in FIG. 23 is the mean value of more than thousands of individual values. This translates to the fact that the difference between an NTU value of 0.041 and 0.043 is both significant and real, meaning that the 0.041 dosage truly represents optimum filter particle-removal performance.

FIG. 23 highlights a significant benefit of employing embodiments of the present invention, which allows a water or wastewater treatment facility to operate much closer to optimum coagulant dosage. This can be seen by the extraordinary disparity in sensitivity of floc characteristics (such as floc diameter $D_e$, the dotted line in FIG. 23) that can be measured by embodiments of the present invention versus filter effluent turbidity (the solid line in FIG. 23), which is the primary tool used in the prior art. In FIG. 23, the advantage of measuring floc characteristics is dramatically apparent, there is numerically close to a one million times greater sensitivity for floc diameter. Specifically shown in FIG. 23, a polymer dose change from 0.6 mg/l to 0.9 mg/l results in a floc diameter change from 373 μm to 227 μm (a 39% reduction) versus a filter turbidity increase from 0.041 to 0.043 (a 4.9% increase). Thus, floc diameter or volume concentration provides an operator with a superior yard stick for coagulant dose control: the results are more sensitive, and they are available far faster—within minutes of the start of the test versus hours required for a plant to process the water and measure turbidity after filtration.

These multiple significant improvements in the metrics for coagulant dosage control identified above can be obtained as a result of the numerous differences deriving from the use of the embodiment shown in FIGS. 13-21 versus the prior art systems and methods. FIG. 23 illustrates the effectiveness of contrasting metrics by showing the correlation, and contrast of floc diameter measurement (a front-end measurement performed by embodiments of the inventions disclosed herein) with filter effluent turbidity (a back-end measurement performed by the prior art) of processing. It is important to mention that turbidity has rightfully evolved as the de facto standard metric for drinking water particulate quality, typically installed at the back end of every plant filter, and monitored at the back end of the plant as the plant's CFE (combined filter effluent). The evolution of low range turbidity standards has been the foundation of this development. The role of turbidity as a measure of drinking water quality can be thought of as "the supreme court" of regulatory quality. However, turbidity is a marginally suitable metric for coagulant dose control because of the turbidity noise inherent in the mechanical system in filtration—hydraulic bumps related to filter back washing causing momentary particle breakthrough, breakthrough at the end of filter runs, an unavoidable remnant of particulate carryover at the end of filter back wash—and the fact that high quality performing plants produce very low turbidity values approaching the third decimal NTU (Nephelometric Turbidity Unit) range and approaching its lower end of sensitivity range.

Again, referring to FIG. 23 it is important to note that in the context of the broader range of this polymer dosage regime, that turbidity sharply increases—as is the case commonly with polymers generally—likewise implying that the risk for pathogen removal by filtration sharply declines outside this relatively narrow optimum-dose zone. Finally, it must be noted that virtually all high performing filtration plants today, employ dual coagulant chemicals which is an essential prerequisite for effective flocculation and filtration. The use of dual coagulants starts with a metal coagulant such as a Ferric+++ or Aluminum+++ salt for achieving the necessary task of neutralizing all opposing or negative charge demand deriving primarily form organic carbon acid groups as measured by TOC-DOC (Total Organic Carbon-Dissolved Organic Carbon) analysis. These metal coagulants are typically called hydrolyzing metal salts (HMS). Secondly, a polymer is also added, preferably after a delay time following initial floc formation from the metal. Significantly, all polymers effect floc formation similarly to FIG. 23 with a chevron stripe peaked shape. Therefore, they absolutely need to have the dosage optimized. Note also, any time the metal dosage is changed, e.g. in response to a TOC (total organic carbon) raw water change, it is necessary to also re-optimize polymer dosage for peak filter performance. Effectively optimizing both metal and polymer dosing is a never-ending job, especially for plants experiencing changes in raw water chemistry. This reality is especially critical for plants that may experience rapid changes such as occurred at Milwaukee Wis. in their *Cryptosporidium* disaster of 1993.

FIG. 24 shows a decision table for determining how to change polymeric coagulant dosing to improve coagulation/flocculation performance. Referring first to FIG. 23, and the floc diameter dashed curve, and noting that following analysis of an initial sampling sequence and one obtains a floc diameter of, say, 2,000 microns. It is unknown whether this result on the rising or descending part of a curve that should resemble FIG. 23. It is therefore necessary to make a random choice to either increase, or decrease the polymer dosage by, say 2-10%. Once the second result is available, the dosage rules shown in FIG. 24 begin to apply in order to systematically ascend to the peak. The table shown in FIG. 24 is built on the logic that it must apply to any two sequential dosed sample results that are relatively close and reflect a significantly different floc-diameter change. Because there are 2 possible dose changes, increase or decrease, and two possible outcomes, larger or smaller floc diameter, there are $2^2=4$ possible outcomes as reflected in the table of FIG. 24.

An example decision sequence for illustration follows involving a different plant, raw source water, optimized metal coagulant dosage that remains constant, and a different polymer species. For a dosage of 1 mg/l the maximum mean floc particle diameter found equaled 200 um. A second dosage of 0.9 mg/l was chosen and the corresponding floc diameter found equaled 150 um. These conditions of decreased dosage and smaller floc diameter corresponds to the top row (Increased Dosage) shows that the relative position of this sample sequence is clearly on the right-hand or descending side of a response curve, like the graph shown in FIG. 24. The strategy for finding the peak or optimum value is to continually decrease the dosage until the floc diameter begins to decrease; which indicates that the optimum is at a lower dosage can subsequently be found by dithering the dosage values below and above the indicated maximum region (where dither means to sequentially change process polymer dosage alternately above and below the suspected optimum dosage).

A significant strategy for detecting changes in raw water quality and an indicated related need for a corresponding coagulant(s) dosage(s) change is inherent in a continued dose dithering sequence, at an appropriate time interval. Such an action could especially be of benefit where raw water changes present operational challenges to continuously meet effluent turbidity goals. A dose dither strategy in combination with the decision table of FIG. 24 foretells that such a strategy is amenable to evolving a software based automated or semi-automated coagulant dosage control system, as the value of dose dithering becomes more widely detected.

The decision rules shown in FIG. 24 can be implemented as part of a never-ending process. This might be done if embodiments of the systems and methods described herein are used for continuous monitoring and process control. The decision rules shown in FIG. 24 can also be used in a process that ends when the differences in floc particle characteristics (such as floc size) between subsequent tests is sufficiently small that it is not worth performing further tests to more precisely optimize coagulant dose. It should also be noted that the decision table shown in FIG. 24 could be used for optimizing the dosing of any coagulant species, including, but not limited to Hydrolyzing Metal Salts (HMS) and polymer coagulants.

Figure 25:
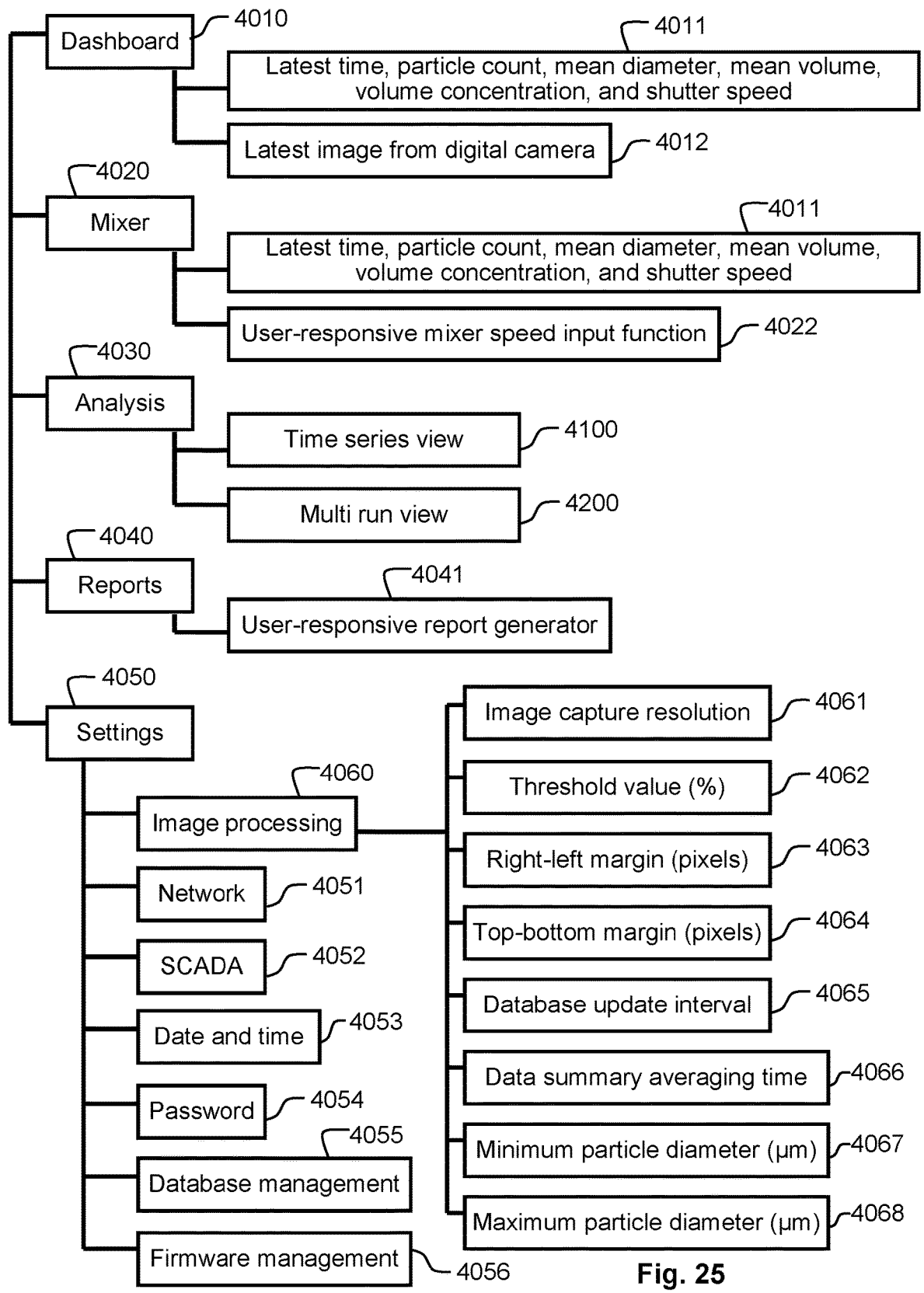
FIG. 25 shows some of the user interface functions in the system and method shown in FIGS. 13-21.

FIG. 25 shows some of the user interface functions in the system and method shown in FIGS. 13-20. Referring to FIG. 25, the five main functional areas in which a user can interact with the instrument and method of FIGS. 13-20 are: viewing a dashboard 4010; managing the mixer 4020; viewing an analysis of test data 4030; generating reports 4040; and managing various settings 4050. These five main functional areas can be accessed by a menu, such as the menu shown at 4101 in FIG. 26 and FIG. 27. This menu can be visible on all screens of an embodiment of the system and method shown in FIGS. 13-20. One or more of the user interface screens can also display time on the x-axis versus y-axis values of particle count, mean diameter, mean volume, and volume concentration ($n_c$, $D_e$, $V_i$, and $V_c$) as shown at 4011, and as were discussed with reference to Table 1. The shutter speed of the digital optical camera can also be part of this status information 4011. An example of this status information on a user interface screen is shown at 4011 in FIG. 26 and FIG. 27.

Referring more specifically to some of the functionality in FIG. 25:
 (a) The dashboard screen 4010 can further comprise a latest image from the digital camera, which shows the floc particles 4012;
 (b) The mixer screen 4020 can further comprise an input function that allows the user to control mixer speed 4022; and (c) The reports screen 4040 can further comprise a user-responsive report generator 4041. The reports can be in a variety of formats including delimited text file such as CSV (comma separated values file) or Excel (MicrosoftTRADE ExcelTRADE compatible file), and text. The system can be configured to allow the beginning and end dates and times to be selected by the user.

The settings functionality 4050 in FIG. 25 can be used to manage many of the system settings for an embodiment of the present invention as described with reference to FIGS. 13-20. These settings 4050 can include network settings 4051, SCADA (which stands for "supervisory control and data acquisition") system settings 4052, time and date settings 4053, password settings for access to the system 4054, database management settings 4055, and firmware management settings 4056. These settings can also include image-processing settings 4060. The image processing settings 4060 can include:

(a) image capture resolution 4061 for the digital camera, which can be specified in horizontal pixels and vertical pixels or by a selecting a category (such as high, medium, and low), (b) floc image threshold values 4062 for discriminating between the lighter floc particles and the darker background in an image, which can be specified as a percentage of full pixel intensity;

(c) right and left margin values 4063, which are regions of on the right and left edges of the images captured by the digital camera that can be ignored when processing the image, and can be specified in pixels, which can be used to change the size of the processed image or to exclude some peripheral image features;

(d) top and bottom margin values 4064, which are regions of on the top and bottom edges of the images captured by the digital camera that can be ignored when processing the image, and can be specified in pixels;

(e) database update interval values 4065, which identifies the frequency at which data in volatile (random-access) memory is written to the non-volatile removable solid-state memory that was shown at 212 in FIG. 13 and FIG. 21;

(f) data summary averaging time values 4066, which, are time moving averages (a smoothing function) of floc particle count $n_c$, equivalent average spherical floc particle diameter $D_e$, computed floc particle volume $V_i$, and/or floc volume concentration $V_c$;

(g) minimum particle diameter to detect 4067; and (h) maximum particle diameter 4068 that will be used in the calculations for floc particle count $n_c$, equivalent average spherical floc particle diameter $D_e$, computed floc particle volume $V_i$, and/or floc volume concentration $V_c$.

In one embodiment, the minimum particle diameter to detect (4067 in FIG. 25) can be managed in the following way for the following reasons:

(a) Internal constants can be used to define the spatial coverage of the optical system. These constants can be determined by observing the image of a reference grid, placed in the center of the sample volume. This can also be also used to adjust and verify the camera's lens is set to focus in the correct focal plane.

(b) Using a reference grid and existing optics, the dimensions of the pixels in each direction can be established. These dimensions can be used to compute the area (in micrometers per pixel, for example). Feature extraction utilizes can be performed by identifying Binary Large Objects (BLOBs) in digital imagery. In short, the BLOB algorithm can be used to identify regions in the image that contain connected pixels whose intensities are above the user-selected thresholds.

(c) In one embodiment, a simple box classifier can be used to establish masking geometries for the algorithm. Fundamentally, the algorithm is a contour based computation. The contour threshold is established by empirical observation of the images of test samples. Default and initial contour thresholds are provided which produce satisfactory results over a wide range of sample conditions.

(d) The area of the BLOB (within the contour) can be computed using a minimum of 2 adjacent pixels. The diameter can be modeled in this implementation using the function: $2*sqrt(A/Pi)*\mu m$ per pixel, where A is the area in pixels and µm per pixel represents the scaling constants mentioned above.

(e) In one embodiment, the computations are done using a single thread, and the number of image frames that can be analyzed in a fixed period of time is limited by the performance of the CPU. Image samples are collected and analyzed at the rate the CPU allows. Increasing the digital image resolution (and therefore the minimum particle diameter to detect 4067) decreases the number of samples used to compute the statistical averages within the selected data collection interval. In one embodiment, the user of the instrument can control the image resolution, particle size thresholds and data collections intervals to maximize the value of the data in disparate conditions.

The analysis functionality 4030 in FIG. 25 can best be understood by noting that there can be two types of analysis screens: a time series view 4100 that will be explained in greater detail with reference to FIG. 26 and a multi run view 4200 that will be explained in greater detail with reference to FIG. 27.

Figure 26:
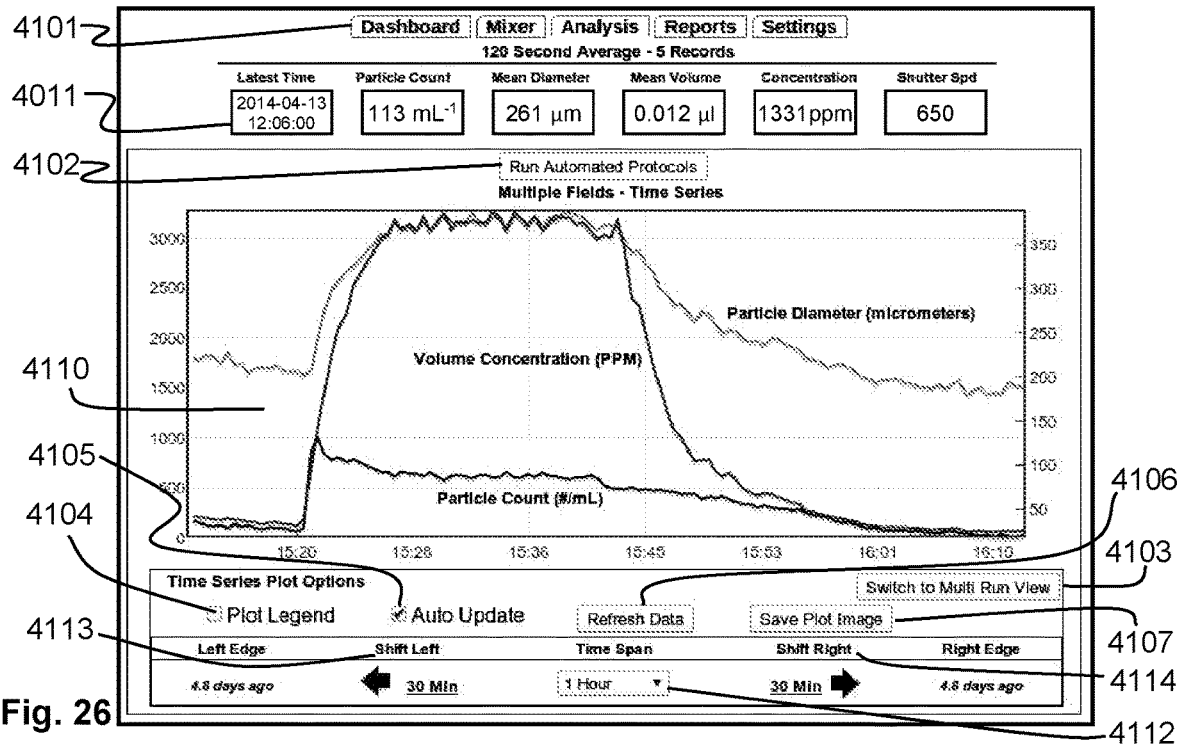
FIG. 26 shows an example of a time series analysis screen for the system and method depicted in FIGS. 13-25.
Figure 27:
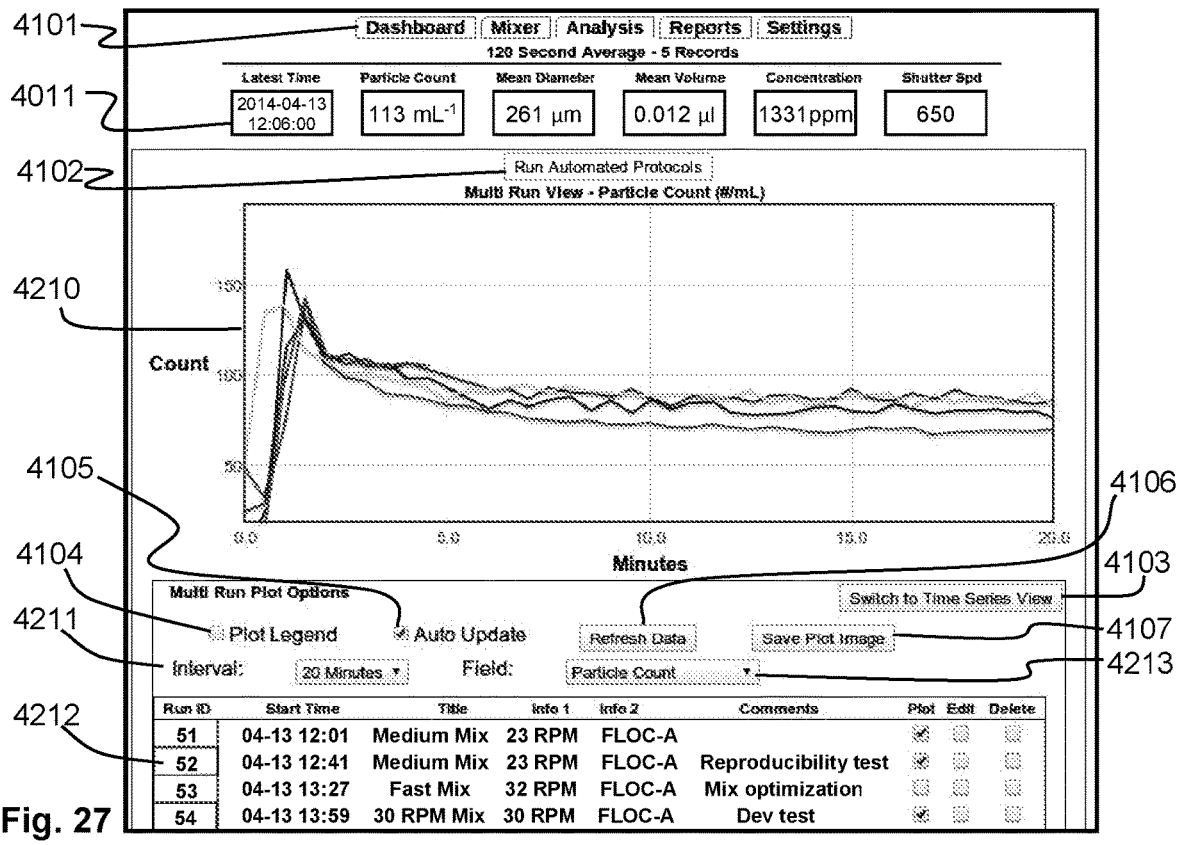
FIG. 27 shows an example of a multi run view analysis screen for the system and method depicted in FIGS. 13-25.

The analysis displays shown in FIG. 26 and FIG. 27 comprise:

(a) a menu 4101 for accessing the other functions (Dashboard, Mixer, Reports, and Settings) that were discussed with reference to FIG. 25;

(b) the status information 4011 (Latest time, Particle count, Mean diameter, Mean volume, Concentration, and Shutter speed) that was also discussed with reference to FIG. 25;

(c) an automated protocols button 4102 to access programming functionality that was described with reference to steps 3100 and 3022 in FIG. 34 and all steps in FIG. 20;

(d) a toggle button 4103 that allows the user to toggle between the time series view of FIG. 26 and the multi-run view of FIG. 27;

(e) an option to plot the legend 4104 on the visible image so legends will appear in the saved image;

(f) an option to automatically update the plot with the passage of time, which keeps the plot current with the latest data being appended to the database file collected since the prior update 4105;

(g) an option to refresh the data screen to the most current set of data values 4106, which ensures that the data displayed is the most recent data available; and (h) an option to save the current displayed image as a graphics file 4107, thereby capturing a snapshot of conditions at a specific more moment for later use in reporting, documentation, training, or other actions. The option to save the current displayed image can initiate a save file dialog box that can present a default file name and time stamp. This file dialog box can allow the user to select the proper folder and edit the file name before activating "save" and/or "cancel" buttons to finalize the action.

The main graph in the time series view of FIG. 26 shows multiple parameters of the sample during a test (in this case volume concentration, particle diameter, and particle count) as a function of time in the graph at 4110. This compound plot allows the user to simultaneously view an overlay of multiple parameters during one test run. Options can be provided to change the visible characteristics of the plot. The options shown in FIG. 26 allow the user to select appropriate plot time scales 4112, and move the data being displayed leftward 4113 or rightward 4114 in time. The effect is to magnify or shift the x-axis time scale by doing the following:

(a) Selecting a time span using a selection button 4112, set at 1 hour in the example screen shown in FIG. 26. By choosing a shorter time span, the user can zoom in on what happened during a particular stage of the coagulation-flocculation-settling process.

(b) Shifting the window of what is being shown on the graph left 4113 or right 4114 by a fixed distance in time. By clicking on the arrow below shift left or below shift right, the user can move the display 50% of the current time span to either the left (earlier) or the right (later) to pan through the graph that has a higher resolution on the x-axis time scale.

The main graph in the multi run view of FIG. 27 shows a comparison of one sample parameter for a plurality of tests performed by an embodiment of the system and method described herein. Thus, the multi run graph 4210 is similar to the graph that was shown and discussed with reference to FIG. 22. As shown at 4212, the user can select which runs to plot, edit, or delete. As shown at 4211, the user can specify the plot interval (time from start to end of the plot) and the user can select which parameter to plot 4213. Common parameters to plot are volume concentration $V_c$, particle diameter $D_e$, and particle count $n_c$. Parameters derived from $V_c$, $D_e$, and $n_c$ (such as $F_r$, $V_{c,mx}$, $V_{c,s}$, $V_{\%}$, and $V_{c,mn}$) could also be plotted.

FIG. 28 shows an example of a user interface screen for performing step 3006, performing step 3022, and initiating step 3100 in FIG. 19. In one embodiment, the information shown in FIG. 28 pops up when the "Run Automated Protocols" 4102 button in FIG. 26 or FIG. 27 is clicked by a user. As shown in FIG. 28, the user can select a mixing protocol (i.e. select a test protocol as described in step 3006 in FIG. 19) by choosing one of the options provided by a selection button shown at 4301. The interface user screen shown in FIG. 28 can include a summary of the chosen test protocol by listing stages, comments about each stage, duration of each stage, and mixer speed during each stage, as shown at 4302.

Further referring to FIG. 28, the user can start a test by clicking the "Start run" button 3022A, and can stop a test by clicking the "Stop/Abort run" button 3022B, which corresponds to performing step 3022 in FIG. 19. The user can also name the test by giving it a title 4303. The user can describe the chemistry of the test 4304. The user can describe the chemical dosage for the test 4305. The user can select the length of the recording period 4306 and specify a delay before recording commences 4307. The user can add other comments about a specific test 4308. The user interface shown in FIG. 28 can also comprise run status information 4309, such as the current stage of the test that is occurring, the speed of the mixer, and the time since the test stage began.

If the desired protocol for a test is not created and available among the information in FIG. 43 (a decision shown at 3004 in FIG. 19), the user can choose to create a new protocol 3100 (a process shown at 3100 in FIG. 19 and the entire process that is shown in FIG. 20). More specifically, clicking the "Create new protocol" button, 3100 in FIG. 28, initiates the process shown in FIG. 20. In one embodiment, clicking the "Create new protocol" button 3100, shown in FIG. 28, causes the information shown in FIG. 29 to pop up.

FIG. 29 shows an example of a user interface screen for performing steps 3106, 3108, 3114, 3116, and 3124 in FIG. 20 (i.e. editing an experimental protocol). The test protocol (or mixing protocol) can be given a name or title 4403. Default information for the run chemistry 4404, run dosage 4405, recording period 4406, and recording delay 4407 can be entered. Comments 4408 about the test protocol (or mixing protocol) can also be entered. The user interface screen shown in FIG. 29 can also include a summary of the stages in the test protocol (also called a mixing protocol or experimental protocol) as shown at 4410. The user can select a stage to delete, 3114 in FIG. 20. The user can click a button to add a stage, 4411 in FIG. 29, which can cause a default stage definition to appear as a popup like that shown in FIG. 30. The user can choose to edit a stage by checking a box 4412, which can cause that stage definition to appear as a popup like that shown in FIG. 30. The user can save a protocol 3124 in FIG. 20 by clicking a button, 3124 in FIG. 29, which can cause the database storing the experimental protocol (also called a mixing protocol or test protocol) to save this information onto the removable non-volatile solid-state memory that was shown at 212 in FIG. 13.

FIG. 30 shows an example of a user interface screen for performing step 3120 in FIG. 20. This screen can be used to provide a title, label, and/or comment for a stage 4501. It can be used to specify the duration of the stage 4502. It can be used to specify the speed of the mixer 4503, or specify that the mixer is turned off, by placing a zero in the mixer speed. When the user is finished, the information for this stage can be updated 4504 and the user can return to the protocol editor, shown in FIG. 29.

Clicking anywhere on the plot 4110 (in FIG. 29) can initiate the process of collecting user annotations (i.e. explanatory text input from the user). A text input box is exposed with save and cancel options. User entered annotations can be stored in the removable non-volatile solid-state memory that was shown at 212. The presence of predefined real-time user-written annotations in the database can be indicated by the presence of small marker circles on the X-axis (i.e. real-time axis) of the graphically displayed data on the touch screen 190. These annotations can be indexed by time in the database and selectively retrieved by limiting the search to the temporal limits of the time series plot. The index can be established using the plot X coordinate, which corresponds to the specific time. These annotations can be used to record:

(a) Details regarding test conditions, such as dosage(s) of coagulant(s), pH, temperature, mixing speed(s), main process flow rate, and/or other process changes that could influence test results;

(b) User-provided test objectives and/or observations, such as "this is an encouraging trend we have never observed before" or "I think we are still overdosing despite what our previous experience shows"; and/or (c) Observations of one operator on one shift, to be passed to an operator on a next shift of the events and conditions that occurred during the shift.

Referring generally to the system described with reference to FIGS. 13-30, this system could be implemented using a client-server architecture in which the single-board computer, 198 in FIG. 21, acts as a web server. The web server can run an industry standard operating system such as Linux. It can have an industry standard web server such as the Apache Web Server. It can work with an industry standard database, such as MySQL, and the computer code can be written using a programming language such as PHP or Perl. The touchscreen display, 190 in FIG. 21, can be configured to display a web browser that acts as the client. This type of architecture is known by the acronym LAMP, which stands for Linux-Apache-MySQL-PHP (or Perl or Python for the "P"). Such a system can also be connected into a plant-wide SCADA (supervisory control and data acquisition) network.

The laboratory system 211 and method described herein could also comprise pumps, tubing, and valves connected within a water treatment plant as illustrated in FIG. 10 and related discussions. Such a system is capable of performing a similar action without direct human involvement for executing the sample processing, refreshing, sample preparation, acquisition, processing, and analysis, in order to achieve more automated testing, analysis, and perhaps limited coagulant dosing control.

A variety of control methodologies can be used to evaluate the optimum dosage and mixing speeds to meet treatment facility targets, such as proportional-integral-derivative (PID) control, fuzzy logic, or adaptive systems such as neural networks or generic optimization algorithms. Additionally, artificial intelligence (AI) is emerging as a practical tool for learning from large databases such as the databases that are common in modern water treatment facilities. Accordingly, AI may be applicable for establishing an individual plant relationship as shown in FIG. 23 between floc formation and filtration effectiveness. It is anticipated that the optimal control values may change frequently because raw water quality may change due events outside of plant operations control, such as weather events, man-influenced events such as an upstream diversions or discharges. This variation of input water quality necessitates that the side-stream coagulation-flocculation optimization system continuously operates to find ever-changing optimum control outputs.

Figure 31:
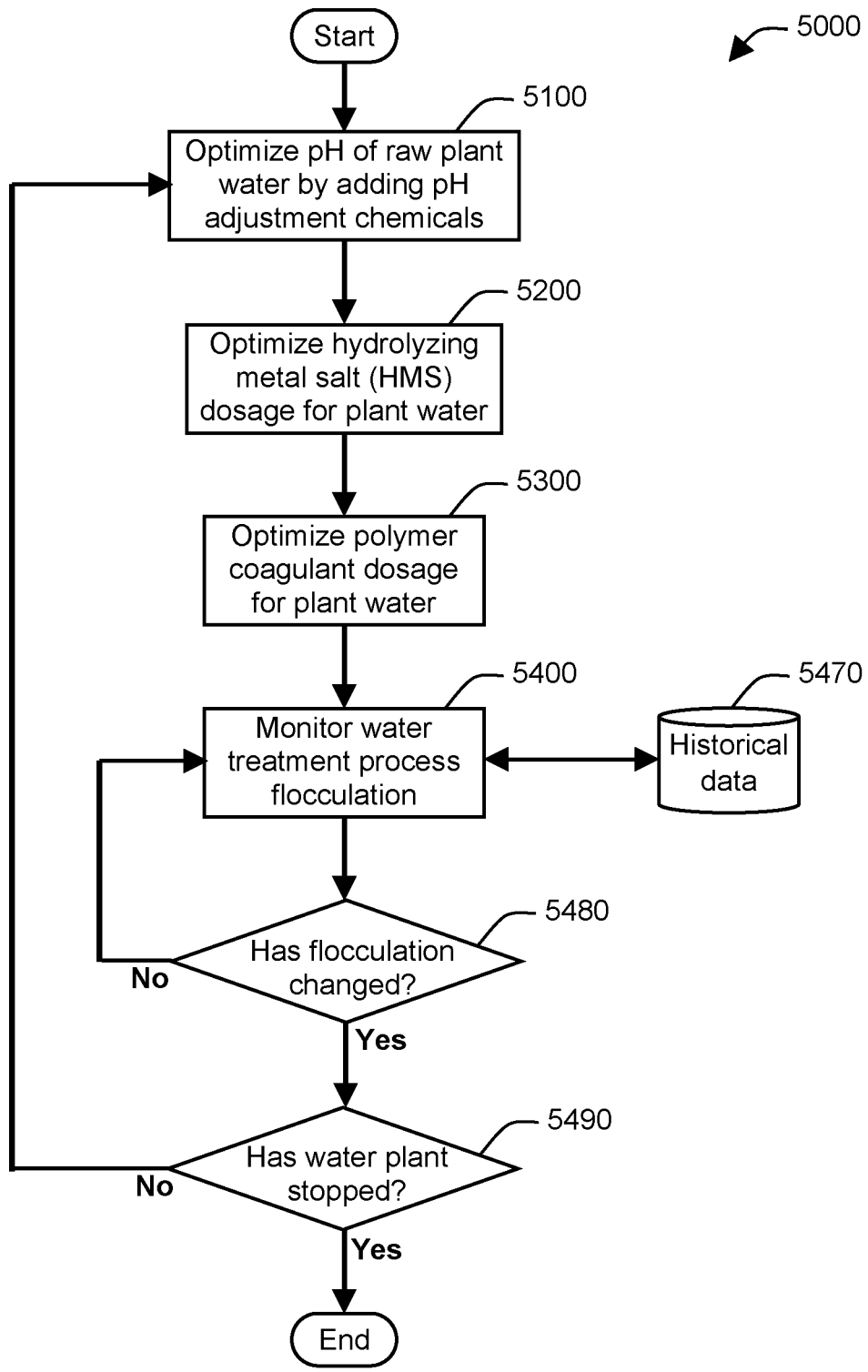
FIG. 31 shows a method for optimizing water treatment coagulant dosing.
Figure 32:
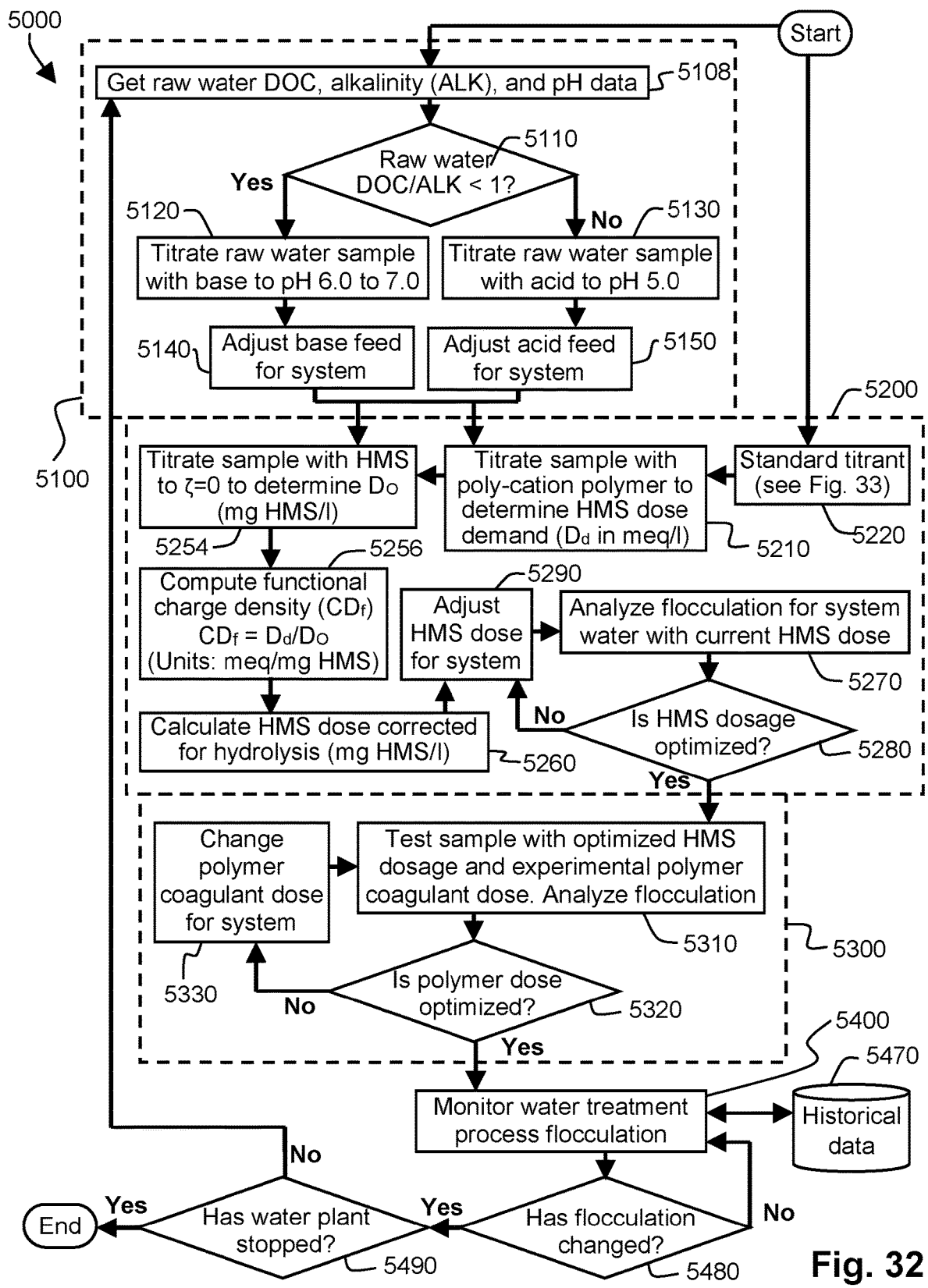
FIG. 32 shows the method of FIG. 31 in more detail.
Figure 33:
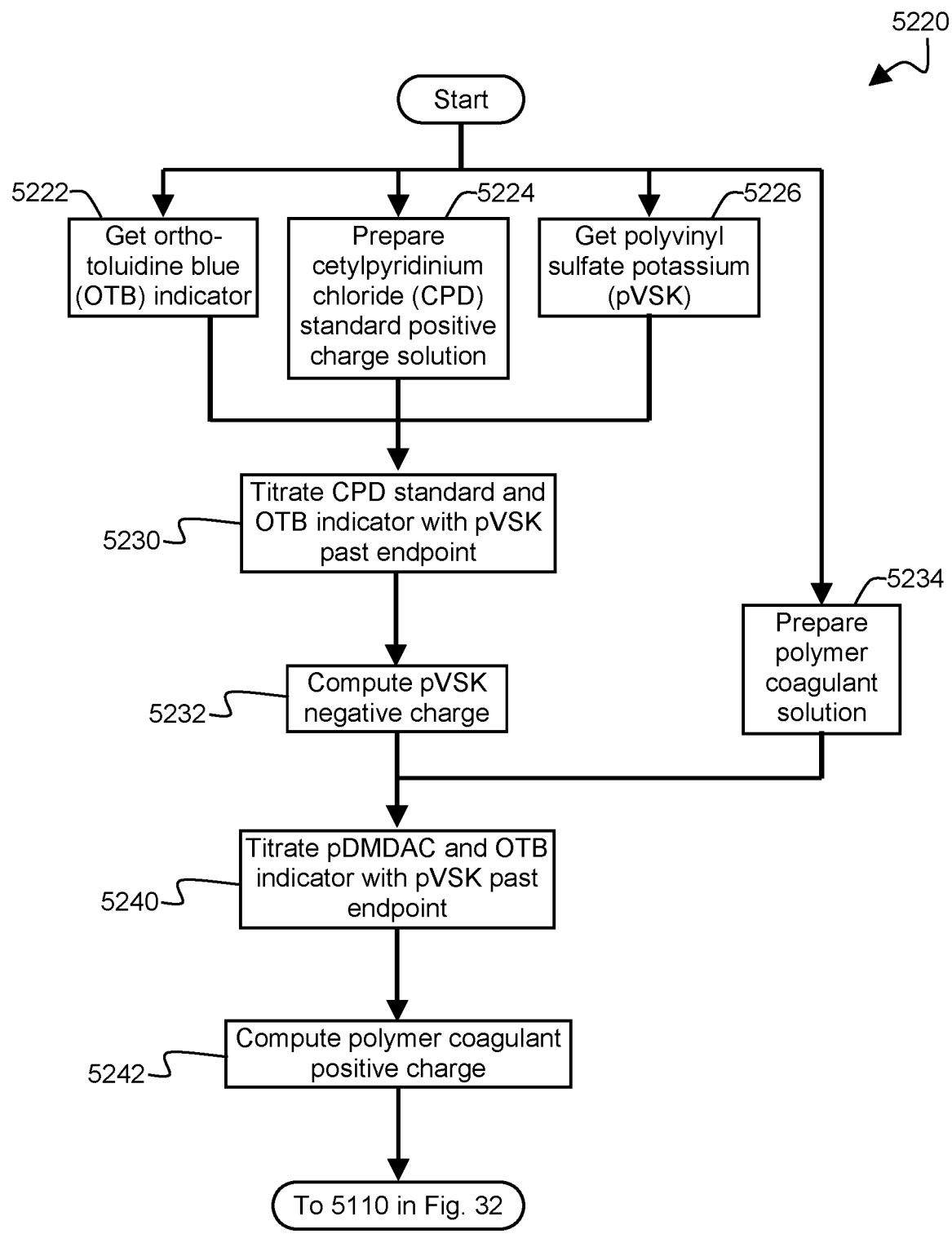
FIG. 33 shows a method for generating a standardized pDMDAC titrant.

FIGS. 31-33 show a method for optimizing water treatment coagulant dosing. The method 5000 shown in FIG. 31 and FIG. 32 comprises the following steps in the following specific sequence:
  (a) Determining the optimal acid-base dosage to be added to the raw plant water in the form of pH adjusting chemicals to optimize the pH of the raw water entering the plant, a step shown at 5100;
  (b) Determining the optimal dosage of hydrolyzing metal salt (HMS) to be added to the pH adjusted raw plant water and adding this dosage to the pH-adjusted raw plant water, a step shown at 5200;
  (c) Determining the optimal dosage of polymer coagulant to be added to the pH-adjusted and HMS optimized plant water and adding this dosage to the pH-adjusted and HMS optimized plant water, a step shown at 5300; and
  (d) Monitoring the flocculation of the plant water after performing the previous steps to determine if flocculation has changed, steps shown at 5400 and 5480; and
  (e) Recycling through the previous steps 5100, 5200, and 5300 if the flocculation has changed and the water treatment process is still operating.

Each of steps 5100, 5200, and 5300 is a local optimization of one chemical species addition to the raw water input as part of a water treatment process. The combination of these three main steps in the order disclosed herein facilitates the global optimization of a chemical addition process for water treatment.

Referring in more detail to step 5100 in FIG. 31 and FIG. 32, pH is referred to by aquatic chemistry professionals as the master variable of water chemistry. This is especially the case in processes utilizing trivalent hydrolyzing metal salt (HMS) coagulant chemicals such as alum and ferric preparations. Higher solution pH values (pH >8) can nullify the ability for an HMS to develop various charged species because higher solution pH values can accelerate the elimination of HMS' positive charge to hydrolysis before the HMS has much opportunity to react with the negatively charged pollutant particles, and thereby failing to completely neutralize raw-water's total negative charge. Alternatively, low pH values (pH<6) can retard hydrolysis and enabling complete pollutant charge neutralization. This may occur as more of the labile, short lived positive hydrolyzing metal salt (HMS) species react with the target negatively-charged pollutant species; as is essential for effective coagulation-flocculation and filtration and pollutant removal. Thus, the management of pH is an essential first step for the optimization of water treatment processes. As will be discussed later herein, the measurement of dissolved organic carbon (DOC) and alkalinity are essential for computing the amount of acid and/or base (pH adjustment chemicals) to be added to change pH of the raw water entering a water treatment system to a target range.

Referring in more detail to step 5200 in FIG. 31 and FIG. 32, this is the critical and most influential processing step in optimizing subsequent water filtration of pollutants including amoeba, bacteria, and virus, acidic natural organic matter (NOM), organic and mineral colloids that all possess acidic ionizable negatively charge groups on their surface. Negative charge produces mutual repulsive forces that prevent agglomeration needed for sedimentation and removal. Optimized HMS dosing achieves numerous important roles in successful drinking water filtration pretreatment. In optimized HMS coagulation these include:
  (1) Raw-water charge-neutral dosing, defined by floc particle charge reduced to a target $\zeta=\sim0$ mV, where is the zeta potential or floc particle charge measured in millivolts;
  (2) Creation of visible sticky macro-agglomerates of floc-particle-pollutants that accelerate floc particle formation, largely composed of the core Al or Fe hydroxide precipitates; and
  (3) The increase of pollutant particle diameter by up to $10^7$ magnitude diameter change, a 10-million-fold increase in particle size diameter, which enables pollutant separation from water by effective relatively low-cost physical means of gravitational settling and granular media filtration.

Referring in more detail step 5300 in FIG. 31 and FIG. 32, the objective of this step is to determine the optimum polymer coagulant dosage in the full water treatment process. Extensive experience with granular-media filtration pretreatment coagulation points to use of dual coagulants: (1) HMS first followed by (2) subsequent addition of a cationic polymer or poly-cation such as pDMDAC (Polydiallyldimethylammonium chloride). Polymer coagulant addition at this point in the process compliments HMS coagulation by forming floc that is stronger, denser, better settling, and easier to filter. The relationship between polymer coagulant dose and floc diameter is a chevron or inverted V pattern with a clearly identifiable optimum, as was shown in FIG. 23. This coagulant dose optimum can be found using a dose dithering process that was described with reference to FIG. 24. By analyzing full-process polymer dosed samples for flocculation effectiveness the dosing control can be fully automated.

It should be noted, that the dose dithering process for polymer coagulant that was shown and described with reference to FIG. 23 and FIG. 24 can also be used to facilitate the optimization of hydrolyzing metal salts (HMS) dosage (step 5200 in FIG. 31, FIG. 32, and FIG. 35), prior to using this method to optimize polymer coagulant dosage.

Further referring to FIG. 31 and FIG. 32, once the raw water pH has been adjusted (step 5100) and the HMS and polymer coagulant dosages have been optimized (steps 5200 and 5300), the water treatment process can be monitored to ensure that it stays in control, as shown in step 5400. This process monitoring 5400 typically involves storing and retrieving historical data 5470 and comparing current data to historical data to identify whether any changes in plant performance are statistically significant indicators that require the optimization process (steps 5100, 5200, and 5300) to be performed again. This performance monitoring can comprise monitoring of flocculation. The floc characteristics to be monitored in step 5400 can comprise: floc number concentration per unit volume; individual floc-particle volume; mean floc particle volume concentration per unit volume; and mean floc particle diameter assuming spherical. The floc characteristics to be monitored in step 5400 can also comprise: floc particle growth rate; maximum floc particle diameter; rate of settling of floc-particle-volume concentration; and extent of settling of floc-particle-volume concentration. These floc characteristics were discussed earlier in this document. The historical and current floc characteristics, such as those describe herein can be used to determine whether flocculation has changed, a step shown at 5480, in FIG. 31 and FIG. 32.

The methods used for determining whether flocculation has changed can be any method capable of being understood by anyone skilled in the art. For example, floc characteristics of the type described herein can be control charted based on statistical parameters such as mean and standard deviation. In this case, the definitions of "in control" and "out of control" will correspond to statistical confidence limits. If, based on these methods, or any others capable of being understood by anyone skilled in the art, the flocculation has not changed, the water treatment monitoring process 5400 continues. If the flocculation has changed and the water plant has stopped operating, the process ends. If the flocculation has changed and the water plant is continuing to operate, the process repeats starting with a re-optimization of the of the acid-base dosage to adjust raw plant water pH, as shown at 5100.

Box 5100 in FIG. 32 provides further detail of one method for optimizing the acid-base dosage and adjusting raw plant water pH. The steps shown in box 5100 address a seminal aspect of the control of today's predominately used coagulation process for achieving cost effective coagulation-filtration removal of drinking water pollutants. An up-front issue of this broader process concerns the existing pH of the raw water and the associated and negative charge demand relative to the additive HMS coagulant's, conditional efficiency and dosage necessary to supply the opposing positive charge neutralizing capacity. The optimum numeric solutions reflected in step 5110 for best dealing with the extreme ends of this spectrum of challenges can be provided by calculating the ratio of raw water DOC (dissolved organic carbon) divided by ALK (alkalinity or reservoir of buffering capacity of $HCO_3^-$ and $CO_3^{-2}$).

Referring in greater detail to box 5100 in FIG. 32, the process begins by getting chemical information for the raw water to be treated, as shown at 5108. In a water treatment facility, this information is typically tracked by monitoring equipment attached to a plant network using a SCADA (supervisory control and data acquisition) system. The specific raw water chemical information needed can comprise dissolved organic carbon (DOC), alkalinity (ALK), and pH, as shown at 5108. Note that in some cases, total organic carbon (TOC) can be substituted for DOC data. This DOC and alkalinity (ALK) data can then be used to determine what type of pH adjustment chemical must be added to the raw water (either a base or an acid) in the treatment process, a step shown at 5110. More specifically, a base should be added if DOC/ALK is less than 1.0 and an acid should be added if DOC/ALK is greater than 1.0. If a base must be added, the rate at which base must be added to the raw water is determined by a base titration 5120 and the target system pH is typically in the range of 6.0 to 7.0. The base feed of the system is then adjusted in step 5140 using the value determined in step 5120. If an acid must be added, the rate at which acid must be added to the raw water is determined by an acid titration 5130 and the target pH is typically about 5.0. The acid feed of the system is then adjusted in step 5150 using the value determined in step 5130.

It should be noted that an alternate way to maintain the optimal pH of the raw water in step 5100 in FIG. 31 and FIG. 32 would be to measure the pH of the plant water after pH adjustment chemicals have been added (at the end of step 5100) using a closed loop controller in which the dosing of the pH adjustment chemicals is modified in response to changes in the measured pH of the plant water at the end of step 5100 in FIG. 31 and FIG. 32. In this case, steps 5140 and/or 5150 will be responsive the measured output pH and steps 5110, 5120, and 5130 do not need to be performed as frequently, if at all.

Box 5200 in FIG. 32 provides further detail of one set of actions that can be performed after the pH adjustment step shown in box 5100. Specifically, once pH has been optimized, the next step in the process is to optimize the rate at which hydrolyzing metal salts (HMS) are added to the water to be treated. In one embodiment, the optimization of HMS dosage in box 5200 starts with:

(a) A standardized titrant 5220, which can be obtained using the method described with reference to FIG. 33;

(b) Titrating a sample of the pH adjusted raw plant water from box 5100 with the standardized titrant 5220 (a poly-cation polymer) to a zeta potential ($\zeta$) of approximately 0 mV determine the raw water charge demand ($D_d$) expressed in units of miliequivalence per liter (meq/L), as shown at 5210; and (c) Titrating a sample of the pH adjusted raw plant water from box 5100 with a hydrolyzing metal salt (HMS) coagulant to a zeta potential ($\zeta$) of approximately 0 mV to determine an HMS coagulant dose demand ($D_o$) expressed in mg of HMS per liter (mg HMS/l), as shown at 5254.

Zeta potential ($\zeta$) of the titrated samples in steps 5210 and 5254 in FIG. 32 can be measured using any device for measuring electrophoresis of a water sample, one example of which is the NanoBrook ZetaPlus sold by Brookhaven Instruments. A zeta potential of approximately 0 millivolts is also sometimes referred to as a point of zero charge (PZC). Note that some practitioners prefer a target zeta potential that is slightly negative, others prefer a target zeta potential that is slightly positive, and still others prefer getting the zeta potential as close to 0 millivolts as possible.

Once the HMS dose demand $D_d$ (in meq/L) has been determined in step 5220 and the HMS dose ($D_d$) needed for a zeta potential ($\zeta$) of approximately 0 mV has been found in step 5254, the ratio of the functional charge density ($CD_f = D_d/D_O$), measured in units of miliequivalence per milligram of hydrolyzing metal salt, can be calculated, as shown at step 5256. Stated another way, steps 5210 and 5254 compute the necessary HMS dosage system additive value (mg HMS/L). The results of steps 5210, 5254, and 5256 can then be used as inputs for the adjustment made in step 5260, where the HMS dose is corrected for hydrolysis. The result of step 5260 (in milligrams of hydrolyzing metal salt per liter of water) can then be adjusted for the pH adjusted raw plant water, a step shown at 5290.

Having changed the HMS dose for the system, a sample of system water can be analyzed to determine flocculation, a step shown at 5270. This flocculation analysis can be performed using any technique capable of being understood by anyone skilled in the art, including but not limited to:

A standard jar test;

The system shown and described with reference to FIG. 6;

The instrument shown and described with reference to FIG. 8;

The unit shown at 13 and described with reference to FIG. 10;

The unit shown at 1300 and described with reference to FIG. 11;

The unit shown at 1400 and described with reference to FIG. 12; and

The device shown at 211 in FIG. 13 and FIG. 15 and described with reference to FIG. 13-30.

Having analyzed flocculation for one HMS dosage in 5270, one needs to determine if the HMS dosage is optimized, a step shown at 5280. This can be done by making comparisons of the current flocculation performance by:

(a) Running multiple tests in which HMS doses for the plant water are changed, i.e. repeating step 5290 with varying HMS doses in the region of the calculated HMS dose from step 5260 and comparing the flocculation results using the decision table shown in FIG. 24 to advise on further HMS doses and tests to be run; and/or by (b) Comparing current flocculation performance with historical flocculation data using the decision table that was described with reference to FIG. 24 to determine whether HMS dose is optimized.

With regard to steps 5210 and 5224 in FIG. 32, there can be a problem in that hydrolyzing metal salts (HMS), such as aluminum sulfate $Al_2(SO_4)_3$ and ferric sulfate $Fe_2(SO_4)_3$, as well as their numerous variant species in use today, when dispersed in surface water undergo hydrolysis—fast reactions with adjacent water molecules $H_2O$, to initially form, e.g., $Al(OH)_t^{++}$, and thence other powerful series of species in both parallel as well as sequentially reactions-such as, e.g. $Al_7(OH)_{32}^{+7}$, and numerous other positively charged species. These positively-charged species can eventually form a charge-neutral solid floc particle precipitate, $Al_2(SO_4)_3°$. In parallel, those several intermediate, short lived, positively charge species react with the negatively charged pollutant species when they collide randomly due to Brownian motion; thereby forming a precipitate solid such as $Al(OH)_n$ $AFA_{(s)}$, where AFA(s) is aquatic fulvic acid, a major form of aquatic humic matter.

Unfortunately only 2% to 6% of the aluminums' positive charge reacts with the raw-water negative charge. This low percentage is due to the dominate tendency for the hydrolysis or reactions with OH— that reduces alum's charge effective charge. The actual working charge-equivalence efficiency value is of high importance because lowering HMS optimum dose has a domino effect for increasing plant net water production, lower cost of HMS, sludge disposal, base addition for alkalinity replacement. Moreover, those effects are very dependent upon pH. Embodiments of the present invention provide a means of routinely computing this metric expressed in terms of the molecular element (Al 26.98 gm/mole, or Fe 55.84 gm/mole); herein defined as $\rho_f$=meq/g of metal. Thus, any increase in $\rho_f$ such as described herein can provide guidance on HMS dosages that are both cost effective and beneficial to the filtration pretreatment process. Finally, it is vital to recognize that independently raw-water TOC/DOC and charge demand can vary significantly due to outside causes. For example, in spring runoff as occurs in the western US, as much as a 4-fold (or 400%) rise and thence fall.

Referring to the steps in box 5200 in FIG. 32 in conjunction with FIG. 10 and FIG. 11, it should be noted that the output of box 5200 in FIG. 32 could be fed into a side-stream analysis unit such as that shown at 13 in FIG. 10 or 1300 in FIG. 11. In one embodiment, this side-stream analysis unit, 13 or 1300, could be used to perform step 5210 and/or step 5254 in FIG. 32 and the results of or both of these titrations and/or the computation of functional charge density, shown at 5256 could be used to determine the HMS dose for the water treatment process and any adjustments (steps 5260 and 5290) that need to be made. Such side stream units (13 or 1300) could be used to optimize the process of controlling the HMS dosage for a water treatment plant.

Once, the HMS dosage is optimized (step 5280), the method shown in FIG. 32 optimizes polymer coagulant dosage, box 5300. FIG. 32 provides more detail of one method for optimizing polymer coagulant dosage. Referring to box 5300 in FIG. 32, the sequence of actions to optimize polymer coagulant dose begins with the step shown at 5310, a test of a sample of raw water that has received (a) an optimized acid-base dose, as shown with reference to box 5100, (b) an optimized hydrolyzing metal salt (HMS) dose, as shown with reference to box 5200, and an experimental dose of polymer coagulant. This sample is then processed and the flocculation is analyzed. The processing and analysis of flocculation can be performed using any instrument capable of being understood by anyone skilled in the art, including but not limited to the instrument shown at 1300 in FIG. 11, the instrument shown at 1400 in FIG. 12, and the instrument shown at 211 in FIG. 13 and FIG. 15

Further referring to the polymer coagulant dosing optimization process in box 5300 in FIG. 32, one can determine if the polymer dose is optimized by performing at multiple tests of samples of raw water with the optimized acid-base dose and optimized hydrolyzing metal salt dose and different experimental polymer coagulant doses, (i.e. repeating step 5310 with different polymer coagulant dosages). The results of these tests can be used to create curves, similar to those shown and described with reference to FIG. 23. Based on these test results, one can determine if the polymer coagulant dose has been optimized, a step shown at 5320. If the polymer coagulant dose has been optimized, the plant operator can use this optimum polymer coagulant dose in the water plant system and monitor the water treatment process flocculation, as shown at step 5400. If the polymer coagulant dose is not optimized, one can go to the step shown at 5330 and change the polymer coagulant dose based on the decision table shown and described with reference to FIG. 24.

This decision table can be used to determine if polymer coagulant dosage should be increased or decreased in subsequent tests 5310.

Once the current raw water dosing of all the coagulant types, acid/base/pH coagulant, HMS coagulant, and polymer coagulant have been sequentially optimized, continuation of monitoring water treatment process flocculation 5400 and historical record updating 5470 begins. If, at any time, it is determined that flocculation has changed, a decision shown at 5480, the cause of this change should be found. One potential cause is that the water process has stopped, a decision shown at 5490, in which case the process shown at 5000 in FIG. 32 stops. If flocculation has changed and the water plant is still operating, this means that there has been a change to the chemistry of the raw water entering the plant and the entire process shown in FIG. 32 is repeated.

FIG. 33 shows a method for generating a standardized pDMDAC titrant. This method of analysis is built around two important phenomena:

First, this method involves use of an endpoint based upon orthotoluidine blue, chloride (o-TB), a metachromatic dye that undergoes color shifts of two wavelengths (520 & 640 nm); simultaneously, which provides un-paralleled endpoint precision. See step 5222.

Second, polymer binding affinities are extremely high and are on the order of $10^3$ to $10^4$ individual segments of the flexible polymer are available for binding. For complete polymer molecule detachment all bound segments, $B_s$, must all detach simultaneously, once the polymer is exposed to a binding surface with multiple adsorption sites, $A_s$. And for complete separation when the $B_s/A_s<1$ the probability of detachment is trivial. Note, at optimum polymer dosing $B_s \sim = \frac{1}{2} * A_s$. This high binding affinity produces reproducible, non-reversible titration reactions.

Further referring to FIG. 33, accurate calibration of the chemicals for raw-water charge equivalence (N, normality, typically at micro equivalence per liter (µeq/L) of a titrant such pDMDAC (poly(dimethyl diallyl ammonium chloride)), involves the following steps:

1. Prepare a solution of an appropriate reference standard of a known positive charge such as CPD, cetylpyridinium chloride, monohydrate (2.7 meq/gm), as shown at 5224. See below for all chemical details.
2. One needs to have othotoludine blue (step 5222), polyvinyl sulfate potassium (step 5226), and a polymer coagulant solution (5234) on hand.
3. Titrate a negative (polyanion) such as poly vinyl sulfate, potassium (pVSK, see step 5226), in the presence of o-TB (step 5222) and CPD (step 5224), past the equivalence or end point, as shown at 5230.
4. Step 5230 then allows one to compute pVS⁻ solution eq/L, as shown at 5232.
5. Next, calibrate the pDMDAC solution plus o-TB indicator, with incremental volumes of pVSK addition to a point past the equivalence point, as shown at 5240.
6. Step 5240 then allows one to calculate the positive charge equivalence value (µeq/L) of pDMDAC (step 5242) for application in water-treatment-plant raw water influent stream, according to the following equations:

$$(NV)_{p^+} + (NV)_{p^-} + (NV)_{D^+} + E_{app} = 0$$

$$V_{p^-} = -\left[\frac{E_{app} + (NV)_{D^+}}{N_{p^-}}\right] - \left[\frac{N_{p^+}}{N_{p^-}}\right] V_{p^+}$$

-continued $$\text{Slope} = -\left[\frac{N_{p^+}}{N_{p^-}}\right]$$

$$\text{Intercept} = -\left[\frac{E_{app} + (NV)_{D^+}}{N_{p^-}}\right]$$

$E_{app}$ ≡ equivalence demand of apparatus (eq), sign unknown

Subscripts refer to polymer of charge +/−, and $D^+$ denotes cationic dye

The equations above show how to determine $E_{app}$, the equivalence demand and the calculation of the unknown pDMDAC normality concentration, $N_2$, (eq/L): $N_1 V_1 = N_2 V_2$, where N≡normality (eq/L) and V≡volume (L). Alternately, unappalled accuracy can be obtained employing the analyte dilution procedure.

Additional detailed information regarding the above-mentioned chemical species is provided below:

pVSK poly(vinyl sulfate, potassium), CAS no. 26837-42-2 (Chemical Abstracts Services), ($M_w$ (monomer molecular weight)=161.2 g/mole, DP (number of monomer units per polymer molecule)=200, $\rho_p$ (charge density) meq/g=5.5, $pK_a$ pH of 50% degree of ionization, Use—anionic titrant.

pDMDAC (poly(Diallyl dimethylammonium chloride), CAS no. 7398-69-8, monomer $M_w$=161.8 g/mole, DP 300-to-10,000=200, $\rho_p$ (charge density) meq/g=4.0, $pK_a$=>10, Use—cationic titrant & coagulant chemical.

CPD (cetylpyridium, chloride monohydrate), CAS no. 6004-24-6, $M_w$=358.01 g/mole, $\rho_p$ (charge density) meq/g=2.7, $pK_a$=>10, Use—cationic charge standard.

o-TB (ortho toluidine blue, chloride), CAS no. 92-31-9, $M_w$=305.83 g/mole, $\rho_p$ (charge density) meq/g=2.7, $pK_a$=>10, Use—endpoint indicator.

The acid-base dosage optimization process (5100 in FIG. 31 and FIG. 32) has the following direct benefits:
(a) lowers system raw water charge; and
(b) increases hydrolyzing metal salt positive charge percentage.

The hydrolyzing metal salt dosage optimization process (5100 in FIG. 31 and FIG. 32) has the following direct benefits:
(a) minimizes hydrolyzing metal salt dosage;
(b) improves initial floc formation; and
(c) minimizes sludge.

The polymer coagulant dosage optimization process (5100 in FIG. 31 and FIG. 32) has the following direct benefits:
(a) builds the strongest and most removable floc-pollutant particles; and
(b) ensures that pollutant removal is maximized.

Referring generally to the process for optimizing coagulant dosing described in FIGS. 31-33, and the preceding comments, the process described herein has the following benefits:
(a) reduced usage of all three main classes of chemicals: acid-base, hydrolyzing metal salts, and polymer coagulants;
(b) optimized production of floc, consistent with maximizing organic acid charge reduction, which reduces filter clogging, and other downstream water processing costs; and
(c) safer drinking water.

The alternative features and configurations described in this document can be combined in any way capable of being understood by anyone skilled in the art. A number of variations and modifications of the disclosed embodiments can also be used. The principles described here can also be used for in applications other than water treatment processes. While the principles of the disclosure have been described above in connection with specific apparatuses and methods, it is to be clearly understood that this description is made only by way of example and not as limitation on the scope of the disclosure.

What is claimed is:

1. A method for optimizing coagulant dosing of raw water in a water treatment process, the method comprising the steps of:
   determining a dosage of pH adjusting chemicals to be added to the raw water in response to a measurement of the organic content, the alkalinity, and the pH of the raw water;
   flocculation testing a first hydrolyzing-metal-salt water sample wherein:
      the first hydrolyzing-metal-salt water sample comprises a combination of the raw water, the dosage of pH adjusting chemicals, and a calculated first dosage of a hydrolyzing metal salt; and
      flocculation testing of the first hydrolyzing-metal-salt water sample comprises a light source and a digital camera configured for recording a first plurality of digital images of illuminated suspended floc particles in the first hydrolyzing-metal-salt water sample;
   determining a hydrolyzing metal salt dosage in response to the flocculation testing of the first hydrolyzing-metal-salt water sample;
   performing a polymer coagulant flocculation test of a first polymer coagulant water sample wherein:
      the first polymer coagulant water sample comprises the raw water, the dosage of pH adjusting chemicals, the hydrolyzing metal salt dosage, and a first polymer coagulant dosage; and
      performing a polymer coagulant flocculation test of the first polymer coagulant water sample comprises the light source and the digital camera configured for recording a second plurality of digital images of illuminated suspended floc particles in the first polymer coagulant water sample;
   performing a first polymer coagulant flocculation test of a second polymer coagulant water sample wherein:
      the second polymer coagulant water sample comprises the raw water, the dosage of pH adjusting chemicals, the hydrolyzing metal salt dosage, and a second polymer coagulant dosage;
      the second polymer coagulant dosage is different from the first poly trier coagulant dosage; and
      performing a second polymer coagulant flocculation test of the second polymer coagulant water sample comprises the light source and the digital camera configured for recording a third plurality of digital images of illuminated suspended floc particles in the second polymer coagulant water sample; and
   determining the polymer coagulant dosage in response to the polymer coagulant flocculation test of the first polymer coagulant water sample and the polymer coagulant flocculation test of the second polymer coagulant water sample;
   and
   wherein all preceding steps are performed in the order listed herein.

2. The method of claim 1 wherein:
   the method is configured for a water treatment process that produces treated drinking water for human consumption; and
   determining the polymer coagulant dosage further comprises the following iterative steps:
      performing an additional polymer coagulant flocculation test with an increased polymer coagulant dosage than the most recent polymer coagulant flocculation test if the most recent polymer coagulant flocculation test produced smaller floc than the polymer coagulant flocculation test immediately preceding the most recent polymer coagulant flocculation test and the polymer coagulant dosage in the most recent polymer coagulant flocculation test was less than the polymer coagulant dosage in the polymer coagulant flocculation test immediately preceding the most recent polymer coagulant flocculation test;
      performing an additional polymer coagulant flocculation test with a decreased polymer coagulant dosage than the most recent polymer coagulant flocculation test if the most recent polymer coagulant flocculation test produced larger floc than the polymer coagulant flocculation test immediately preceding the most recent polymer coagulant flocculation test and the polymer coagulant dosage in the most recent polymer coagulant flocculation test was less than the polymer coagulant dosage in the polymer coagulant flocculation test immediately preceding the most recent polymer coagulant flocculation test;
      performing an additional polymer coagulant flocculation test with a decreased polymer coagulant dosage than the most recent polymer coagulant flocculation test if the most recent polymer coagulant flocculation test produced smaller floc than the polymer coagulant flocculation test immediately preceding the most recent polymer coagulant flocculation test and the polymer coagulant dosage in the most recent polymer coagulant flocculation test was greater than the polymer coagulant dosage in the polymer coagulant flocculation test immediately preceding the most recent polymer coagulant flocculation test;
      performing an additional polymer coagulant flocculation test with an increased polymer coagulant dosage than the most recent polymer coagulant flocculation test if the most recent polymer coagulant flocculation test produced larger floc than the polymer coagulant flocculation test immediately preceding the most recent polymer coagulant flocculation test and the polymer coagulant dosage in the most recent polymer coagulant flocculation test was greater than the polymer coagulant dosage in the polymer coagulant flocculation test immediately preceding the most recent polymer coagulant flocculation test; and
      repeating the preceding iterative steps until the floc size change between the two most recent polymer coagulant flocculation tests of the two most recent polymer coagulant water samples indicates that floc size has not changed sufficiently to justify further flocculation testing of polymer coagulant water samples.

3. The method of claim 1 wherein flocculation testing of the first hydrolyzing-metal-salt water sample is performed in a portable system, the portable system comprising:
   a user-removable chamber for holding the first hydrolyzing-metal-salt water sample, wherein:

the chamber comprises:
a substantially square shaped horizontal cross section; and
an aperture located in a top portion of the chamber;
the chamber is configured for:
receiving the water and first hydrolyzing-metal-salt water sample through the aperture; and
manually disposing the first hydrolyzing-metal-salt water sample through the aperture; and
an instrument configured for insertion partially into the first hydrolyzing-metal-salt water sample in the chamber, wherein:
the instrument is portable;
the instrument is configured for:
manual vertical insertion of a first instrument part through the aperture;
manual vertical insertion of the first instrument part into the first-hydrolyzing metal-salt water sample in the chamber; and
viewing suspended particles in a region of the first hydrolyzing-metal-salt water sample in the chamber wherein the region is in the bottom half of the user-removable chamber;
the instrument comprises the light source, wherein the light source is configured for illumination of the particles in the region;
the instrument comprises the digital optical camera wherein:
the digital camera is configured for recording the plurality of digital images of the illuminated suspended particles;
the instrument comprises a mixing unit that comprises a mixing paddle and a mixer motor wherein:
the mixing paddle is configured for submersion into the first-hydrolyzing metal-salt water sample in the chamber;
the mixing paddle comprises at least one blade that is configured to be located at approximately the same vertical location as the region; and
the mixing paddle is connected and responsive to the shaft of the mixer motor;
the instrument comprises a user-programmable controller wherein:
the light source the digital camera, and the mixing motor are responsive to the user-programmable controller;
the controller is configured for receiving image data from the digital camera during:
a flocculation phase when the mixer motor is on; and
a settling phase when the mixer motor is off, wherein the settling phase occurs after the flocculation phase;
the instrument comprises a user-programmable input device wherein:
the controller is responsive to the input device;
the mixing speed during the flocculation phase is stored by the controller and responsive to the input device; and
the duration of flocculation phase is stored by the controller and responsive to the input device and the real time clock;
the instrument comprises a display wherein:
the display is responsive to the controller; and
the display is configured for presenting a graph of a floc characteristic as a function of time during the flocculation phase and the settling phase, wherein the floc characteristic is selected from the group of:
floc particle count, wherein the floc particle count comprises a count of the quantity of suspended floc particles divided by a volume of the region:
computed average floc particle volume;
floc volume concentration wherein the floc volume concentration comprises the ratio of a volume of the suspended particles in the region divided by the total volume of the region; and
equivalent average spherical floc particle diameter; and
wherein the floc characteristic has been computed by computer code in the controller in response to the image data and time data from the real time clock.

4. The method of claim 1 wherein flocculation testing of the first polymer coagulant water sample is performed in a portable system, the portable system comprising:
a user-removable chamber for holding the first polymer coagulant water sample, wherein:
the chamber comprises:
a substantially square shaped horizontal cross section; and
an aperture located in a top portion of the chamber;
the chamber is configured for:
receiving the first polymer coagulant water sample through the aperture; and
manually disposing the first polymer coagulant water sample through the aperture; and
an instrument configured for insertion partially into the first polymer coagulant water sample in the chamber, wherein:
the instrument is portable:
the instrument is configured for:
manual vertical insertion of a first instrument part through the aperture;
manual vertical insertion of the first instrument part into the first polymer coagulant water sample in the chamber;
and
viewing suspended particles in a region of the first polymer coagulant water sample in the chamber wherein the region is in the bottom half of the user-removable chamber;
the instrument comprises the light source, wherein the light source is configured for illumination of the particles in the region;
the instrument comprises the digital optical camera wherein:
the digital camera is configured for recording the plurality of digital images of the illuminated suspended particles;
the instrument comprises a mixing unit that comprises a mixing paddle and a mixer motor wherein:
the mixing paddle is configured for submersion into the first-hydrolyzing metal-salt water sample in the chamber;
the mixing paddle comprises at least one blade that is configured to be located at approximately the same vertical location as the region; and
the mixing paddle is connected and responsive to the shaft of the mixer motor;
the instrument comprises a user-programmable controller wherein:

the light source, the digital camera, and the mixing motor are responsive to the user-programmable controller;

the controller is configured for receiving image data from the digital camera during:
 a flocculation phase when the mixer motor is on; and
 a settling phase when the mixer motor is off, wherein the settling phase occurs after the flocculation phase;

the instrument comprises a user-programmable input device wherein:
 the controller is responsive to the input device;
 the mixing speed during the flocculation phase is stored by the controller and responsive to the input device; and
 the duration of flocculation phase is stored by the controller and responsive to the input device and the real time clock;

the instrument comprises a display wherein:
 the display is responsive to the controller; and
 the display is configured for presenting a graph of a floc characteristic as a function of time during the flocculation phase and the settling phase, wherein the floc characteristic is selected from the group of:
  floc particle count, wherein the floc particle count comprises a count of the quantity of suspended floc particles divided by a volume of the region;
  computed average floc particle volume;
  floc volume concentration wherein the floc volume concentration comprises the ratio of a volume of the suspended particles in the region divided by the total volume of the region; and
  equivalent average spherical floc particle diameter; and
 wherein the floc characteristic has been computed by computer code in the controller in response to the image data and time data from the real time clock.

5. A method for optimizing water treatment comprising the steps of:
 determining a dosage of pH adjusting chemicals to be added to input water to produce pH-dosed water in response to the organic content, the alkalinity, and the pH of the input water;
 determining a dosage of hydrolyzing metal salt to be added to the pH-dosed-water to produce metal-salt-dosed water, wherein:
  determining the dosage of hydrolyzing metal salt comprises a hydrolyzing metal salt flocculation test;
  the hydrolyzing metal salt flocculation test comprises a light source and a digital camera;
  the light source and the digital camera are configured to generate a first plurality of digital images of illuminated suspended floc particles in the metal-salt-dosed water; and
  the dosage of hydrolyzing metal salt is determined in response to the first plurality of digital images of the illuminated suspended floc particles from the digital camera; and
 determining a dosage of polymer coagulant to be added to the metal-salt-dosed water to produce flocculatable water wherein determining the dosage of polymer coagulant comprises:
  a first polymer coagulant flocculation test that comprises the light source and the digital camera configured for recording a second plurality of digital images of illuminated suspended floc particles in the metal-salt-dosed water that further comprises a first polymer coagulant dosage; and
  a second polymer coagulant flocculation test that comprises the light source and the digital camera configured for recording a third plurality of digital images of illuminated suspended floc particles in the metal-salt-closed water that further comprises second polymer coagulant dosage, wherein the second polymer coagulant dosage is different from the first polymer coagulant dosage;
  a comparison of the results of the first polymer coagulant flocculation test the results of the second polymer coagulant flocculation test.

6. The method of claim 5 wherein:
the method for optimizing water treatment is configured a water treatment process that produces treated drinking water for human consumption; and
determining the dosage of polymer coagulant further comprises the following iterative procedure for reaching the polymer coagulant dosage:
 performing an additional polymer coagulant flocculation test with an increased polymer coagulant dosage than the most recent polymer coagulant flocculation test if the most recent polymer coagulant flocculation test produced smaller floc than the polymer coagulant flocculation test immediately preceding the most recent polymer coagulant flocculation test and the polymer coagulant dosage in the most recent polymer coagulant flocculation test was less than the polymer coagulant dosage in the polymer coagulant flocculation test immediately preceding the most recent polymer coagulant flocculation test;
 performing an additional polymer coagulant flocculation test with a decreased polymer coagulant dosage than the most recent polymer coagulant flocculation test if the most recent polymer coagulant flocculation test produced larger floc than the polymer coagulant flocculation test immediately preceding the most recent polymer coagulant flocculation test and the polymer coagulant dosage in the most recent polymer coagulant flocculation test was less than the polymer coagulant dosage in the polymer coagulant flocculation test immediately preceding the most recent polymer coagulant flocculation dosage test;
 performing an additional polymer coagulant flocculation test with a decreased polymer coagulant dosage than the most recent polymer coagulant flocculation test if the most recent polymer coagulant flocculation test produced smaller floc than the polymer coagulant flocculation test immediately preceding the most recent polymer coagulant flocculation test and the polymer coagulant dosage in the most recent polymer coagulant flocculation test was greater than the polymer coagulant dosage in the polymer coagulant flocculation test immediately preceding the most recent polymer coagulant flocculation test; or
 performing an additional polymer coagulant flocculation test with an increased polymer coagulant dosage than the most recent polymer coagulant flocculation test if the most recent polymer coagulant flocculation test produced larger floc than the polymer coagulant flocculation test immediately preceding the most recent polymer coagulant flocculation test and the polymer coagulant dosage in the most recent polymer coagulant flocculation test was greater than the polymer coagulant dosage in the polymer coagulant flocculation test immediately preceding the most recent polymer coagulant flocculation test; and repeating this iterative procedure until the floc size change between the two most recent polymer coagulant flocculation tests of the two most recent polymer coagulant water samples indicates that floc size has not changed sufficiently to justify further flocculation testing of polymer coagulant water samples.

7. The method of claim 5 wherein:
determining the dosage of pH adjusting chemicals further comprises an adjustment of an acid feed or a base feed for a water treatment plant.

8. The method of claim 5 wherein:
determining the dosage of hydrolyzing metal salt comprises a test of the charge demand of the pH-dosed water.

9. The method of claim 5 wherein:
determining the dosage of hydrolyzing metal salt comprises a titration of the pH-dosed water with a polycation polymer.

10. The method of claim 5 wherein:
determining the dosage of hydrolyzing metal salt comprises a plurality of hydrolyzing-metal-salt flocculation tests with varying hydrolyzing-metal salt-dosages added to samples of pH-dosed water, the plurality of tests being conducted using the following iterative procedure:
re-running the hydrolyzing metal salt flocculation test with an increased hydrolyzing metal salt dosage if the most recent hydrolyzing metal salt flocculation test produced smaller floc than the hydrolyzing metal salt flocculation test immediately preceding the most recent hydrolyzing metal salt flocculation test and the hydrolyzing metal salt dosage in the most recent hydrolyzing metal salt flocculation test was less than the hydrolyzing metal salt dosage in the flocculation test immediately preceding the most recent hydrolyzing metal salt dosage test;
re-running the hydrolyzing metal salt flocculation test with a decreased hydrolyzing metal salt dosage if the most recent hydrolyzing metal salt flocculation test produced larger floc than the hydrolyzing metal salt flocculation test immediately preceding the most recent hydrolyzing metal salt flocculation test and the hydrolyzing metal salt dosage in the most recent hydrolyzing metal salt flocculation test was less than the hydrolyzing metal salt dosage in the flocculation test immediately preceding the most recent hydrolyzing metal salt dosage test;
re-running the hydrolyzing metal salt flocculation test with a decreased hydrolyzing metal salt dosage if the most recent hydrolyzing metal salt flocculation test produced smaller floc than the hydrolyzing metal salt flocculation test immediately preceding the most recent hydrolyzing metal salt flocculation test and the hydrolyzing metal salt dosage in the most recent hydrolyzing metal salt flocculation test was greater than the hydrolyzing metal salt dosage in the flocculation test immediately preceding the most recent hydrolyzing metal salt dosage test;
re-running the hydrolyzing metal salt flocculation test with an increased hydrolyzing metal salt dosage if the most recent hydrolyzing metal salt flocculation test produced larger floc than the hydrolyzing metal salt flocculation test immediately preceding the most recent hydrolyzing metal salt flocculation test and the hydrolyzing metal salt dosage in the most recent hydrolyzing metal salt flocculation test was greater than the hydrolyzing metal salt dosage in the flocculation test immediately preceding the most recent by metal salt dosage test; and repeating this iterative procedure until the floc size change between the two most recent flocculation tests of the two most recent hydrolyzing metal salt water samples indicates that floc size has not changed sufficiently to justify further flocculation testing of hydrolyzing metal salt water samples.

11. The method of claim 5 wherein:
determining the dosage of pH adjusting chemicals is performed automatically in response to instruments that measure the organic content, the alkalinity, and the pH of the input water.

12. The method of claim 5 wherein:
determining the dosage of hydrolyzing metal salt comprises a computation of functional charge density of the pH-dosed water.

13. The method of claim 5 wherein:
determining dosage of hydrolyzing metal salt comprises a titration of the pH-dosed water and a hydrolyzing metal salt to determine the dosage of hydrolyzing metal salt needed to produce water with a target zeta potential.

14. The method of claim 5 wherein:
the method further comprises the step of monitoring water treatment process flocculation wherein monitoring water treatment flocculation comprises comparing a current flocculation parameter of the flocculatable water with a historic flocculation parameter wherein the flocculation parameter is selected from the group of:
floc number concentration per unit volume;
individual floc-particle volume;
mean floc particle volume concentration per unit volume;
mean floc particle diameter of a sphere of equivalent volume;
floc particle growth rate;
maximum floc particle diameter;
rate of settling of floc-particle volume concentration; and
extent of settling of floc-particle volume concentration.

15. The method of claim 5 wherein the method further comprises the steps of:
monitoring water treatment process flocculation wherein monitoring water treatment flocculation comprises comparing a current flocculation parameter with a historic flocculation parameter; and
re-determining the dosage of pH adjusting chemicals;
re-determining the dosage of hydrolyzing metal salt; and
re-determining the dosage of polymer coagulant;
if the water treatment process flocculation has changed.

16. The method of claim 5 wherein:
determining the dosage of hydrolyzing metal salt comprises an automatic flocculation testing instrument wherein:
the automatic instrument further comprises the digital camera; and
the automatic instrument is located downstream of a hydrolyzing metal salt addition point in a water treatment plant.

17. The method of claim 5 wherein:
the first polymer coagulant flocculation test comprises an automatic flocculation testing instrument wherein:
the automatic instrument further comprises the digital camera; and the automatic instrument is located downstream of a polymer coagulant addition point in a water treatment plant.

18. The method of claim 5 wherein:
the light source and the digital camera for the hydrolyzing metal salt flocculation test are located in an instrument that further comprises:
- a chamber for isolating the input water with the dosage of pH adjusting chemicals and the first dosage of hydrolyzing metal salt, wherein the chamber comprises an inlet and an outlet;
- a mixer; and
- a controller wherein the controller is configured for receiving image data from the digital camera during:
  - a flocculation phase when the mixer motor is on; and
  - a settling phase when the mixer motor is off, wherein the settling phase occurs after the flocculation phase.

19. The method of claim 5 wherein:
the light source and the digital camera for the hydrolyzing metal salt flocculation test are located in an instrument that further comprises a display, a controller, and a real time clock wherein:
the display is responsive to the controller; and
the display is configured for presenting a graph of a floc characteristic as a function of time during the flocculation phase and the settling phase, wherein the floc characteristic is selected from the group of:
- floc particle count, wherein the floc particle count comprises a count of the quantity of suspended floc particles divided by a volume of the region;
- computed average floc particle volume;
- floc volume concentration wherein the floc volume concentration comprises the ratio of a volume of the suspended particles in the region divided by the total volume of the region; and
- equivalent average spherical floc particle diameter; and
wherein the floc characteristic has been computed by computer code in the controller in response to the image data and time data from the real time clock.

20. A method for optimizing the treatment of water, the method comprising the steps of:
- determining a dosage of pH adjusting chemicals to be added to the water to produce a pH-dosed mixture in response to the organic content, the alkalinity, and the pH of the water;
- producing the pH-dosed mixture that comprises the water and the dosage of pH adjusting chemicals;
- determining a dosage of hydrolyzing metal salt to be added to the pH-dosed mixture by:
  - adding hydrolyzing metal salt to the pH-dosed mixture to produce a metal-salt-dosed mixture;
  - observing a first plurality of digital camera images of suspended floc particles in the metal-salt-dosed mixture;
  - determining the dosage of hydrolyzing metal salt in response to the first plurality of digital camera images;
- determining a polymer coagulant dosage to be added to the metal-salt-dosed mixture by:
  - adding a first polymer coagulant dosage to the metal-salt-dosed mixture to produce a first coagulant-dosed sample;
  - observing a second plurality of digital camera images of suspended floc particles in the first coagulant-dosed sample;
  - adding a second polymer coagulant dosage to the metal-salt-dosed to produce a second coagulant-dosed sample, wherein the second polymer coagulant dosage is different than the first coagulant dosage;
  - observing a third plurality of digital camera images of suspended floc particles in the second coagulant-sample;
  - selecting the polymer coagulant dosage in response to the second plurality of digital images and the third plurality of digital images.

* * * * *